United States Patent
Iyer et al.

(10) Patent No.: US 10,906,946 B2
(45) Date of Patent: Feb. 2, 2021

(54) THROMBIN INHIBITORS

(71) Applicants: National University of Singapore, Singapore (SG); Institute of Zoology, Slovak Academy of Sciences, Bratislava (SK)

(72) Inventors: Janaki Krishnamoorthy Iyer, Singapore (SG); Cho Yeow Koh, Singapore (SG); R. Manjunatha Kini, Singapore (SG); Maria Kazimirova, Bratislava (SK); Ladislav Roller, Bratislava (SK)

(73) Assignees: National University of Singapore, Singapore (SG); Institute of Zoology, Slovak Academy of Sciences, Bratislava (SK)

( * ) Notice: Subject to any disclaimer, the term of this patent is extended or adjusted under 35 U.S.C. 154(b) by 82 days.

(21) Appl. No.: 15/737,266

(22) PCT Filed: Jun. 17, 2016

(86) PCT No.: PCT/SG2016/050278
§ 371 (c)(1),
(2) Date: Dec. 15, 2017

(87) PCT Pub. No.: WO2016/204696
PCT Pub. Date: Dec. 22, 2016

(65) Prior Publication Data
US 2019/0002511 A1    Jan. 3, 2019

Related U.S. Application Data

(60) Provisional application No. 62/230,923, filed on Jun. 18, 2015.

(51) Int. Cl.
*C07K 14/435* (2006.01)
*C07K 14/81* (2006.01)
*A61P 7/02* (2006.01)
*A61K 38/00* (2006.01)

(52) U.S. Cl.
CPC .......... *C07K 14/43527* (2013.01); *A61P 7/02* (2018.01); *C07K 14/811* (2013.01); *A61K 38/00* (2013.01)

(58) Field of Classification Search
CPC ... C07K 14/43527; C07K 14/811; A61P 7/02; A61K 38/00
See application file for complete search history.

(56) References Cited

PUBLICATIONS

Koh et al, Variegin, a Novel Fast and Tight Binding Thrombin Inhibitor from the Tropical Bont Tick, The Journal of Biological Chemistry, 2007, 282, pp. 29101-29113.*
Huntington, Natural inhibitors of thrombin, Thromb Haemost, 2014, 111, pp. 583-589.*
TPA_inf: hirudin-like protein [Amblyomma variegatum], from https://www.ncbi.nlm.nih.gov/protein/DAA34688.1?report=genbank&log$=protalign&blast_rank=1&RID=6CTYSPW9016, Mar. 5, 2011, pp. 1-2.*
UnitProtKB Accession No. Q6F3E8_AMBVA dated Aug. 16, 2004.
ENA Accession No. AB183707.1, dated Jul. 14, 2004.
UnitProtKB Accession No. B5M705_AMBAM dated Oct. 14, 2008.
ENA Accession No. EZ000183.1 dated Aug. 24, 2008.
UnitProtKB Accession No. C9W1T3_RHISA dated Nov. 24, 2009.
ENA Accession No. EZ406235.1 dated Oct. 15, 2009.
UniProtKB Accession No. E2J6T8_9ACAR dated Nov. 30, 2010.
ENA Accession No. HP429131.1 dated Sep. 20, 2010.
GenBank Accession No. GT030255.1 dated Sep. 3, 2009.
GenBank Accession No. GT030221.1 dated Sep. 3, 2009.
GenBank Accession No. GR907234.1 dated Jul. 30, 2009.
GenBank Accession No. GR907989.1 dated Jul. 30, 2009.
GenBank Accession No. GR907956.1 dated Jul. 30, 2009.
GenBank Accession No. GR907391.1 dated Jul. 30, 2009.
GenBank Accession No. GR907111.1 dated Jul. 30, 2009.
GenBank Accession No. GR908630.1 dated Jul. 30, 2009.
GenBank Accession No. GR907806.1 dated Jul. 30, 2009.
GenBank Accession No. GR908940.1 dated Jul. 30, 2009.
GenBank Accession No. GR908483.1 dated Jul. 30, 2009.
International Search Report in PCT/SG2016/050278, dated Aug. 26, 2016, 5 pages.
Written Opinion of the International Searching Authority in PCT/SG2016/050278, dated Aug. 26, 2016, 6 pages.
EBI accession No. BK007729. Last updated on May 10, 2014.
Iyer et al., "Avathrin: a novel thrombin inhibitor derived from a multicopy precursor in the salivary glands of the ixodid tick, Amblyomma variegatum," FASEB J, (2017) 31:2981-2995.
Kazimirova et al., "Tick salivary compounds: their role in modulation of host defences and pathogen transmission," Frontiers in Cellular and Infection Microbiology (2013) 3(43):1-19.
Koh et al., "Variegin, a Novel Fast and Tight Binding Thrombin Inhibitor from the Tropical Bont Tick," Journal of Biological Chemistry (2007) 282(40):29101-29113.
Ribeiro et al., "A further insight into the sialome of the tropical bont tick, Amblyomma variegatum," BMC Genomics (2011) 12:136.
Supplementary European Search Report for EP 16812056, dated Oct. 4, 2018, 9 pages.

* cited by examiner

*Primary Examiner* — Li N Komatsu
(74) *Attorney, Agent, or Firm* — Morrison & Foerster LLP

(57) ABSTRACT

The present invention provides isolated peptides, variants and fragments thereof that are capable of binding with a high level of specificity to thrombin and inhibiting its activity. There is also provided uses of such peptides in methods of diagnosis and treatment, coating of medical devices and nucleic acids encoding the same.

20 Claims, 28 Drawing Sheets
Specification includes a Sequence Listing.

A

B

| Protein | Species | Sequence |
|---|---|---|
| Variegin | A. variegatum | SDQGDVAEPKMHKTAPPFDFEAIPEEYLDDES |
| Avathrin | A. variegatum | SGGHQTAVPKISKQGLGGDFEEIPSDEIIE |
| BM291228_1 | A. variegatum | SNDGSVAQPKLHRQSPGGDFEEFPEQAIEQ |
| BM293052 | A. variegatum | SDEAVRAIPKMYSTAPPGDFE-IPDDAIEE |
| TC395_1 | A. variegatum | SEQAGRAVPKMHQTPPPNDFERIPVEDYEE |
| ACG76173_1 | A. americanum | SGEHHTAVPKMSRKGLGGDFEDIPPEAYE |
| ACAJ0085C_1 | A. cajannense | SDVAHTAVPKMKGGH-GG-FEPIPIDYDE |

FIGURE 28

THROMBIN INHIBITORS

CROSS-REFERENCE TO RELATED APPLICATIONS

This application is a U.S. National Phase Application of International Patent Application No. PCT/SG2016/050278 having an international filing date of Jun. 17, 2016, published as WO 2016/204696 A1 on Dec. 22, 2016, which claims priority to U.S. Provisional Patent Application No. 62/230,923 filed Jun. 18, 2015, the disclosures of which are herein incorporated by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 255352004700SeqList.txt, date recorded: Aug. 18, 2020, size: 15,788 bytes).

FIELD OF THE INVENTION

The present invention is related to isolated peptides, variants and fragments thereof which specifically bind thrombin that causes coagulopathies in humans. There is also provided uses of such peptides in methods of diagnosis and treatment of thrombosis-related diseases, and for coating of medical devices.

BACKGROUND OF THE INVENTION

Haemostasis is the physiological process that minimizes extravasation of blood following a vascular injury. Blood coagulation, a part of this process involves activation of circulating zymogens by limited proteolysis in a sequential manner and culminates in the formation of a fibrin clot. Thrombin (FIIa) plays pivotal roles in haemostasis (Stubbs M. T. and Bode W. *Throm Res* 69, 1-58 (1993)). In its pro-haemostatic role: (a) it cleaves soluble fibrinogen to fibrin monomers, which polymerize to form a nascent clot (Versteeg H. H., et al., *Physiol Rev* 93, 327-358 (2013)); (b) it activates the transglutaminase (FXIII) that covalently crosslinks fibrin monomers to stabilize the clot; (c) it activates non-enzymatic cofactors (FV and FVIII) required for its own amplification; (d) it activates FXI which in turn activates the intrinsic pathway (Versteeg H. H., et al., *Physiol Rev* 93, 327-358 (2013)); and (e) it activates platelets by cleaving protease-activated receptors leading to their shape change, degranulation and aggregation (Monroe D. M., et al., *Arterioscler Thromb Vasc Biol* 22, 1381-1389 (2002)). Conversely, thrombin also plays a significant role as an anticoagulant by down regulating the progression and amplification of the blood coagulation process: upon binding to thrombomodulin, it activates protein C, which in turn inactivates both cofactors FVa and FVIIIa to mitigate further thrombin generation (Di Cera E. *Mol Aspects Med* 29(4), 203-254 (2008)). These paradoxical procoagulant and anticoagulant roles of thrombin maintain a balance between uncontrolled bleeding and formation of obstructive thrombi, with sufficient thrombus formation when required.

Cardiovascular disease is the single largest killer worldwide and is a hefty contributor to the burden of non-communicable diseases (Chaudhari K., et al., *Nat. Rev. Drug. Discov* 13, 571-572 (2014)). Ischemic heart disease and stroke, both of which are pathological manifestations of thrombosis are the most common examples of cardiovascular disease and account for up to one in four deaths worldwide (Raskob G. *Thromb Haem* 112(5), 843-943 (2014)). Anticoagulants like direct thrombin inhibitors (DTIs), direct factor Xa (FXa) inhibitors and vitamin K antagonists (VKAs) comprise a significant fraction of the current therapeutic options as antithrombotic drugs. Some examples of DTIs used as therapeutic options are bivalirudin, the synthetic analogue of hirudin which is a bivalent inhibitor binding to the thrombin active site and exosite-; argatroban and dabigatran, small molecule univalent DTIs that bind to the active site alone; and low-molecular-weight-heparins (LMWHs) which inhibit thrombin in an antithrombin-dependent manner (Michiel Coppens, et al., *Circ Res* 112, 920-931 (2012)). Despite being popular options of anticoagulant therapy, these classes are fraught with limitations like narrow therapeutic window, individual dosing, high bleeding risks, poor bioavailability and high food-drug interactions (Bauer K. A. *Haem* 464-470 (2013)). Therefore, novel, superior anticoagulants with greater benefits are being sought.

Hematophagous animals have adapted a blood feeding diet and have evolved an assortment of molecules that control host haemostasis to ensure a continuous blood flow for successful feeding. Among anticoagulants, thrombin inhibitors take a central stage in these blood sucking parasites (Koh C. Y. and Kini R. M. *Expert Rev. Haematol* 1(2), 135-139 (2008)). Hirudin, haemadin, triabin, ornithodorin and rhodniin are some of the most extensively studied examples of specific families of thrombin inhibitors from hematophagous animals (Huntington J. A. *Thromb Haemost* 111, 583-589 (2014)). We have previously isolated and characterized a novel thrombin inhibitor we dubbed variegin (PCT/IB2008/002109), a 32-residue long peptide which is a fast, tight binding, and competitive thrombin inhibitor from the salivary gland extracts of the hard tick-*Amblyomma variegatum* (Koh C. Y., *J Biol Chem* 282 (40), 29101-29113 (2007)).

There is a need to provide more effective peptides as therapeutic agents for the treatment of cardiovascular and cerebrovascular diseases. Examples of uses include the treatment and prophylaxis of arterial and venous thrombosis causing heart attacks, stroke and embolism; for anticoagulation during unstable angina, coronary angioplasty, percutaneous coronary intervention and heart surgery. In addition, these peptides can also be developed as reagents, as anti-clotting agents in blood collection tubes and as surface coating materials on medical devices such as stents, catheters and medical tubing.

SUMMARY OF THE INVENTION

The present invention seeks to solve or ameliorate the problems described above and provide new peptides and variants thereof with improved affinity for thrombin. Although newly identified peptides 'avathrin' and 'ultravariegin' show limited sequence identity with variegin, they selectively inhibit thrombin in a similar fast, tight binding competitive mode with a $K_i$ of 545 pM and 4.4 pM, respectively. These affinities are approximately 5 and 650 times higher, respectively, for target (thrombin) than a similar peptide-based thrombin inhibitor used in the clinic (Bivalirudin™), which suffered from a lack of clear efficacy and need for continuous infusion. We have identified their important functional sites, assisted by high resolution three-dimensional structures and structure-function relationships of a number of variants of these thrombin inhibitors. New variants of these peptides with improved affinity for thrombin were designed and synthesized. We have successfully demonstrated in vivo efficacy of these peptides through a murine arterial thrombosis model. Also identified and studied other novel peptides from Ixodid ticks.

A first aspect of the invention provides thrombin inhibitors comprising an amino acid sequence selected from the group comprising SGGHQTAVPKISKQGLGGDFEEIPSDEIIE (SEQ ID NO: 1), a variant or fragment thereof, SDEAVRAIPKMYSTAPPGDFEEIPDDAIEE (SEQ ID NO: 2), a variant or fragment thereof, SEQ ID NO: 22, a variant or fragment thereof, SEQ ID NO: 23, a variant or fragment thereof, SEQ ID NO: 24, a variant or fragment thereof and SEQ ID NO: 25, a variant or fragment thereof.

In a preferred embodiment the amino acid sequence is selected from the group comprising;

```
                                            (SEQ ID NO: 3)
QTAVPKISKQGLGGDFEEIPSDEIIE;

(SEQ ID NO: 4)
ISKQGLGGDFEEIPSDEIIE;

(SEQ ID NO: 5)
SGGHQTAVPKIAKQGLGGDFEEIPSDEIIE;

(SEQ ID NO: 6)
SGGHQTAVPKIHKQGLGGDFEEIPSDEIIE;

(SEQ ID NO: 7)
SGGHQTAVPRISKQGLGGDFEEIPSDEIIE;

(SEQ ID NO: 8)
SGGHQTAVPXISKQGLGGDFEEIPSDEIIE, wherein X is
β-homoarginine;

(SEQ ID NO: 9)
SDEAVRAIPXMYSTAPPGDFEEIPDDAIEE, wherein X is
β-homoarginine;

(SEQ ID NO: 10)
SDQGDVAIPKMYSTAPPGDFEEIPDDAIEE;

(SEQ ID NO: 11)
SDEAVRAEPKMHKTAPPGDFEEIPDDAIEE;

(SEQ ID NO: 12)
SDEAVRAIPKMYSTAPPGDFEEIPEEYLDDES;

(SEQ ID NO: 13)
MYSTAPPGDFEEIPDDAIEE;

(SEQ ID NO: 14)
SDEAVRAIPKMYSTAPPGDFEEIPDDEIEE;

(SEQ ID NO: 15)
SDEAVRAIPKMYSQAPPGDFEEIPDDAIEE;

(SEQ ID NO: 16)
SDQGDVAEPKMYSTAPPFDFEAIPEEYLDDES;

(SEQ ID NO: 17)
SDQGDVAEPXMHSTAPPFDFEAIPEEYLDDES a variant of
SEQ ID NO: 2, wherein X is β-homoarginine;

(SEQ ID NO: 18)
CDEAVRAIPKMYSTAPPGDFEEIPDDAIEE a variant of SEQ
ID NO: 2;

(SEQ ID NO: 19)
SDEAVRAIPKMYSTAPPGDFEEIPDDAIEECA a variant of
SEQ ID NO: 2;

(SEQ ID NO: 20)
MYSTAPPGDFEEIPDDAIEEGCCC a variant of SEQ ID
NO: 2;

(SEQ ID NO: 21)
SDEAVRAIPKMYSTAPPGDFEEIPDDAIEEGCCC a variant of
SEQ ID NO: 2;

(SEQ ID NO: 22)
SGEDHTAVPKMSRKGLGGDFEDIPPEAYERALEAR;

(SEQ ID NO: 23)
ELESGDEDSEGGDSQSSPTESAAPRLHQREGGGGDFENVEYDQDQK;

(SEQ ID NO: 24)
SDVAPADYESDEGDNDGGHDGSEVAKPKMPRGNGGGGDFEEIPEVE;
and (SEQ ID NO: 25)
TGSDDDDEYDMYESDGDSNEGNDNDEFETAVPRLPNPNSGRDSEHI
PMPVN.
```

Another aspect of the invention provides an isolated thrombin inhibitor comprising an amino acid sequence according to any aspect of the invention for the prophylaxis or treatment of a disease associated with thrombus.

Another aspect of the invention provides a method of inhibiting thrombin activity, wherein the method comprises contacting thrombin with at least one thrombin inhibitor according to any aspect of the invention.

According to another aspect of the invention there is provided a use of a thrombin inhibitor according to any aspect of the invention for the preparation of a medicament for the prophylaxis and/or treatment of a disease associated with thrombus.

According to another aspect of the invention there is provided a method of prophylaxis and/or treatment of a disease associated with thrombus, comprising administering to a subject in need of such prophylaxis and/or treatment an efficacious amount of a thrombin inhibitor according to any aspect of the invention.

According to another aspect of the invention there is provided a method of detecting thrombin accumulation in a subject, comprising administering at least one inhibitor according to any aspect of the invention to a subject or to a tissue sample isolated from the subject, and detecting the presence of said at least one thrombin inhibitor bound to thrombin.

According to another aspect of the invention there is provided a pharmaceutical composition comprising an effective amount of at least one thrombin inhibitor according to any aspect of the invention.

According to another aspect of the invention there is provided an isolated nucleic acid molecule encoding a thrombin inhibitor according to any aspect of the invention. In a preferred embodiment the nucleic acid sequence encodes SEQ ID NO: 1 and is represented by

```
                                            (SEQ ID NO: 26)
TCGGGTGGCCATCAGACTGCTGTTCCGAAGATATCTAAGCAAGGCTTGG
GTGGAGACTTTGAAGAAATTCCAAGTGATGAAATAATCGAG.
```

According to another aspect of the invention there is provided a kit comprising at least one thrombus inhibitor as herein defined.

FIG. 10 shows the kinetics parameters of inhibition of avathrin variants. The residual thrombin amidolytic activities in presence of A. S12H, B. G2D, Q5D and C. K10R were measured at different concentrations of S2238 and the $K_i'$ (apparent $K_i$) were determined. Reactions were started with the addition of thrombin (0.81 nM). S12H, G2D, Q5D and K10R were tight binding thrombin inhibitors with $K_i$ values of 1.23±0.04 nM, 0.93±0.01 nM and 0.17±0.00 nM respectively. Each data point is the mean±S.D. of at least three independent experiments.

FIG. 11 shows Lineweaver-Burke plots of inhibition of thrombin by β-avathrin and S12A. The residual thrombin amidolytic activity in presence of β-avathrin (300 nM; A) and S12A (30 nM; B) was measured at various concentrations of S2238 (solid line, no inhibitor; dotted line, with inhibitor). Both β-avathrin and S12A are not tight binding inhibitors of thrombin as they are unable to inhibit thrombin at equimolar concentrations. The double reciprocal plots showed β-avathrin and S12A had $K_i$ values of 32.04±0.36 nM and 6.07±0.18 nM respectively. Each data point is the mean±S.D. of at least three independent experiments.

FIG. 12 shows a model of the crystal structure of avathrin thrombin complex. A. Overview of thrombin-avathrin complex. Avathrin is shown as sticks model (carbon; nitrogen; oxygen) along with surface representation of thrombin shown in light grey. Six residues $^{A}$($^{5}$QTAVPK$^{10}$) of SEQ ID NO: 1 and 10 residues $^{A}$($^{19}$DFEEIPSDEI$^{28}$) of SEQ ID NO: 1 were identified in the proximity of the thrombin active site and in the exosite-1 cleft. B. In a similar view as (A), electron density maps calculated for avathrin are shown. 2Fo-Fc map (gray, contoured at 1.0 sigma level) and Fo-FC map (positive map, contoured at 3.0 sigma, negative map, contoured at 3.0 sigma). C. Thrombin residues (light grey line) within a 4.5 Å radius of avathrin peptide N-terminal to scissile bond (sticks) are shown to depict interactions between them. D. Thrombin residues (light grey line) within a 4.5 Å radius of avathrin peptide (sticks) bound to the exosite-I are shown to depict interactions between them. E. In a similar view as (C), electron density maps calculated for avathrin are shown. 2Fo-Fc map (gray, contoured at 1.0 sigma level) and Fo-FC map (positive map, contoured at 3.0 sigma, negative map, contoured at 3.0 sigma). F. In a similar view as (D), electron density maps calculated for avathrin are shown. 2Fo-Fc map (gray, contoured at 1.0 sigma level) and Fo-FC map (positive map, contoured at 3.0 sigma, negative map, contoured at 3.0 sigma).

FIG. 13 shows the inhibition of clot bound thrombin by avathrin. The effect of avathrin on the amidolytic activity of clot-bound thrombin (0.81 nM) was measured using S2238 (100 μM). Avathrin inhibits clot bound thrombin in a dose-dependent manner with an $IC_{50}$ of 1.74±0.35 μM.

FIG. 14 shows the effect of avathrin on the time to occlusion in a ferric chloride-induced carotid artery thrombosis murine model compared to hirulog-1. Two doses (3 mg/kg and 10 mg/kg) of avathrin or hirulog-1 dissolved in 100 μl saline (0.9%) were injected intravenously through the tail vein of mice (n=6). Thrombosis was induced by placing a filter paper (2 mm×2 mm) saturated with 10% $FeCl_3$ on the carotid artery and the time to occlusion (TTO) after the $FeCl_3$-induced thrombosis was measured. Control animals were injected intravenously or peritoneally with 100 μl saline (n=6). From 7.24±1.46 min in control animals, the TTO increased to 15.03±3.23 min and 22.51±4.19 min in animals injected with 3 mg/kg and 10 mg/kg avathrin, respectively. In mice injected with 3 mg/kg and 10 mg/kg hirulog-1 the TTO were 9.76±3.15 min and 15.23±3.39 min, respectively. Significant differences between two groups were calculated using t-test (*P<0.001). Avathrin exhibits better efficacy compared to hirulog-1 in this model.

FIG. 15 shows an inhibition of thrombin amidolytic assay by peptides of variegin family. Selected peptides at different concentrations (0.0003-3000 nM) were tested for their abilities to inhibit thrombin. Ultravariegin, the peptide identified from the sialome of *Amblyomma variegatum* was the most potent peptide with an $IC_{50}$ of 0.26±0.008 nM. All other peptides had $IC_{50}$s in the range of 14 to 130 nM.

FIG. 16 shows thrombin inhibition by ultravariegin variants UV003 and UV004. A and C. Different concentrations (0.03 nM to 100 nM) were tested for their abilities to inhibit thrombin amidolytic activity and were compared with ultravariegin. UV003 and UV004 inhibited thrombin with $IC_{50}$ values of 0.60±0.20 nM and 0.46±0.08 nM respectively. B and D. Residual thrombin amidolytic activities in presence of UV003 and UV004 were measured at different concentrations of S2238 and their $K_i$ were determined. The $K_i$ of UV003 and UV004 were found to be 4.21±0.96 pM and 4.55±0.37 pM respectively.

FIG. 17 shows thrombin inhibition by ultravariegin variants UV005 and UV011. A and C. Different concentrations (0.03 nM to 100 nM) were tested for their abilities to inhibit thrombin amidolytic activity were compared with ultravariegin. UV005 and UV011 inhibited thrombin with $IC_{50}$ values of 0.91±0.47 pM and 1.66±0.77 nM. B and D.

Residual thrombin amidolytic activities in presence of UV005 and UV011 were measured at different concentrations of S2238 and their $K_i$ were determined. The $K_i$ of UV005 and UV011 were found to be 16.0±3.05 and 1387±230 pM.

Figure 18:
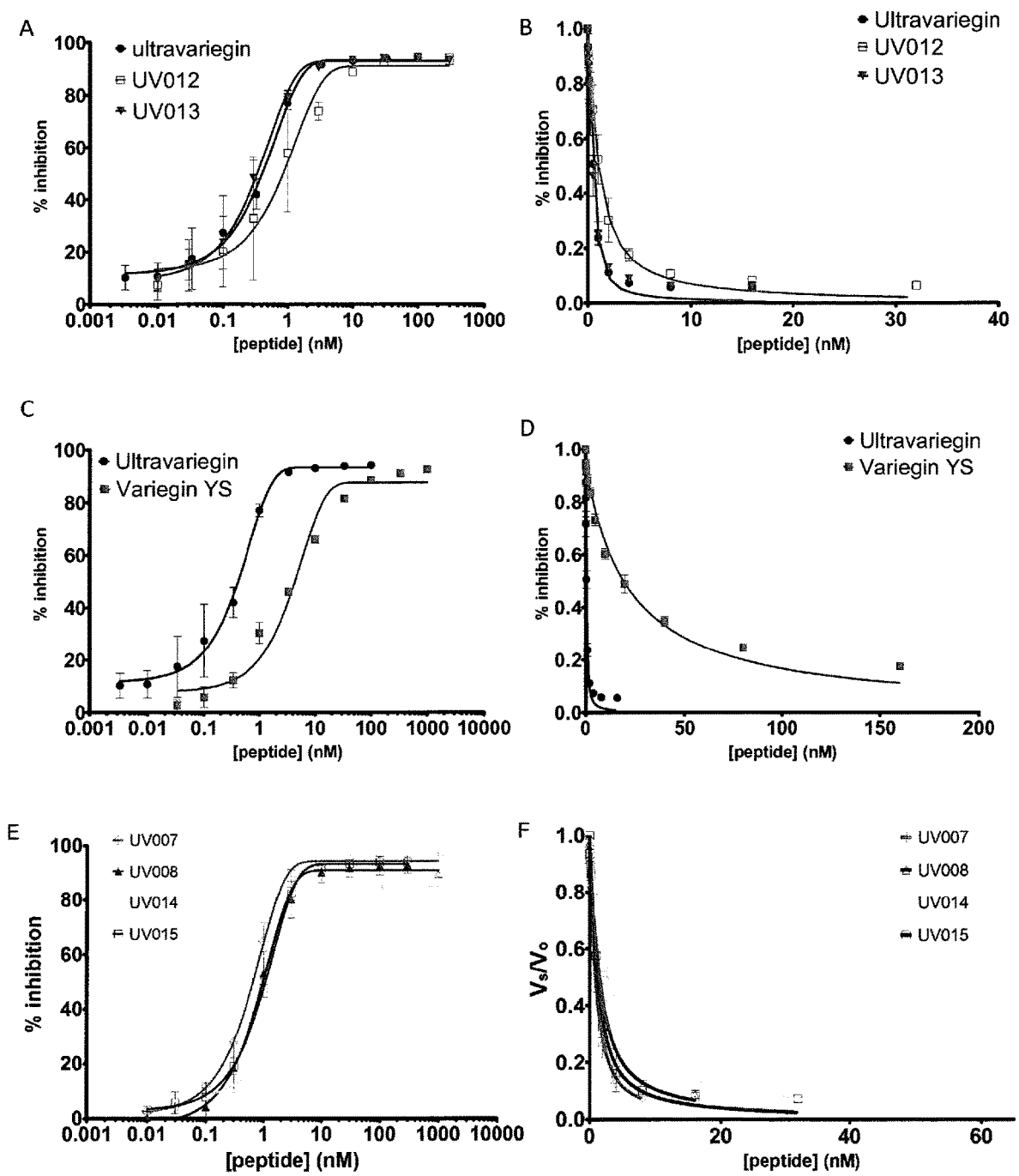

FIG. 18 shows thrombin inhibition by ultravariegin variants UV012, UV013, Variegin YS, UV007, UV008, UV014 and UV015. A, C and E. Different concentrations (0.003 nM to 3000 nM) were tested for their abilities to inhibit thrombin amidolytic activity were compared with ultravariegin. $IC_{50}$ values of different variants are listed in Table 5. B and D. Residual thrombin amidolytic activities in presence of UV012, UV013, Variegin YS, UV007, UV008, UV014 and UV015 for determination of their $K_i$ values by fitting data into tight-binding inhibitors equations. $K_i$ values of respective variants are listed in Table 4.

Figure 19:
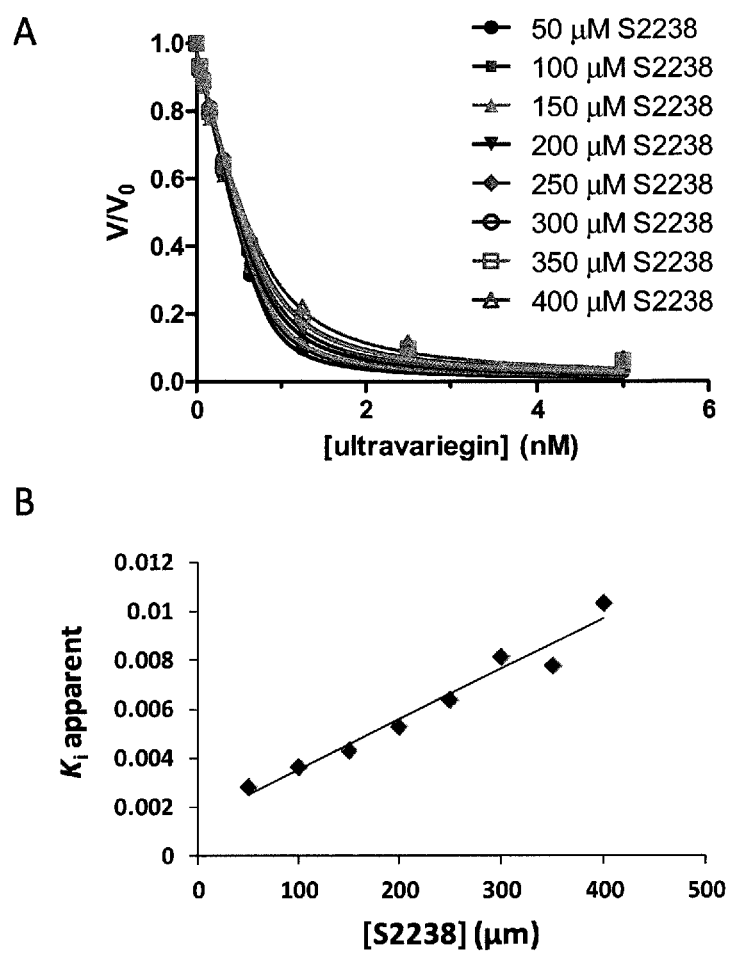

FIG. 19 shows the inhibitory constant $K_i$ of ultravariegin. $K_i$ of ultravariegin, the most potent member of the variegin family is shown as a representative. Ultravariegin is a tight binding inhibitor of thrombin. Different concentrations of ultravariegin were mixed with different concentrations of S2238 (50 µM, 100 µM, 150 µM, 200 µM, 250 µM, 300 µM, 350 µM and 400 µM and the $K_i'$ was determined. Reactions were started with the addition of thrombin (0.81 nM). Data were fitted to the Morrison equation using GraphPad prizm software (n=3, error bars represent S.D.). (B) Plot of $K_i'$ against substrate concentration increased linearly, indicating ultravariegin competitively inhibited thrombin amidolytic activity and the inhibitory constant $K_i$ was determined to be 4.4±0.35 pM (error bars represent S.D.).

Figure 20:
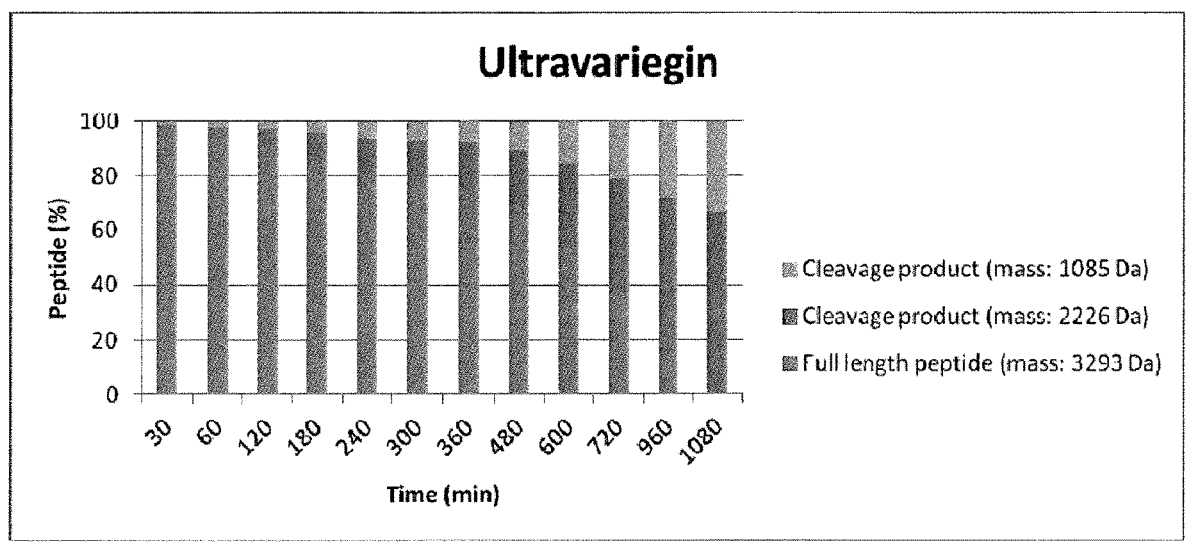

FIG. 20 shows cleavage of ultravariegin by thrombin. A time course analysis of ultravariegin incubated with thrombin indicated that ultravariegin was indeed cleaved by thrombin. A RP-HPLC separation of the reaction mixture incubated for different time points was carried out to separate and quantify the cleaved products. Quantification of cleaved products of ultravariegin was done by peak integration and calculating the area under the curve. With increasing times of incubation with thrombin, the amount of full length ultravariegin decreased and the amounts of the cleaved products corresponding to the cleavage of the Lys10-Met11 bond was observed. At 18 h, ultravariegin was completely cleaved and only peaks corresponding to the cleaved products could be observed.

Figure 21:
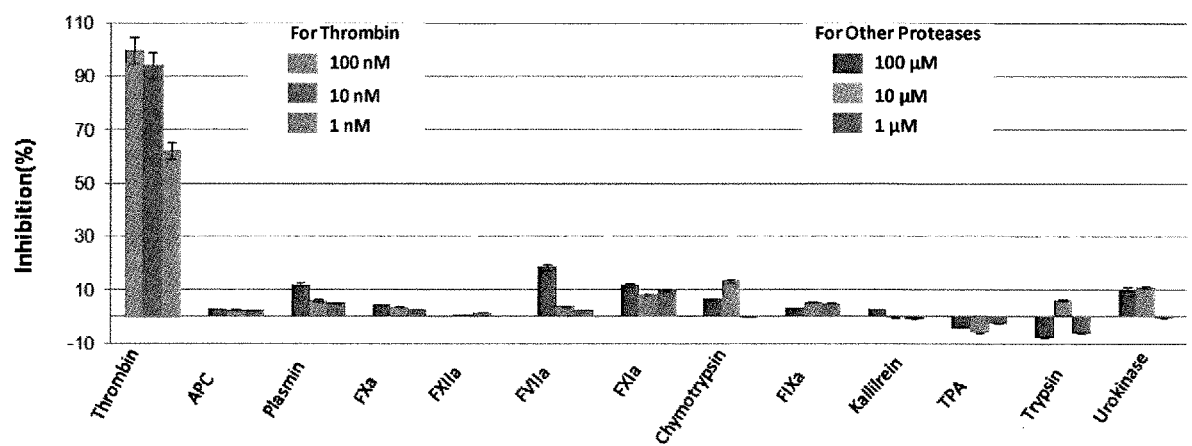

FIG. 21 shows serine protease selectivity of ultravariegin. Ultravariegin was screened against 13 serine proteases: fibrinolytic serine proteases (plasmin and TPA), anticoagulant serine protease (urokinase), procoagulant serine proteases (FXIIa, FXIa, FXa, FIXa, FVIIa, kallikrein, and thrombin), and classic serine proteases (trypsin and chymotrypsin). Thrombin was tested against three concentrations of ultravariegin: 100, 10 and 1 nM. For the other proteases, much higher concentrations of avathrin were used: 100, 10 and 1 µM.

Figure 22:
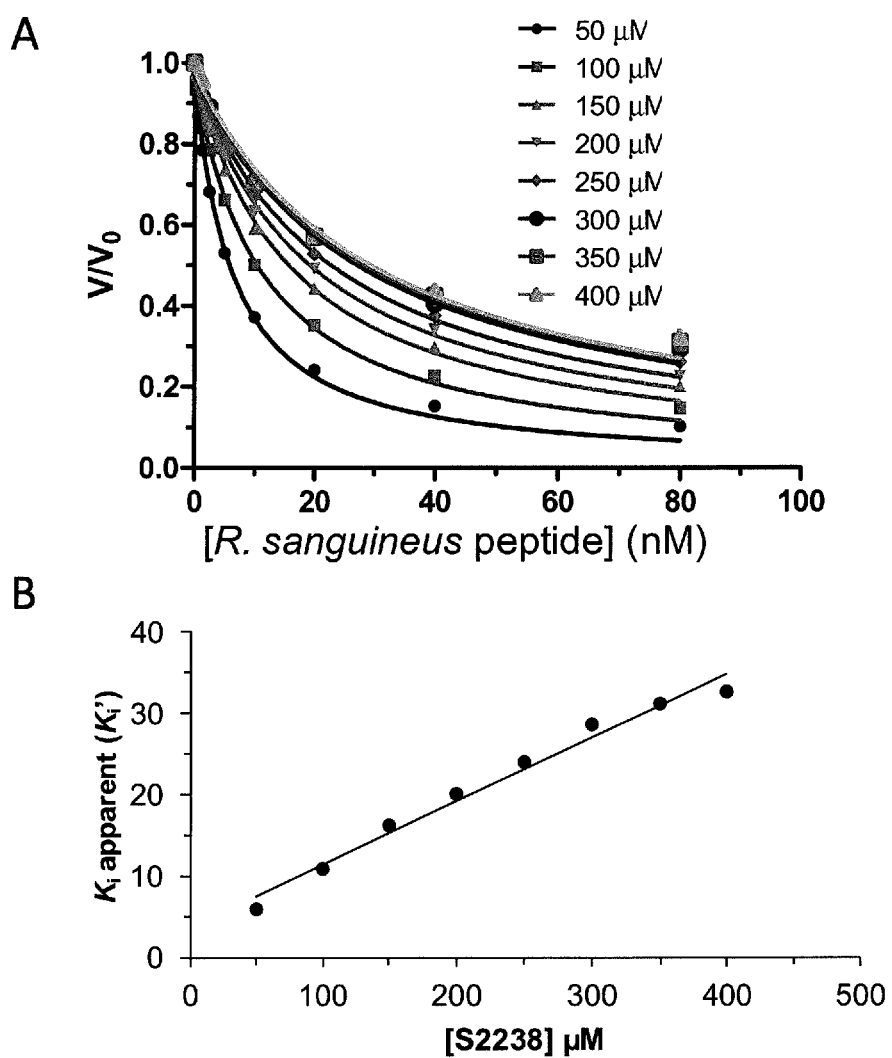

FIG. 22 shows the inhibitory constant $K_i$ of *Rhipicephalus sanguineus* peptide. $K_i'$ of *Rhipicephalus sanguineus* peptide was determined by mixing different concentrations of the peptide with different concentrations of S2238 (50 µM, 100 µM, 150 µM, 200 µM, 250 µM, 300 µM, 350 µM and 400 µM). Reactions were started with the addition of thrombin (0.81 nM). Data were fitted to the Morrison equation using GraphPad prizm software (n=3, error bars represent S.D.). (B) Plot of $K_i'$ against substrate concentration increased linearly, indicating the peptide competitively inhibited thrombin amidolytic activity and the inhibitory constant K was determined to be 8.79±0.65 nM (error bars represent S.D.).

Figure 23:
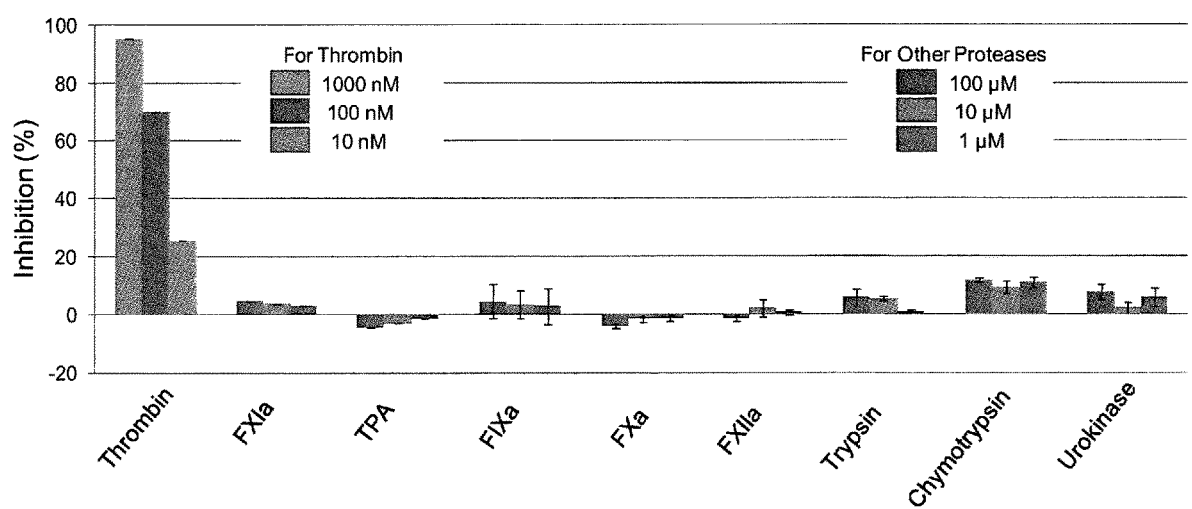

FIG. 23 shows serine protease selectivity of *Rhipicephalus sanguineus* peptide screened against 13 serine proteases: fibrinolytic serine proteases (plasmin and TPA), anticoagulant serine protease (urokinase), procoagulant serine proteases (FXIa, FXIa, FXa, FIXa, FVIIa, kallikrein, and thrombin),and classic serine proteases (trypsin and chymotrypsin). Thrombin was tested against three concentrations of the peptide: 1000, 100 and 10 nM. For the other proteases, much higher concentrations of the peptide were used: 100, 10 and 1 µM.

Figure 24:
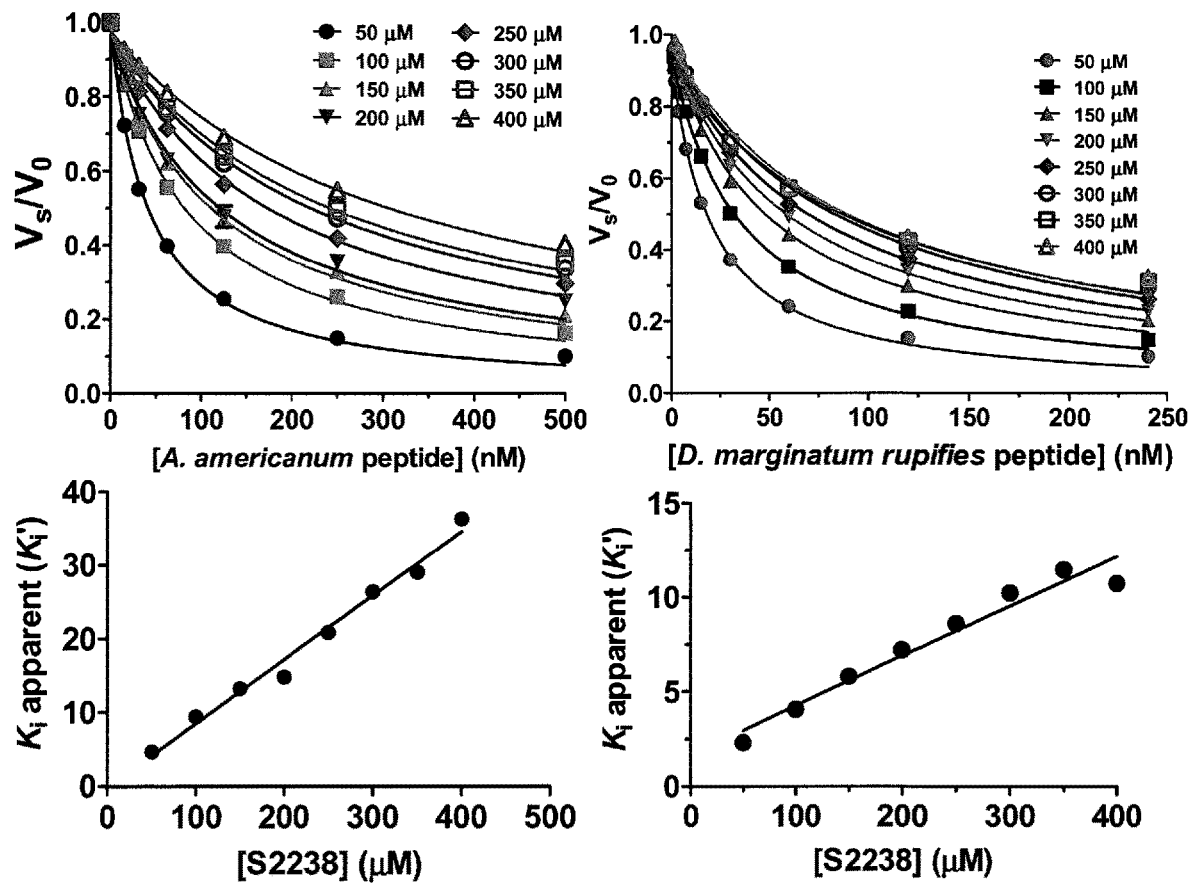

FIG. 24 shows the inhibitory constant $K_i$ of *Amblyomma americanum* and *Hyalomma marginatum rufipes* peptide. $K_i'$ of both peptides was determined by mixing different concentrations of the peptide with different concentrations of S2238 (50 µM, 100 µM, 150 µM, 200 µM, 250 µM, 300 µM, 350 µM and 400 µM). Reactions were started with the addition of thrombin (0.81 nM). Data were fitted to the Morrison equation using GraphPad prizm software (n=3, error bars represent S.D.). (B) Plot of $K_i'$ against substrate concentration increased linearly, indicating both peptides competitively inhibited thrombin amidolytic activity (error bars represent S.D.). The $K_i$ of the peptides from *Amblyomma americanum* and *Hyalomma marginatum rufipes* were determined to be 1.63±0.61 nM and 6.135±0.39 nM respectively.

Figure 25:
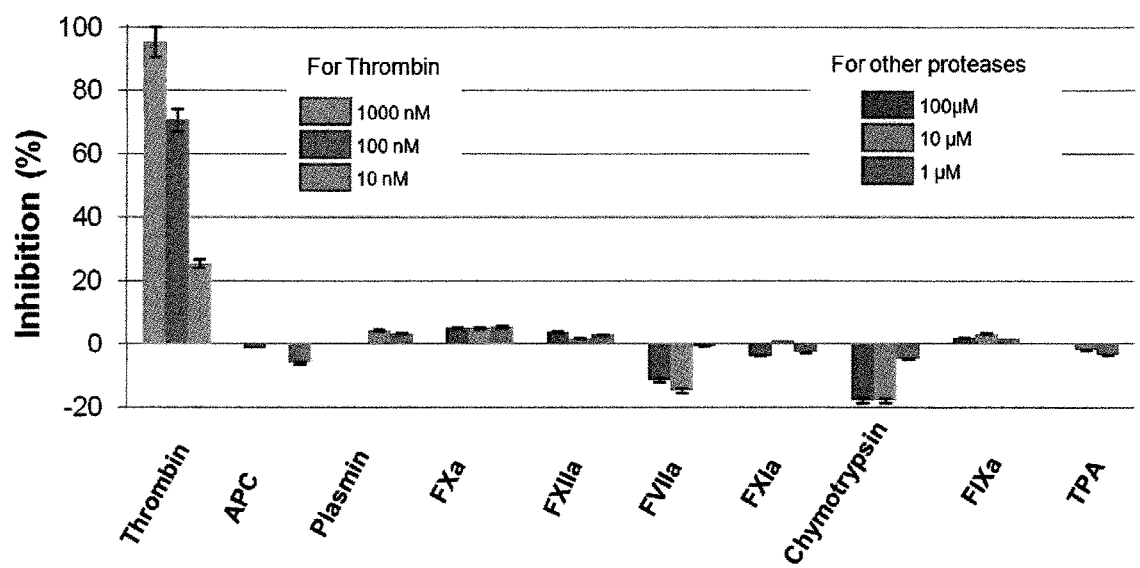
Figure 25:
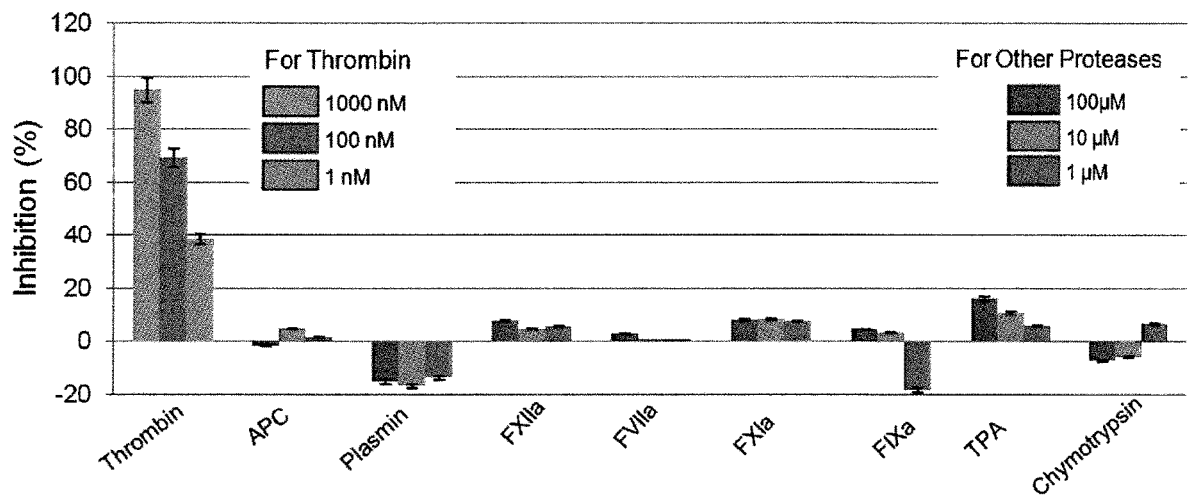

FIG. 25 Shows the serine protease selectivity of (A) *Amblyomma americanum* peptide and (B) *Hyalomma marginatum rufipes*. Both peptides was screened against fibrinolytic serine proteases (plasmin and TPA), anticoagulant serine protease (urokinase), procoagulant serine proteases (FXIIa, FXIa, FXa, FIXa, FVIIa, kallikrein, and thrombin), and classic serine proteases (trypsin and chymotrypsin). Thrombin was tested against three concentrations of the peptide: 1000, 100 and 10 nM. For the other proteases, much higher concentrations of the peptide were used: 100, 10 and 1 µM.

Figure 26:
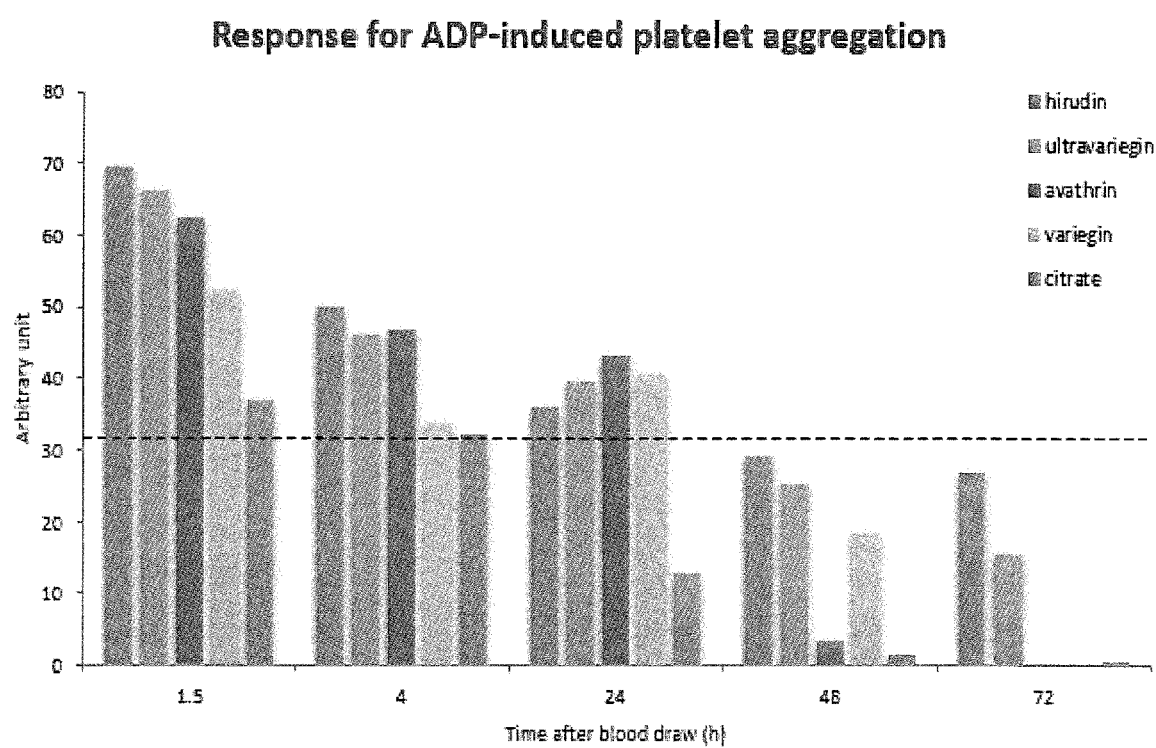

FIG. 26 shows the response for ADP-induced platelet aggregation in blood anticoagulated with different thrombin inhibitors hirudin, ultravariegin, avathrin, variegin and citrate, measured at different time points after the blood draw.

Figure 27:
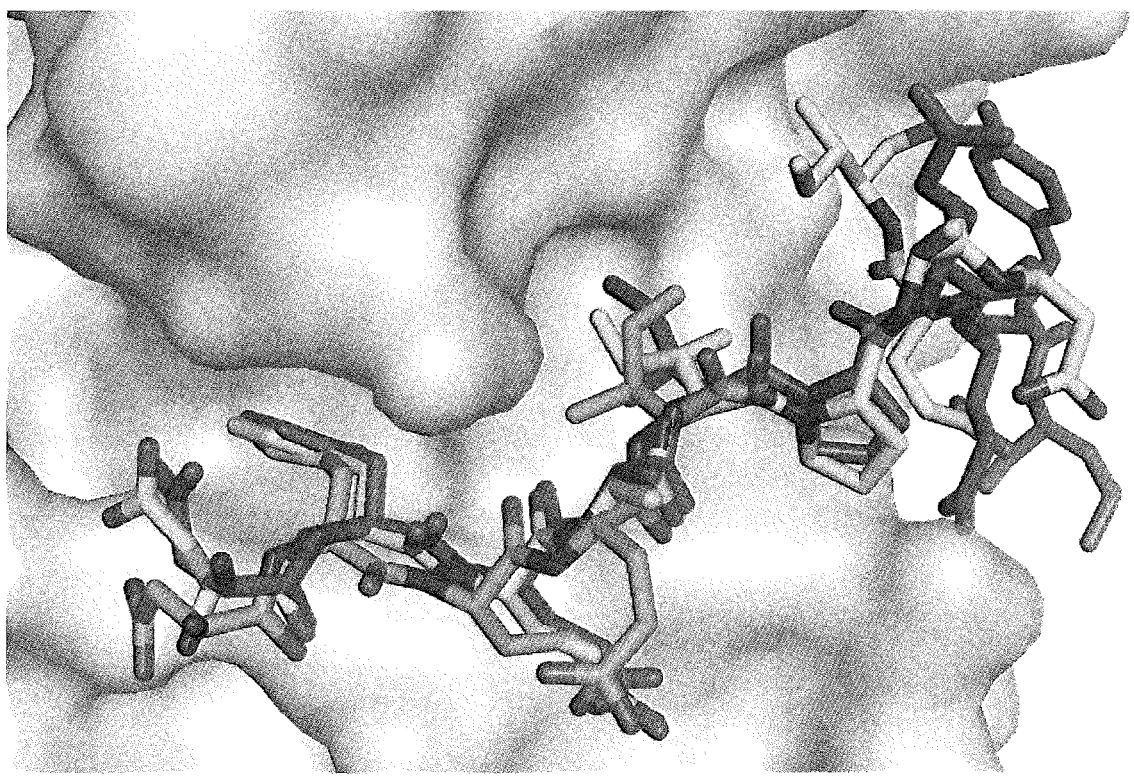

FIG. 27 shows the interactions of avathrin and other inhibitors with thrombin exosite. Surface representation of thrombin exosite is shown in light grey; thrombin inhibitors are shown in sticks models. C-terminal segments of avathrin, variegin and hirulog-1 are overlaid.

FIG. 28 shows a sequence alignment of avathrin with variegin and related peptides identified from transcriptomes of salivary glands of *Amblyomma variegatum*, *Amblyomma americanum* and *Amblyomma cajannense*. Each transcript codes for a precursor protein that is post-translationally cleaved into three to five mature peptides. Only one representative peptide sequence from each transcript is shown.

Bibliographic references mentioned in the present specification are for convenience listed in the form of a list of references and added at the end of the examples. The whole content of such bibliographic references is herein incorporated by reference.

DETAILED DESCRIPTION OF THE INVENTION

Definitions

For convenience, certain terms employed in the specification, examples and appended claims are collected here.

The term "comprising" is herein defined to be that where the various components, ingredients, or steps, can be conjointly employed in practicing the present invention. Accordingly, the term "comprising" encompasses the more restrictive terms "consisting essentially of" and "consisting of."

The term "isolated" is herein defined as a biological component (such as a nucleic acid, peptide or protein) that has been substantially separated, produced apart from, or purified away from other biological components in the cell of the organism in which the component naturally occurs, i.e., other chromosomal and extra-chromosomal DNA and RNA, and proteins. Nucleic acids, peptides and proteins which have been isolated thus include nucleic acids and proteins purified by standard purification methods. The term also embraces nucleic acids, peptides and proteins prepared by recombinant expression in a host cell as well as chemically synthesized nucleic acids.

The term "variant" is herein defined as one which has at least one nucleotide sequence that varies from a reference sequence via substitution, deletion or addition of at least one nucleic acid, but encodes an amino acid sequence that retains the ability to recognize, bind and inhibit thrombin. The term 'variant' also applies to an amino acid sequence that varies from at least one reference sequence via substitution, deletion or addition of at least one amino acid, but retains the ability to recognize, bind and inhibit thrombin. In particular, the variants may be naturally occurring or may be recombinant or synthetically produced. More in particular, the variant may be of at least 30%, at least 40%, at least 50%, at least 60%, at least 70%, at least 80%, at least 90%, or at least 95% sequence identity to the reference sequences. For example, the AvathrinK10R amino acid sequence set forth in SEQ ID NO: 7 was created by substituting amino acids in the Avathrin amino acid sequence set forth in SEQ ID NO: 1 and may be considered a variant of SEQ ID NO: 1. The term "variant" may include peptide inhibitors of thrombin that have "conservative" changes, wherein a substituted amino acid has similar structural or chemical properties (e.g., replacement of leucine with isoleucine). More rarely, a variant may have "non-conservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, DNASTAR® software (DNASTAR, Inc. Madison, Wis., USA). Another form of variant includes substitution of an amino acid with a modified amino acid, such as beta-homoarginine in β-ultravariegin (SDEAVRAIPXMYSTAPPGDFEEIPDDAIEE) set forth as "X" in SEQ ID NO: 9. For the purpose of the sequence listing, the beta-homoarginine will be represented by "X" or "Xaa".

The term "fragment" as used herein, refers to an amino acid sequence that is altered by one or more amino acids, but retains the ability to recognize and bind the same conformational epitope on thrombin as the reference sequence. For example, the QTAVPKISKQGLGGDFEEIPSDEIIE (QT26) amino acid sequence set forth in SEQ ID NO: 3 is shorter than the Avathrin sequence set forth in SEQ ID NO: 1 (SGGHQTAVPKISKQGLGGDFEEIPSDEIIE) and may be considered a fragment of SEQ ID NO: 1 because it retains the ability to recognize, bind and inhibit thrombin. Likewise, the IS20 (ISKQGLGGDFEEIPSDEIIE) amino acid sequence set forth in SEQ ID NO: 4 is shorter than the Avathrin sequence set forth in SEQ ID NO: 1 (SGGHQTAVPKISKQGLGGDFEEIPSDEIIE) and may be considered a fragment of SEQ ID NO: 1 because it retains the ability to recognize, bind and inhibit thrombin.

The term "sample," as used herein, is used in its broadest sense. A biological sample suspected of containing thrombin may comprise a bodily fluid or a tissue.

The term "treatment", as used in the context of the invention refers to prophylactic, ameliorating, therapeutic or curative treatment.

The term "subject" is herein defined as vertebrate, particularly mammal, more particularly human. For purposes of research, the subject may particularly be at least one animal model, e.g., a mouse, rat and the like. In particular, for treatment of thrombus and/or thrombus-linked diseases, the subject may be a human.

The present invention, in one aspect provides an isolated thrombin inhibitor comprising an amino acid sequence selected from the group comprising SGGHQTAVPKISKQGLGGDFEEIPSDEIIE (SEQ ID NO: 1), a variant or fragment thereof, SDEAVRAIPKMYSTAPPGDFEEIPDDAIEE (SEQ ID NO: 2), a variant or fragment thereof, SEQ ID NO: 22, a variant or fragment thereof, SEQ ID NO: 23, a variant or fragment thereof, SEQ ID NO: 24, a variant or fragment thereof and SEQ ID NO: 25, a variant or fragment thereof. It would be understood that these sequences, as herein disclosed, may be altered and still retain an ability to inhibit thrombin activity.

For example, it was found that residues 7(A), 9(P), 10(K), 19-21(DFE), 23( ) and 24(P) of SEQ ID NO: 1 and SEQ ID NO: 2 are important for thrombin inhibitory activity because they are the least tolerant to changes. If most of these key residues are retained, we have produced peptide variants with as low as 30% identity that retains thrombin inhibitory activity.

In a preferred embodiment the isolated thrombin inhibitor comprises an amino acid sequence having at least 30%, at least 40%, at least 50%, at least 60%, at least 70%, at least 80%, at least 90%, or more preferably at least 95% sequence identity to SEQ ID NO: 1, SEQ ID NO: 2, SEQ ID NO: 22, SEQ ID NO: 23, SEQ ID NO: 24, or SEQ ID NO: 25. More preferably, the isolated thrombin inhibitor comprises an amino acid sequence having at least 60%, at least 70%, at least 80%, at least 90%, or more preferably at least 95% sequence identity to SEQ ID NO: 1 or SEQ ID NO: 2.

In a preferred embodiment the isolated thrombin inhibitor amino acid sequence is selected from the group comprising;

(SEQ ID NO: 3)
QTAVPKISKQGLGGDFEEIPSDEIIE a fragment of SEQ ID NO: 1;

(SEQ ID NO: 4)
ISKQGLGGDFEEIPSDEIIE a fragment of SEQ ID NO: 1;

(SEQ ID NO: 5)
SGGHQTAVPKIAKQGLGGDFEEIPSDEIIE a 512A variant of SEQ ID NO: 1;

(SEQ ID NO: 6)
SGGHQTAVPKIHKQGLGGDFEEIPSDEIIE a 512H variant of SEQ ID NO: 1;

(SEQ ID NO: 7)
SGGHQTAVPRISKQGLGGDFEEIPSDEIIE a K10R variant of SEQ ID NO: 1;

(SEQ ID NO: 8)
SGGHQTAVPXISKQGLGGDFEEIPSDEIIE a β-homoarginine variant of SEQ ID NO: 1;

-continued

```
                                        (SEQ ID NO: 9)
SDEAVRAIPXMYSTAPPGDFEEIPDDAIEE a β-homoarginine
variant of SEQ ID NO: 2.

(SEQ ID NO: 10)
SDQGDVAIPKMYSTAPPGDFEEIPDDAIEE a variant of SEQ
ID NO: 2;

(SEQ ID NO: 11)
SDEAVRAEPKMHKTAPPGDFEEIPDDAIEE a variant of SEQ
ID NO: 2;

(SEQ ID NO: 12)
SDEAVRAIPKMYSTAPPGDFEEIPEEYLDDES a variant of
SEQ ID NO: 2;

(SEQ ID NO: 13)
MYSTAPPGDFEEIPDDAIEE a variant of SEQ ID NO: 2;

(SEQ ID NO: 14)
SDEAVRAIPKMYSTAPPGDFEEIPDDEIEE a variant of SEQ
ID NO: 2;

(SEQ ID NO: 15)
SDEAVRAIPKMYSQAPPGDFEEIPDDAIEE a variant of SEQ
ID NO: 2;

(SEQ ID NO: 16)
SDQGDVAEPKMYSTAPPFDFEAIPEEYLDDES a variant of SEQ
ID NO: 2;

(SEQ ID NO: 17)
SDQGDVAEPXMHSTAPPFDFEAIPEEYLDDES a variant of SEQ
ID NO: 2;

(SEQ ID NO: 18)
CDEAVRAIPKMYSTAPPGDFEEIPDDAIEE a variant of SEQ
ID NO: 2;

(SEQ ID NO: 19)
SDEAVRAIPKMYSTAPPGDFEEIPDDAIEECA a variant of SEQ
ID NO: 2;

(SEQ ID NO: 20)
MYSTAPPGDFEEIPDDAIEEGCCC a variant of SEQ ID
NO: 2;

(SEQ ID NO: 21)
SDEAVRAIPKMYSTAPPGDFEEIPDDAIEEGCCC a variant of
SEQ ID NO: 2;

(SEQ ID NO: 22)
SGEDHTAVPKMSRKGLGGDFEDIPPEAYERALEAR;

(SEQ ID NO: 23)
ELESGDEDSEGGDSQSSPTESAAPRLHQREGGGGDFENVEYDQDQK;

(SEQ ID NO: 24)
SDVAPADYESDEGDNDGGHDGSEVAKPKMPRGNGGGGDFEEIPEVE;
and (SEQ ID NO: 25)
TGSDDDDEYDMYESDGDSNEGNDNDEFETAVPRLPNPNSGRDSEHIP
MPVN;
```

Preferably said inhibitor has an amino acid sequence selected from the group consisting of SEQ ID NO: 2, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

In another preferred embodiment, said thrombin inhibitor inhibits thrombin fibrinogenolytic activity and/or inhibits thrombin amidolytic activity.

In another preferred embodiment, the thrombin inhibitor has an $IC_{50}$ of less than 400 nM, preferably less than 300 nM, less than 200 nM, less than 100 Nm, less than 50 nm, less than 10 nM, preferably less than 9 nM, less than 8 nM, less than 7 nM, less than 6 nM, less than 5 nM, less than 4 nM, less than 3 nM, less than 2 nM or less than 1 nM when assessed in an amidolytic assay. More preferably, the $IC_{50}$ is less than 2 nM. It is intended that $IC_{50}$ values between those specifically recited are within the scope of the invention.

In another preferred embodiment, the thrombin inhibitor has a $K_i$ of less than 6000 nM, preferably less than 2000, less than 500, less than 400 nM, less than 300 nM, less than 200 nM, less than 100 Nm, less than 50 nm, less than 10 nM, preferably less than 9 nM, less than 8 nM, less than 7 nM, less than 6 nM, less than 5 nM, less than 4 nM, less than 3 nM, less than 2 nM or less than 1 nM when assessed in an amidolytic assay. More preferably, the $K_i$ is less than 2 nM. It is intended that Ki values between those specifically recited are within the scope of the invention.

Another aspect of the invention provides an isolated thrombin inhibitor comprising an amino acid sequence according to any aspect of the invention for the prophylaxis or treatment of a disease associated with thrombin activity.

Another aspect of the invention provides a method of inhibiting thrombin activity, wherein the method comprises contacting thrombin with at least one thrombin inhibitor according to any aspect of the invention. In a preferred embodiment, the at least one thrombin inhibitor is present as an anticlotting agent in blood collection tubes, or as a surface coating material on medical devices such as stents, catheters and other medical tubing.

According to another aspect of the invention there is provided a use of a thrombin inhibitor according to any aspect of the invention for the preparation of a medicament for the prophylaxis and/or treatment of a disease associated with thrombus. In a preferred embodiment, the disease associated with thrombus is selected from arterial and venous thrombosis causing heart attacks, stroke and embolism; for anticoagulation during unstable angina, coronary angioplasty, percutaneous coronary intervention and heart surgery.

Suitable methods for administering a therapeutic composition in accordance with the methods of the present invention include, but are not limited to, systemic administration, parenteral administration (including intravascular, intramuscular, intraarterial administration), oral delivery, topical administration, buccal delivery, rectal delivery, vaginal delivery, subcutaneous administration, intraperitoneal administration, surgical implantation, local injection, and hyper-velocity injection/bombardment. Where applicable, continuous infusion can enhance drug accumulation at a target site (see, e.g., U.S. Pat. No. 6,180,082).

Regardless of the route of administration, the peptides of the present invention are typically administered in amount effective to achieve the desired response. As used herein, the terms "effective amount" and "therapeutically effective amount" refer to an amount of the therapeutic composition (e.g., a composition comprising a thrombin inhibitor polypeptide, and a pharmaceutically vehicle, carrier, or excipient) sufficient to produce a measurable biological response (e.g., a decrease in the amount of a thrombus or thrombus-related disease). Actual dosage levels of active ingredients in a therapeutic composition of the present invention can be varied so as to administer an amount of the active polypeptide(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated.

Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902 and 5,234,933; PCT International Publication No. WO 93/25521; Berkow, et al., (1997) The Merck Manual of Medical Information, Home ed. Merck Research Laboratories, Whitehouse Station, N.J.; Goodman, et al., (2006) Goodman & Gilman's the Pharmacological Basis of Therapeutics, 11th ed. McGraw-Hill Health Professions Division, New York.

According to another aspect of the invention there is provided a method of prophylaxis and/or treatment of a disease associated with thrombin activity, comprising administering to a subject in need of such prophylaxis and/or treatment an efficacious amount of a thrombin inhibitor according to any aspect of the invention. In a preferred embodiment, the disease associated with thrombus is selected from arterial and venous thrombosis causing heart attacks, stroke and embolism; for anticoagulation during unstable angina, coronary angioplasty, percutaneous coronary intervention and heart surgery.

The thrombin inhibitors of the invention may also be used topically to treat, for example, bruises with or without hematoma. The peptide inhibitors of the invention may be administered in a cream in a similar regimen as previously trialed with Hirudin, in which 280 UI/100 g was applied to unilateral acute musculoskeletal injuries (bruises) in 3-4 daily applications for 5 days [Stamenova P K., et al, *Eur Rev Med Pharmacol Sci.* 5(2):37-42 (2001)]. Thrombin inhibitors have also been formulated as topical application (r-hirudin 1120 IU/40 g; MINAPHARM Pharmaceuticals, Cairo, Egypt) to treat AV shunt thrombosis, contusions, distortions, muscular tears, traumatic hematomas, edema, erythema, varicosities, periphlebitis and anal periphlebitis with haemorrhoids especially those associated with thrombo-embolic complications [see Thrombexx® at minapharm.com]. The molecules of the present invention are less than half the size of hirudin, which should increase the penetration of the active ingredient (ie. thrombin inhibitor) across the skin barrier when applied topically.

According to another aspect of the invention there is provided a method of detecting thrombin accumulation in a subject, comprising administering at least one inhibitor according to any aspect of the invention to a subject or to a tissue sample isolated from the subject, and detecting the presence of said at least one thrombin inhibitor bound to thrombin.

In a preferred embodiment there is provided a method of detecting thrombin accumulation in a subject, said method comprising:

a. obtaining a tissue sample from a patient; and
b. detecting whether thrombin has accumulated in the sample by contacting the sample with at least one inhibitor according to any aspect of the invention and detecting binding between thrombin and the at least one thrombin inhibitor.

Preferably, the thrombin inhibitor comprises an amino acid sequence selected from the group comprising SGGHQTAVPKISKQGLGGDFEEIPSDEIIE (SEQ ID NO: 1), a variant or fragment thereof, and SDEAVRAIPKMYSTAPPGDFEEIPDDAIEE (SEQ ID NO: 2), a variant or fragment thereof.

In another preferred embodiment of the method, the thrombin inhibitor comprises an amino acid sequence selected from the group comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24 and SEQ ID NO: 25.

Preferably said inhibitor has an amino acid sequence selected from the group consisting of SEQ ID NO: 2, SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16, SEQ ID NO: 17, SEQ ID NO: 18, SEQ ID NO: 19, SEQ ID NO: 20 and SEQ ID NO: 21.

According to another aspect of the invention there is provided a method of diagnosing a disease or condition associated with thrombus, comprising administering at least one inhibitor according to any aspect of the invention to a subject or to a tissue sample isolated from said subject, and detecting the presence of said thrombin inhibitor bound to thrombin wherein the detection of an elevated level of said inhibitor bound to thrombin compared to a level of inhibitor bound to a normal thrombin level is indicative of said disease or condition.

In another preferred embodiment of the method, the thrombin inhibitor comprises an amino acid sequence selected from the group comprising SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO:11, SEQ ID NO:12, SEQ ID NO:13, SEQ ID NO:14, SEQ ID NO:15, SEQ ID NO:16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24 and SEQ ID NO: 25.

Preferably said inhibitor has an amino acid sequence selected from the group consisting of SEQ ID NO: 2, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 and SEQ ID NO: 21.

According to another aspect of the invention there is provided a pharmaceutical composition comprising an effective amount of at least one thrombin inhibitor according to any aspect of the invention.

According to another aspect of the invention there is provided an isolated nucleic acid molecule encoding a thrombin inhibitor according to any aspect of the invention. In a preferred embodiment the nucleic acid sequence encodes SEQ ID NO: 1 and is represented by;

TCGGGTGGCCATCAGACTGCTGTTCCGAAGATATCTAAGCAAGGCTTGGGTGGAG ACTTTGAAGAAATTCCAAGTGATGAAATAATCGAG (SEQ ID NO: 26).

In another preferred embodiment, the isolated nucleic acid molecule encodes a thrombin inhibitor comprising an amino acid sequence selected from the group comprising SEQ ID NO: 1 and SEQ ID NO: 2, variants or fragments thereof.

In a preferred embodiment, the isolated nucleic molecule encodes SEQ ID NO: 2 a fragment or variant thereof and may be obtained by modifying the nucleic acid sequence represented by;

TCAGACGAAGCTGTCAGGGCGATTCCCAAGATGTACTCGACTGCCCCACCGGGAG
ATTTCGAAACAATCCCTGACGACGCTATTGAGGAG (SEQ ID NO: 27) a fragment or variant thereof. Preferably the nucleotide sequence of SEQ ID NO: 27 is altered, by replacing the codon encoding Thr22 with a suitable codon to encode Glu22, to produce the peptide of SEQ ID NO: 2. It would be understood that the native nucleotide sequence (SEQ ID NO: 27) encodes a suitable thrombin inhibitor according to the invention.

In a preferred embodiment, the nucleic acid has a sequence represented by SEQ ID NO: 26 or SEQ ID NO: 27, a variant or derivative thereof.

According to another aspect of the invention there is provided a vector comprising a nucleic acid molecule according to the invention as herein described.

According to another aspect of the invention there is provided a host cell comprising a nucleic acid molecule or a vector according to any aspect of the invention. The host cell may be prokaryotic or eukaryotic but is preferably eukaryotic.

According to another aspect of the invention there is provided a kit to prevent or treat a disease or condition associated with thrombus comprising at least one thrombus inhibitor or medicament according to any aspect of the invention. The kit may comprise a medical device, such as a stent, catheter or other form of tube coated in the thrombus inhibitor of the invention.

Having now generally described the invention, the same will be more readily understood through reference to the following examples which are provided by way of illustration, and are not intended to be limiting of the present invention. The methods, techniques and chemicals are as described in the references given or from protocols in standard biotechnology and molecular biology text books.

EXAMPLES

Materials and Methods

Kallikrein, human fibrinogen, and bovine trypsin were purchased from Merck. Chemicals Ltd. (Nottingham, UK). Bovine chymotrypsin, ferric chloride hexahydrate and bovine serum albumin were purchased from Sigma-Aldrich (St. Louis, Mo., USA). All other serine proteases were from Hematologic Technologies, Inc. (Essex Junction, Vt., USA). Recombinant thrombin was a gift from the Chemo-Sero-Therapeutic Research Institute (Kaketsuken, Japan). Chromogenic substrates were purchased from Chromogenix and Spectrozyme FIXa was from American Diagnostica. All other chemicals and reagents used were of analytical grade.
Peptide Synthesis and Purification All peptides were synthesized using solid-phase peptide synthesis on an Intavis MultiPep RSi peptide synthesizer. Intavis Bioanalytical Instruments, Cologne, Germany) and cleaved from resin as described previously [[Koh C Y, et al., *J Biol Chem* 282: 29101-13 (2007)]. Crude peptides were purified using reverse-phase HPLC on an AKTA purifier from GE Healthcare (Uppsala, Sweden) with a Jupiter Proteo (5 µm, 250 mm×10 mm, 90 Å) column. The purity and mass of all peptides were determined by ESI-MS using an LCQ Fleet Ion Trap MS from Thermo Fisher Scientific (Waltham, Mass., USA).
CD Spectroscopy Far-UV CD spectra (260-190 nm) of avathrin, QT26 and IS20 dissolved in 10 mM sodium phosphate buffer (pH 7.4) were measured using a Jasco™ J-810 spetropolarimeter (Easton, Md.). All measurements were carried out at room temperature using a 0.1-cm path length cuvette with a scan speed of 50 nm/min, a bandwidth of 2 nm and a resolution of 0.2 nm.

Figure 5:
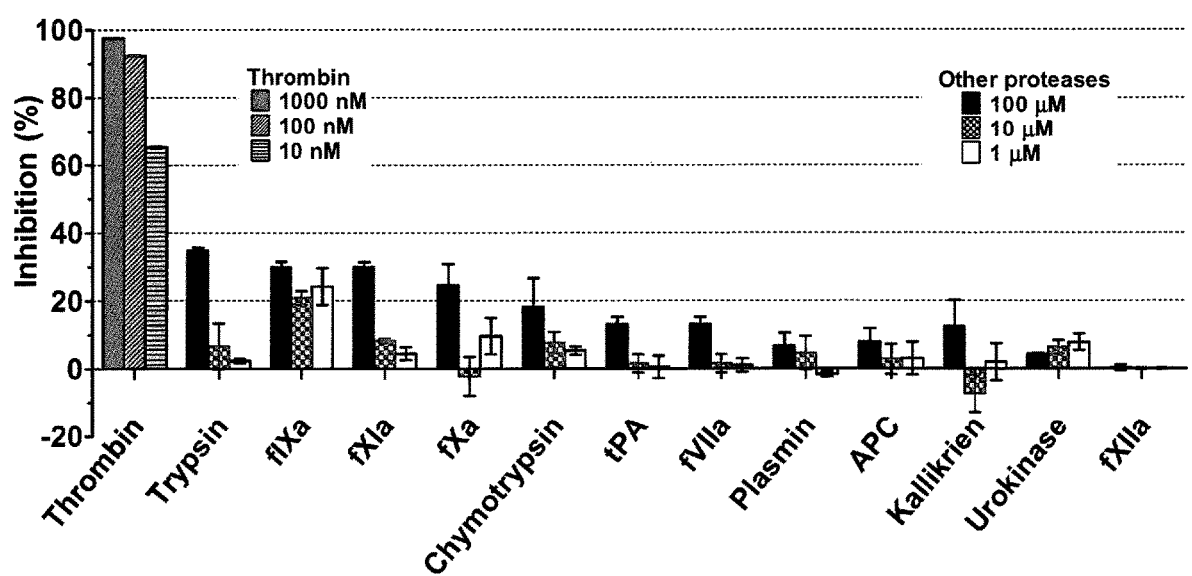
FIG. 5 shows serine protease selectivity of avathrin. Avathrin was screened for its selectivity against 13 serine proteases including procoagulant, anticoagulant, fibrinolytic and classical serine proteases (thrombin, trypsin, fIXa, fXIa, fXa, chymotrypsin, tPA, fVIIa, plasmin, APC, kallikrien, urokinase and fXIIa). The final concentrations of proteases and substrates used for the amidolytic assays are given in parentheses in nM and µM, respectively, unless mentioned otherwise: α-thrombin/S2238 (0.81/100), trypsin/S2222 (0.87/100), fIXa//Spectrozyme® fIXa (333/0.4), fXIa/S2366 (0.125/1000), fXa/S2765 (0.24/650), chymotrypsin/S2586 (1.2/0.67), tPA/S2288 (36.9/1000), fVIIa/S2288 (460/1200), plasmin/S2251 (3.61/1200), APC/S2366 (2.74/600), kallikrein/S2302 (0.93/1100), urokinase/S2444 (32 U/ml/650), fXIIa/S2302 (20/1000). Activity of thrombin was tested at lower concentrations of avathrin (1000 nM, 100 nM and 10 nM) while the other proteases were tested at much higher concentrations of avathrin (100 µM, 10 µM and 1 µM). Each data point is the mean±S.D. of at least three independent experiments.

Inhibition of Amidolytic and Fibrinogenolytic Activities of Thrombin and Protease Activities Thrombin amidolytic activity assays for all peptides were performed in 96-wells microtiter plates in 50 mM Tris buffer (pH 7.4) containing 100 mM NaCl and 1 mg/ml bovine serum albumin. Typically, 100 µl of peptide and 100 µl of thrombin were pre-incubated for different durations before 100 µl of S2238 was added to the reaction wells. The rates of formation of p-nitroaniline were followed by measuring the absorbance at 405 nm for 10 min with a Tecan InfinitePro M200 microplate reader from Tecan (Männedorf, Switzerland). Dose-response curves were fitted using the GraphPad Prizm software (San Diego, Calif., USA) to calculate IC50 values and Hill coefficients. To measure the inhibitory constants, different concentrations of S2238 were used and the residual velocities were determined using the Morrison's tight binding equation. Inhibition of thrombin fibrinogenolytic activity of peptides were tested by measuring absorbance at 650 nm using a Sunrise microplate reader from Tecan (Männedorf, Switzerland) as described previously [Koh C Y, et al., *J Biol Chem* 282: 29101-13 (2007)]. The selectivity of avathrin was examined against 13 serine proteases (FIG. 5). Effects of avathrin on the amidolytic activities of these serine proteases were determined using respective chromogenic substrates. Cleavage of avathrin by thrombin. Avathrin (150 µM) was incubated with thrombin (5 µM), in 50 mM Tris buffer (pH 7.4) containing 150 mM NaCl and 1 mg/ml BSA. After different incubation times, reactions were quenched with 1% TFA (pH 1.8) and loaded onto a Jupiter Proteo column (4 µm, 90 Å, 100×1.0 mm) attached to a Dionex nano-HPLC system from Thermo Fisher Scientific (Waltham, Mass., USA) and eluted using an acetonitrile gradient with 0.05% TFA and 99.95% MilliQ water as eluent A and 0.05% TFA, 19.95% MilliQ water and 80% ACN as eluent B. Masses of all peaks were measured to identify cleavage products, which were subsequently quantified by integrating the peaks and calculating the area under the curves. To measure the effect of different pre-incubation times on the thrombin inhibitory activity, amidolytic assays were performed for various incubation times (up to 36 h).
X-Ray Crystallography Recombinant α-thrombin (in 150 mM NaCl) was desalted using 3000 MWCO spin filters in 20 mM NH$_4$HCO$_3$ and lyophilized before crystallization. The crystallization conditions for other inhibitor complexes, thrombin with variegin, hirugen and hirulog, were used and optimized further [Koh C Y, et al., *PLoS One* 2011; 6; Skrzypczak-Jankun E, et al., *J Mol Biol* 221: 1379-93 (1991)]. Avathrin (81.7 µM) was dissolved in 50 mM HEPES buffer (pH 7.4) containing 375 mM NaCl. Thrombin was dissolved in the avathrin solution to a final concentration of 54.5 µM. Crystallization was achieved using the hanging drop vapor diffusion method. Typically, 1 µl of mixture containing avathrin and thrombin was mixed with 1 µl of precipitant (100 mM HEPES, pH 7.4, 20 to 25% (w/v) PEG 8000) and left at 4° C. Crystals appeared after approximately six weeks. Crystals were soaked in a cryoprotectant solution containing the mother liquor, supplemented with 25% (v/v) glycerol, and flash cooled at 100 K in cold nitrogen gas stream (Oxford Cryosystem, Oxford, UK). A data set of 180 frames was collected (180° oscillation) using a CCD mounted on a rotating anode Rigaku X-ray generator. The data set was processed and scaled using Mosflm [Battye T G G, et al., *Acta Crystallogr Sect D Biol Crystallogr* 67: 271-81 (2011)] and AIMLESS [Evans P R, and Murshudov G N. *Acta Crystallogr Sect D Biol Crystallogr* 69: 1204-14 (2013)] respectively [Leslie A G W, and Powell H R. *Evolving methods for macromolecular Crystallography*. 2007]. The structure of the complex was determined by molecular replacement, using the Phaser program and the thrombin-variegin crystal structure (PDB:3B23) as the template [McCoy A J. *Acta Crystallogr Sect D Biol Crystallogr* International Union of Crystallography 63: 32-41 (2006)]. Model building and refinement was performed using COOT [Emsley P, and Cowtan K. *Acta Crystallogr Sect D Biol Crystallogr* International Union of Crystallography 60: 2126-32 (2004)].

Clot-Bound Thrombin Inhibition

Clot-bound thrombin activity was tested using S2238. Briefly, fibrin clots were prepared by incubating 100 μL of 2 mg/mL fibrinogen (in 50 mM HEPES buffer, pH 7.5, 150 mM NaCl, 10 mg/mL CaCl2) with 100 μL 30 nM thrombin. After 2 h at 37° C., the clots were extensively washed with the same buffer. This washing was repeated after every three hours for a period of 24 hr. Different concentrations of avathrin were then added to the clots and incubated for 60 min. Chromogenic substrate, S2238 (final concentration 200 μM) was then added and the reaction mixture was incubated for 90 min at 37° C. Aliquots were taken, and substrate hydrolysis was estimated by end point reading at 405 nm, using a Tecan InfinitePro microplate reader. Experiments were performed in quadruplicate and percentage inhibition was plotted.

Ferric Chloride-Induced Carotid Artery Thrombosis Model

All animal experiments were carried out under protocol 041/12 approved by Institutional Animal Care and Use Committee, National University of Singapore. The ferric chloride induced carotid artery thrombosis model was performed as described previously [Eckly A, et al., *J Thromb Haemost* 9: 779-89 (2011)] with minor modifications. Typically, C57BL/6 male mice (9-11 weeks old, 24.5-27.5 g) were anesthetized with an intraperitoneal injection of ketamine (75 mg/kg) and medetomidine (1 mg/kg). 100 μL of different doses of avathrin were injected into the mice via tail vein. The right carotid artery was dissected using blunt dissection and a vascular injury was caused applying filter paper of 2 mm×2 mm saturated with FeCl3 on top of the carotid artery. After 3 min, the filter paper was removed and the vessel was washed with sterile normal saline. To determine the time to occlusion, a miniature Doppler flow probe (Transonic Systems Inc., Ithaca, N.Y., USA) was placed around the carotid artery and blood flow was recorded using a Transonic® flow meter from ADInstruments (Dunedin, New Zealand). The maximal time for monitoring the blood flow after injury was 30 min. Mice were euthanized by cervical dislocation immediately after the completion of the experiment and prior to recovery from anesthesia.

Collection of Blood into Blood Tubes with Peptides

Individual peptides are dissolved in phosphate buffered saline to prepare 10× peptide solutions (ie. concentrations of peptides are 10 times higher than the final concentrations at which they are to be tested). 0.3 ml of the 10× peptide solutions are placed in blood tubes without any additives. Blood was drawn from healthy volunteers using syringes and immediately transferred to a 50 ml conical centrifuge tube (Falcon tube) before pipetting 2.7 ml of the blood into blood tubes with peptide solutions. Final concentrations of peptides are as stated in Table 5 and 6.

Anti-Coagulation Effect of Peptides in Blood Tubes

Blood tubes with various peptides at different concentrations were left standing at room temperature until tested at designated times. At different time points, tubes were inverted several times and visually inspected for insoluble materials as indications of clot formation.

Preservation of Platelet Function in Blood Tubes Added with Peptides

Blood tubes with various peptides at different concentrations were left standing at room temperature until tested at designated times. At different time points, tubes were inverted several times and blood samples were taken out for platelet aggregation tests using a Multiplate® Platelet aggregometer with adenosine diphosphate (ADP) as agonist according to manufacturer's recommended protocols.

Results

Detection of Variegin-Like Transcripts in Salivary Glands of *Amblyomma variegatum*

Degenerate primers based on variegin sequence amplified a transcript (AB183707) encoding a 219-residue precursor protein (BAD29729) from the salivary gland cDNA of 9-days fed female *Amblyomma variegatum*. This precursor contains a putative secretion signal and five identical 30-residue repeats with putative cleavage sites in between, enabling post-translational cleavage of the precursor to five active peptides. Expression of this precursor protein in the salivary glands was confirmed by in situ hybridization. The probe hybridized in the cytoplasm of the large basal granular cells of type I salivary gland acini. Localization of the transcripts in salivary glands of nymphs and adult female and male ticks demonstrated differences in expression during the course of feeding as well as individual variability in onset of expression. The strongest expression was detected in 2-4 days fed nymphs, 5 days fed females and in 12 day fed males, i.e. at the time when females were engorged and started to detach (FIG. 1A-I). We considered just a small stretch of sequence within the 219 amino acid sequence is enough for activity, hence synthesized SEQ ID NO: 1 avathrin (30 amino acids). The nucleotide sequence encoding SEQ ID NO: 1 is set out in SEQ ID NO: 26.

The active peptides encoded by this transcript showed ~40% sequence identity to variegin. These peptides also showed several differences in key functional residues compared to variegin:

(i) Variegin has an acidic N-terminus which was postulated to be important for fast binding kinetics [Koh C Y, et al., *J Biol Chem* 282: 29101-13 (2007)]. In contrast, acidic residues are generally absent in these variegin-like peptides;

(ii) Variegin inhibits thrombin by disrupting the charge relay system of the active site catalytic triad by its His12 possibly hydrogen bonding with Ser195 of thrombin [Koh C Y, et al., *PLoS One* 2011; 6]. In these variegin-like peptides, this functional histidine is replaced by serine;

(iii) Thr14 in native variegin is glycosylated and it showed 14-fold higher affinity than synthetic variegin [Koh C Y, et al., *J Biol Chem* 282: 29101-13 (2007)]. In variegin-like peptides, glutamine, which cannot be glycosylated was present at this position;

(iv) Pro16 and Pro17 in variegin introduce kinks in the backbone, possibly limiting conformational flexibility in the linkage between the active site and the exosite-I binding segment [Koh C Y, et al., *PLoS One* 2011; 6]. The similar region in variegin-like peptides contains three glycines, imparting a lot more flexibility to the peptide.

All these differences provided the impetus to evaluate the structure-function relationships of these variegin-like peptides. Hence, we proceeded to synthesize the active peptide from the precursor protein (BAD29729) to further characterize its inhibitory effect on human α-thrombin.

Avathrin is a Potent and Selective Inhibitor of Thrombin

Figure 1:
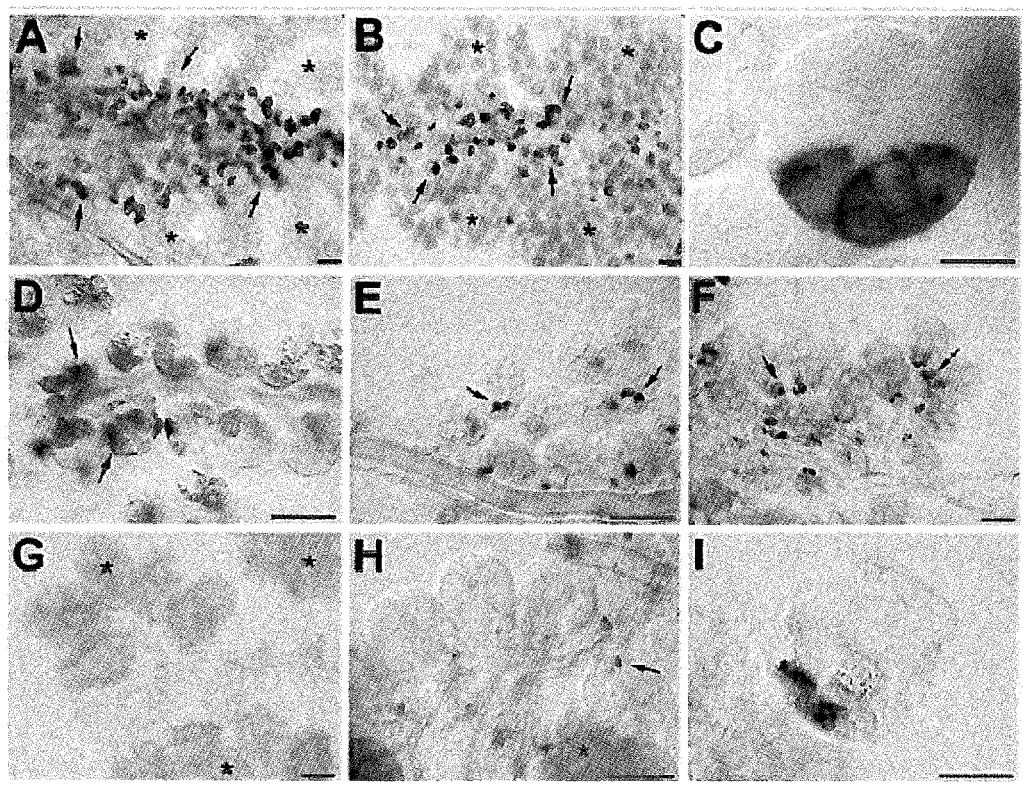
FIG. 1 shows localization of mRNA coding for variegin-like precursor protein BAD29729 in the salivary glands of *Amblyomma variegatum*. Whole mount in situ hybridization revealed expression of BAD29729 in type II acini located close to the main salivary duct, but not in the other types of acini (type III acini are indicated by asterisks). Arrows indicate the sites of expression. A-C. Salivary glands of 5 day fed female (A) and 12 day fed male (B) showing strong expression of BAD29729 in 2-4 large cells (C). D-H. Expression of BAD29729 in nymphs during the course of the blood-feeding. Unfed (D), 2-day-fed (E) and 4-day-fed (F) nymphs showing staining in the basal regions of type II acini. This staining absented in the 6-day-fed individuals (G) and was very weak in fully engorged and detached (H) nymphs. 1. Close up of type II acinus of the 2-day-fed nymph showing staining in two basal cells. Bars 100 µm (A-B), 50 µm (D-H) and 25 µm (C, I). J. Sequence alignment of variegin (SEQ ID NO: 28) and avathrin (SEQ ID NO: 1) (active thrombin inhibitory peptide from the precursor protein).
Figure 2:
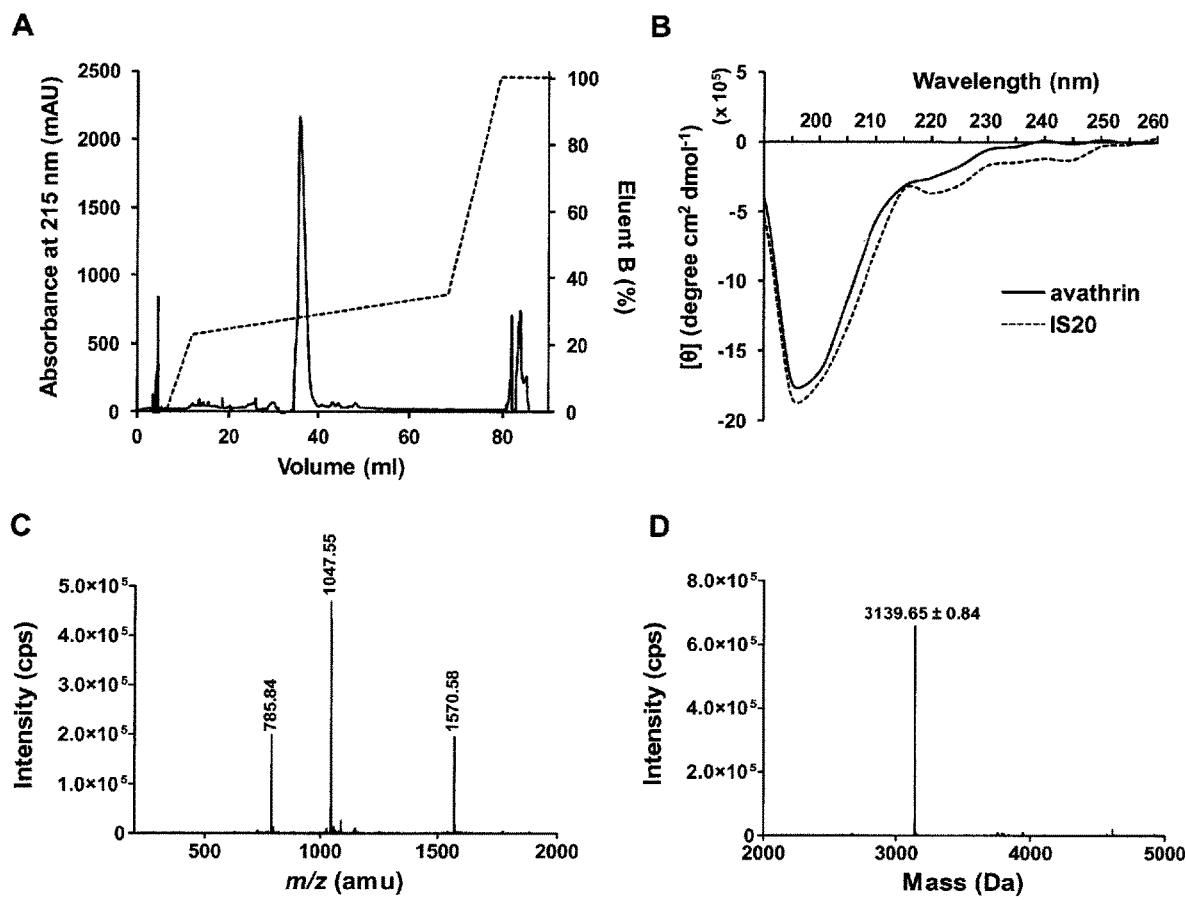
FIG. 2 shows synthesis and purification of avathrin. Avathrin was synthesized using solid phase peptide synthesis and purified using reverse phase chromatography. A. Purification of avathrin on a Jupiter Proteo (5 µm, 250 mm×10 mm, 90 Å) reversed phase column using an acetonitrile gradient from 10% eluent B to 70% eluent B (Eluent A: 0% ACN, 99.9% MilliQ water and 0.1% TFA; eluent B: 0% ACN, 99.9% MilliQ water and 0.1% TFA). B. Far-UV CD spectra (260-190 nm) of avathrin and its truncated variant—IS20, dissolved in 10 mM sodium phosphate buffer (pH 7.4). Both spectra were typical of random coil. C. Purity and mass of avathrin were determined by ESI-MS. Avathrin ionized in three different charge states and showed m/z values of 785.84 amu, 1047.55 amu and 1570.58 amu corresponding to +4, +3 and +2 charge states respectively. D. Deconvoluted mass spectrum of avathrin showed that the observed mass of avathrin corresponded to the expected mass of 3139.65±0.83 Da (Table 1).

The active peptide, named avathrin (*Amblyomma variegatum* thrombin inhibitor) was synthesized by fmoc-based solid phase peptide synthesis and purified to homogeneity (FIG. 2). Avathrin inhibited thrombin amidolytic activity on the small peptidyl chromogenic substrate S2238 in a dose-dependent manner with $IC_{50}$ and Hill slope of 6.95±0.42 nM and 0.92±0.01, respectively. Significant inhibition (14.33±1.39%) was observed for equimolar concentrations of thrombin and avathrin (0.81 nM thrombin; 1 nM avathrin) fitting the descriptions of typical tight-binding inhibitors

Figure 3:
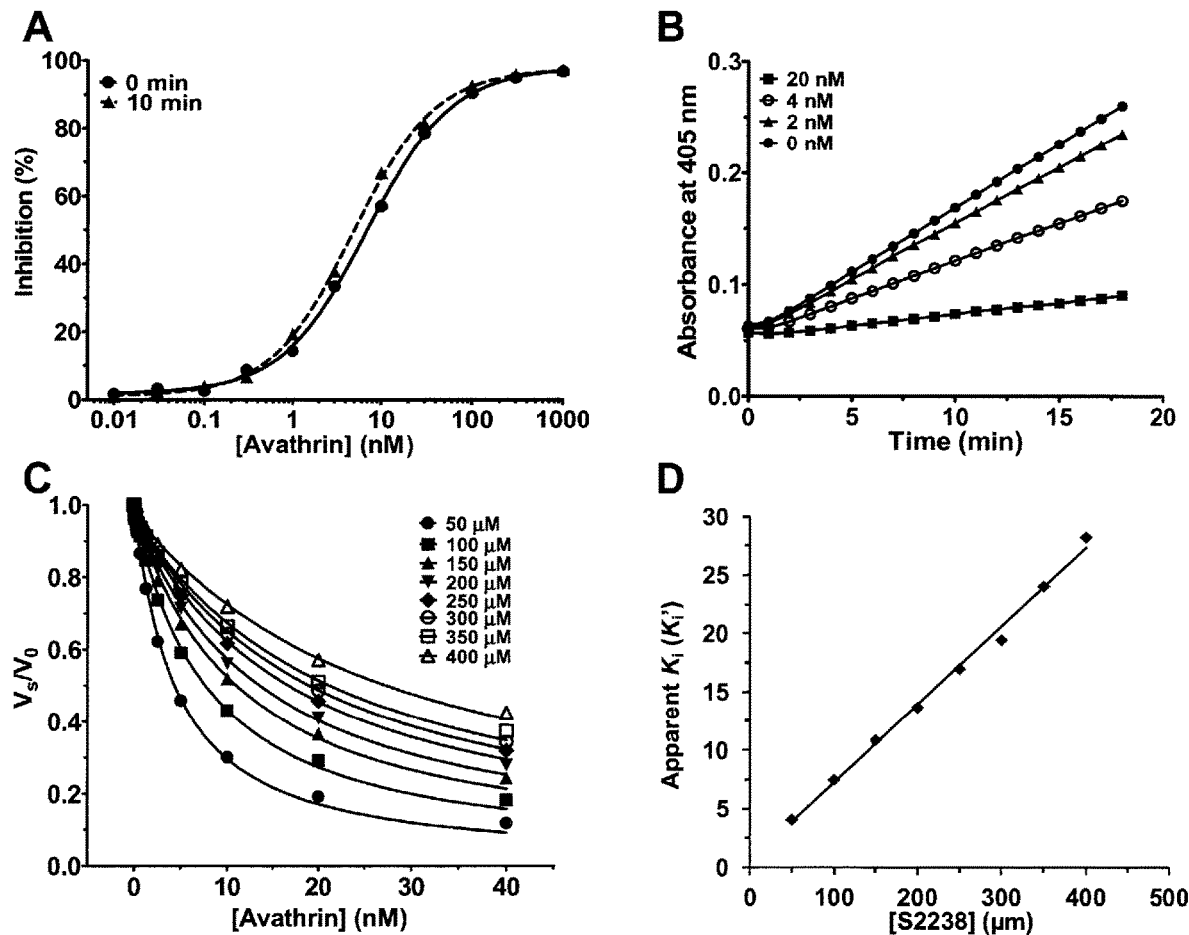
FIG. 3 Shows thrombin inhibitory activity of avathrin. A. The effect of various concentrations of avathrin on the amidolytic activity of thrombin (0.81 nM) was measured using S2238 (100 µM) with (10 min) or without pre-incubation. Avathrin showed an inhibition of the thrombin amidolytic activity in a dose dependent manner. $IC_{50}$ and Hill slope of the inhibition are 6.95±0.42 nM and 0.92±0.01 at 0 min; and 4.86±0.36 nM and 0.94±0.02 nM at 10 min, respectively. Each data point is the mean±S.D. of at least three experiments. B. Thrombin (0.81 nM) amidolytic assay using S2238 (100 µM) in presence of various concentrations of avathrin was carried out and linear progression curves of thrombin inhibition in presence avathrin were achieved—a characteristic of fast binding inhibitor. C. The residual thrombin amidolytic activity in presence of various concentrations of avathrin was measured at different concentrations of S2238 and the $K_i'$ (apparent K) was determined. Reactions were started with the addition of thrombin (0.81 nM). Data were fitted to the Morrison tight binding equation using GraphPad Prizm software. Each data point is the mean±S.D. of at least three experiments. D. Plot of $K_i'$ versus S2238 concentration increased linearly, indicating avathrin is a competitive inhibitor. The inhibitory constant $K_i$ was determined to be 545.3±3.1 pM.
Figure 4:
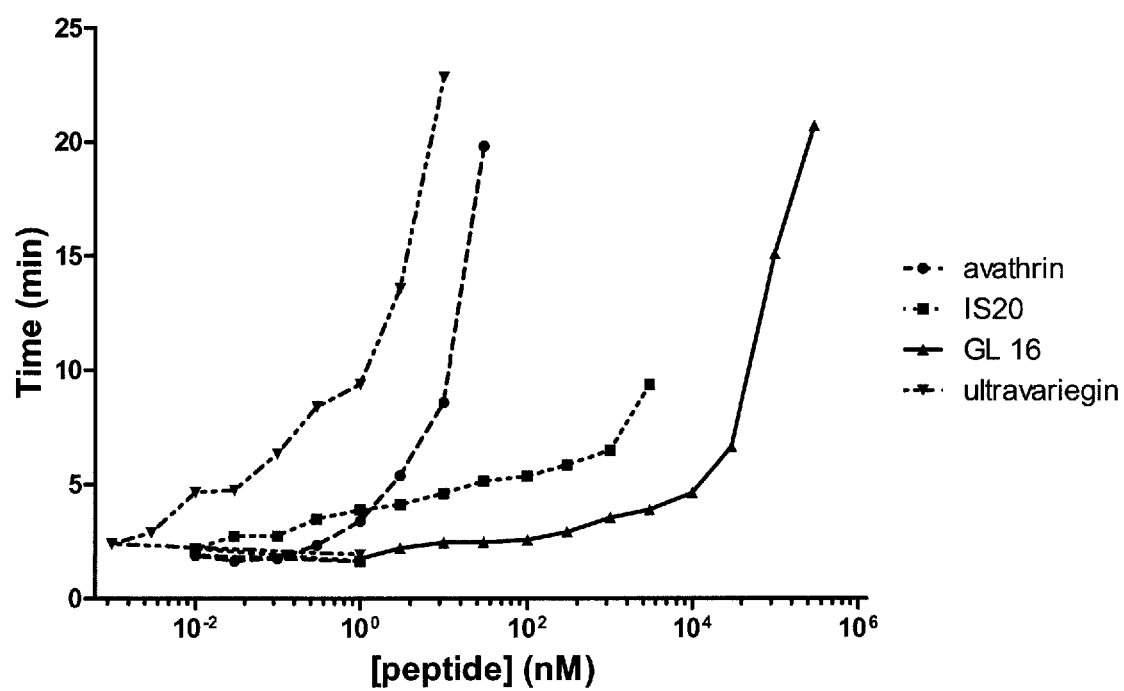
FIG. 4 shows inhibition of thrombin fibrinogenolytic activity, whereby avathrin, IS20, GL16 and ultravariegin prolonged fibrinogen clotting times in a dose dependent manner.

[Copeland R a. *Enzymes: A practical Introduction to Structure, mechanism, and data analysis.* 2000] (FIG. 3A). Reaction progress curves showed that a steady-state equilibrium was achieved upon mixing, indicating a fast binding mode (FIG. 3B). Reaction velocities of thrombin were determined in the presence of different concentrations of avathrin to obtain the apparent inhibitory constant, $K_i'$. A plot of $K_i'$ increased linearly with increasing concentrations of S2238, indicating that avathrin is a competitive inhibitor of thrombin with respect to S2238 (K of 545.3±3.1 pM) (FIG. 3C, 3D). Thus, avathrin is a fast, tight binding, competitive inhibitor of thrombin. Avathrin also prolonged fibrinogen clotting time in a dose-dependent manner indicating that it also inhibits the fibrinogenolytic activity of thrombin (FIG. 4).

The selectivity of avathrin was examined by screening it against 13 serine proteases. At 10 nM, avathrin inhibited 65% of thrombin activity. However, even at 100 μM, inhibition of other proteases was <30% (FIG. 5), indicating that avathrin is a highly selective inhibitor with at least four orders of magnitude of selectivity preference for thrombin.

Avathrin Exhibits Prolonged Thrombin Inhibition

Figure 6:
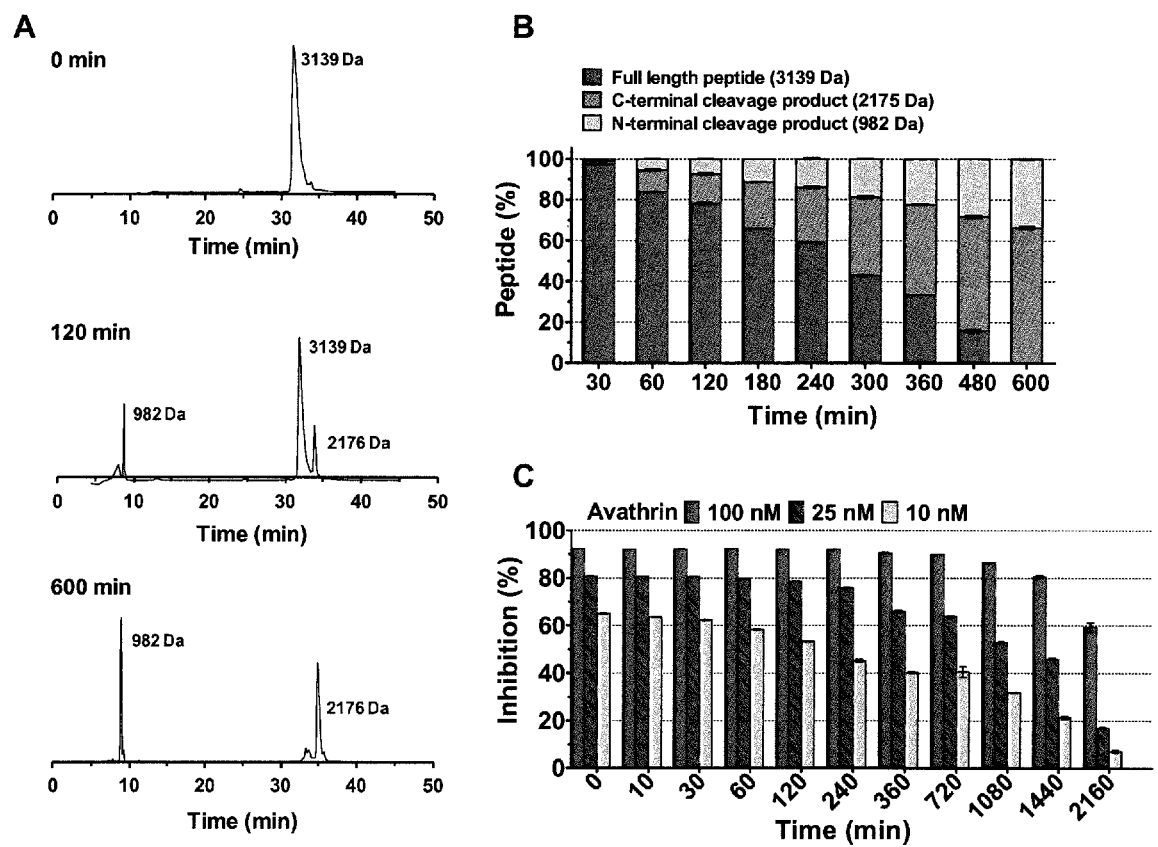
FIG. 6 shows cleavage of avathrin by thrombin. A. Evaluation of avathrin cleavage by thrombin by HPLC chromatograms. Avathrin (150 µM) was incubated with thrombin (5 µM) for various times and the reaction mixtures were separated using RP-HPLC; the masses of the cleavage products were analyzed with ESI-MS. At 0 min (upper panel), a single peak corresponding to full length avathrin (mass 3139 Da) was identified. At 120 min (middle panel), two new peaks corresponding to N-terminal cleavage product ($^1$SGGHQTAVPK$^{10}$ of SEQ ID NO: 1; mass 982 Da) and C-terminal cleavage product (ISKQGLGGDFEEIPSDEIIE (SEQ ID NO: 4); mass 2176 Da) were identified in addition to avathrin peak. At 600 min (lower panel), two peaks corresponding to the N- and C-terminal cleaved products were observed while avathrin peak was not observed, indicating complete cleavage. B. Time-dependent cleavage of avathrin by thrombin. Relative percentages of avathrin, its N- and C-terminal cleavage products were quantified by calculating areas under the curve. Each data point is the mean±S.D. of at least three independent experiments. C. Effect of thrombin cleavage on inhibitory properties of avathrin. Avathrin was incubated with thrombin (0.81 nM) for up to 36 h, and assayed at different time points for its ability to inhibit thrombin amidolytic activity on the chromogenic substrate S2238. At 25 nM of avathrin, the inhibitor was present in ~30-fold excess of thrombin (0.81 nm), and these ratios are similar to that used in HPLC analysis of cleavage products. After 24 h, cleavage products retained >50% of the original inhibitory activity, although full length avathrin was completely cleaved around 10 h. Thus, cleavage products, particularly the C-terminal cleavage product of avathrin appears to remain bound to thrombin and continues to inhibit thrombin. Each data point is the mean±S.D. of at least three independent experiments.
Figure 7:
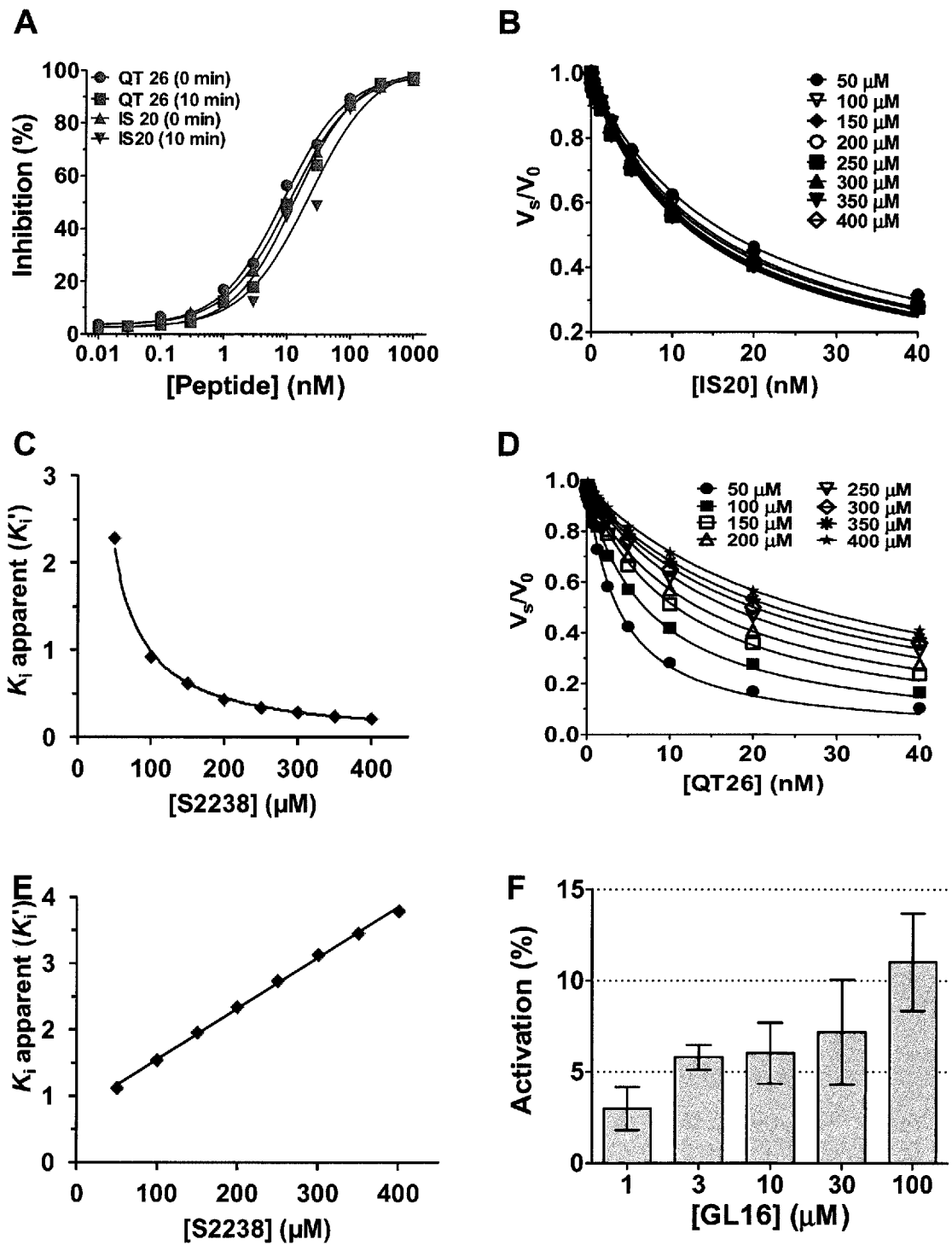
FIG. 7 shows the effects of truncated avathrin mutants on thrombin amidolytic activity. A. The effect of QT26 and IS20 on the amidolytic activity of thrombin (0.81 nM) was measured. Both peptides inhibit thrombin in a dose-dependent manner. QT26 had $IC_{50}$ and Hill slope of 8.94±0.64 nM and 0.88±0.03 at 0 min; and 13.54±0.81 and 0.92±0.03 at 10 min respectively. IS20 had $IC_{50}$ and Hill slope of 12.38±0.32 nM and 0.86±0.02 at 0 min; and 22.70±0.94 nM and 0.87±0.01 at 10 min respectively. Each data point is the mean±S.D. of at least three independent experiments. B. GL16 (3, 10, 30, 100, and 300 µM) was unable to inhibit thrombin amidolytic activity; instead at high concentrations, it slightly enhanced the hydrolysis of S2238 by thrombin. Each data point is the mean±S.D. of at least three independent experiments. C and D. The residual thrombin amidolytic activity in presence of QT26 and IS20 was measured and the $K_i'$ (apparent $K_i$) was determined. Both QT26 and IS20 were tight binding inhibitors. Each data point is the mean±S.D. of at least three experiments. E. Plot of $K_i'$ against S2238 concentration increased linearly, indicating QT26 is a competitive inhibitor. The inhibitory constant $K_i$ was determined to be 760.32±0.91 pM. F. Plot of $K_i'$ against S2238 concentration decreased curvilinearly, indicating IS20 is a non-competitive inhibitor (with $\alpha<1$). The inhibitory constant $K_i$ was determined to be 5760±230 pM.

Competitive inhibition of thrombin peptidyl substrate S2238 indicates that avathrin binds to the active site, and hence it may be susceptible to proteolytic cleavage by thrombin, similar to all other macromolecular substrates or inhibitors such as variegin and bivalirudin. We investigated the cleavage of avathrin by thrombin by incubating it with the enzyme (30:1 ratio) for increasing amounts of time and analysed the reaction by reverse-phase chromatography (RP-HPLC) and electrospray ionization mass spectrometry (ESI-MS). With incubations, two new peaks corresponding to $^1$SGGHQTAVPK$^{10}$ (981.3 Da) of SEQ ID NO: 1 and $^{11}$ISKQGLGGDFEEIPSDEIIE$^{30}$ (2176.3 Da) of SEQ ID NO: 1 were identified, indicating cleavage at Lys10-Ile11 scissile bond (FIG. 6A). The cleavage was quantified by calculating the areas under peaks in the chromatograms (FIG. 6B). With increasing lengths of time, the amounts of the cleaved products increased, while that of the full length peptide decreased and avathrin was completely cleaved at ~10 h. The effect of cleavage on the inhibitory activity was evaluated (FIG. 6C). At the same avathrin: thrombin ratio (1:30) used for cleavage experiments, >45% of thrombin amidolytic activity was inhibited at 24 h, indicating prolonged inhibition of thrombin even after avathrin was completely cleaved. Variegin displayed similar behaviour as its cleaved peptide C-terminal to the scissile bond continues to inhibit thrombin after cleavage. To test if the cleavage product of avathrin similarly inhibits thrombin, the corresponding peptide (IS20), was purified and tested for inhibition. IS20 inhibited thrombin amidolytic activity with $IC_{50}$ of 12.38±0.32 nM (FIG. 7A). The $K_i'$ decreases curvilinearly with increasing S2238 concentrations, indicating that IS20 is a non-competitive inhibitor with respect to the small peptidyl substrate, with an overall $K_i$ of 5.76±0.23 nM (FIGS. 7B and 7C). IS20 also inhibited the fibrinogenolytic activity of thrombin in a dose-dependent manner (FIG. 4). Thus, avathrin exhibited prolonged inhibition through its C-terminal peptide, which retained a strong binding affinity for thrombin.

Thrombin Binding Segments on Avathrin

We synthesized two additional truncated variants of avathrin, namely QT26 and GL16, to localize thrombin binding segments on avathrin. Four and 15 N-terminal residues of avathrin were deleted in QT26 and GL16, respectively. Both peptides were tested for their ability to inhibit thrombin amidolytic and fibrinogenolytic activity. QT26 inhibited thrombin amidolytic activity ($IC_{50}$=8.94±0.64 nM and $K_i$=760.32±0.91 pM) (FIGS. 7A, 7D and 7E) and fibrinogenolytic activity (FIG. 4). Compared to full-length avathrin, the loss of activity due to deletion of 4 N-terminal residues in QT26 is minimum. GL16, in contrast, did not inhibit amidolytic activity even at 300 μM, and instead showed a slight activation (5-10%) (FIG. 7F). However, it inhibited the fibrinogenolytic activity (FIG. 4). Taken together, this indicates that QT26 contains both active site and exosite-I binding sequences but GL16 contains only exosite-I binding sequences. Since the scissile bond is between Lys10-Ile11, the active site binding segment of avathrin is located within the sequence $^5$QTAVPKISKQ$^{14}$ of SEQ ID NO: 1.

Structure-Function Relationships of Thrombin-Avathrin Interactions

Despite low overall sequence identity between variegin and avathrin, and the changes in several key functional residues as outlined above, functionally avathrin showed a high degree of similarity to variegin in its thrombin inhibitory activity. To further investigate the significance of differences in the two sequences, we evaluated a series of avathrin substitution mutants informed by previous structure-function studies with variegin [Koh C Y, et al., *PLoS One* 2011; 6]:

(i) The key functional residue—VHis12 of variegin that most likely disrupts the catalytic triad of thrombin is replaced with ASer12 in avathrin. We synthesized two mutants replacing ASer12 with Ala (S12A) or His (S12H). S12A showed a similar drop in potency (>10-fold) to that observed in the analogous variegin mutant (FIG. 8A), suggesting the importance of ASer12 for the inhibitory effect of avathrin. S12H inhibited thrombin with an $IC_{50}$ of 18.51±0.32 nM (FIG. 8A), which was 2-fold less potent than avathrin, suggesting that serine makes avathrin a stronger thrombin inhibitor than if it were to have a histidine at this position.

Figure 8:
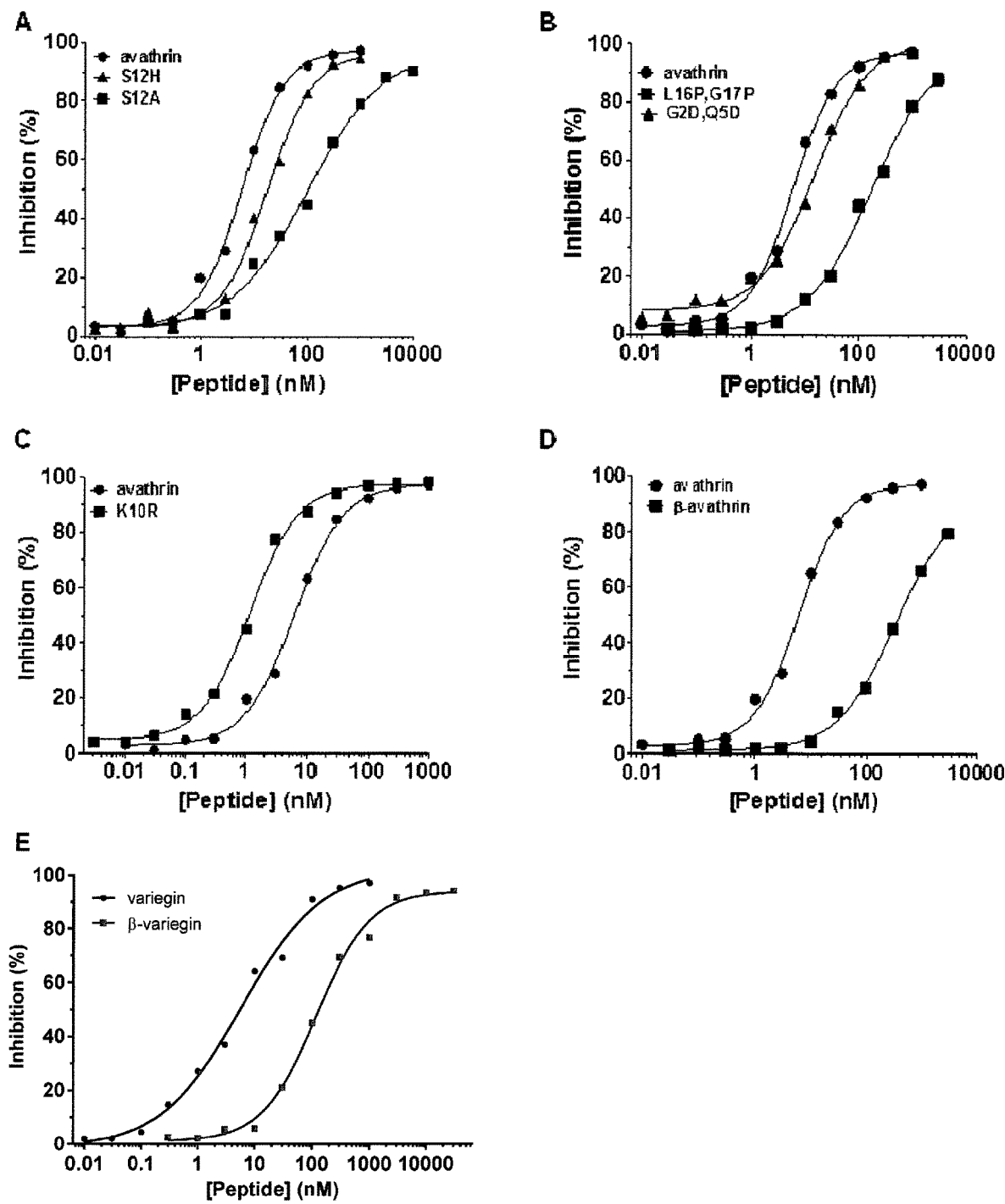
FIG. 8 shows the effect of avathrin variants on thrombin amidolytic activity compared with that of avathrin. All variants inhibited thrombin activity in a dose-dependent manner. A. S12A had an $IC_{50}$ and Hill slope of 101.20±1.32 nM and 0.62±0.01 respectively. The $IC_{50}$ of S12A was 20-fold lower than avathrin, confirming the importance of Ser12 in avathrin for thrombin inhibition. S12H had an $IC_{50}$ and Hill slope of 18.51±0.32 nM and 0.88±0.02 respectively. Each data point is the mean±S.D. of at least three experiments. B. L16P, G17P had an $IC_{50}$ and Hill slope of 181.32±3.76 nM and 0.54±0.02 respectively. G2D, Q5D had an $IC_{50}$ and Hill slope of 12.98±1.23 nM and 0.71±0.03 respectively. Each data point is the mean±S.D. of at least three independent experiments. C. K10R had an $IC_{50}$ and Hill slope of 1.15±0.45 nM and 1.10±0.01 respectively. K10R had a 5-fold gain in activity but was cleaved at a rate much faster than avathrin (3 h). Each data point is the mean±S.D. of at least three independent experiments. D. β-avathrin had an $IC_{50}$ and Hill slope of 332.16±1.32 nM and 0.62±0.01 respectively. Although β-avathrin was not cleaved for up to 72 h, it had a severe drop in its potency. Each data point is the mean±S.D. of at least three independent experiments. E. β-variegin had an $IC_{50}$ and Hill slope of 117.90±1.16 nM and 0.93±0.05 respectively. Each data point is the mean±S.D. of at least three independent experiments.

(ii) Variegin contains two Glu residues in its N-terminus and these two acidic residues were suspected to steer variegin towards the thrombin exosite-II and confer a fast binding inhibitory mode [Koh C Y, et al., *J Biol Chem* 282: 29101-13 (2007)]. Although avathrin exhibited fast binding kinetics without an acidic N-terminus, we were interested in investigating the role on an acidic N-terminus on the thrombin inhibitory activity of avathrin. In one double mutant peptide G2D, Q5D, acidic residues were introduced into avathrin N-terminus to emulate the possible role of electrostatic steering in conferring fast binding kinetics to variegin [Koh C Y, et al., *J Biol Chem* 282: 29101-13 (2007)]. This mutant showed slightly weaker inhibition (<2-folds) than avathrin and QT26 (FIG. 8B). Therefore, the presence of an acidic N-terminus is unlikely to be important for fast binding kinetics as previously hypothesized [Koh C Y, et al., *J Biol Chem* 282: 29101-13 (2007)].

(iii) To test the hypothesis that a more rigid, proline-rich linker between the active site and exosite-I binding segments in variegin ($^{15}$APPF$^{18}$ of SEQ ID NO: 28) is beneficial compared to the flexible glycine-rich linker in avathrin ($^{15}$GLGG$^{18}$ of SEQ ID NO: 1), the double mutant peptide L16P, G17P was synthesized and tested. This peptide registered a drop of >25-fold in activity ($IC_{50}$, 181.32±3.76 nM) compared with avathrin (FIG. 8B), indicating flexibility in the linker is needed for avathrin.

Figure 9:
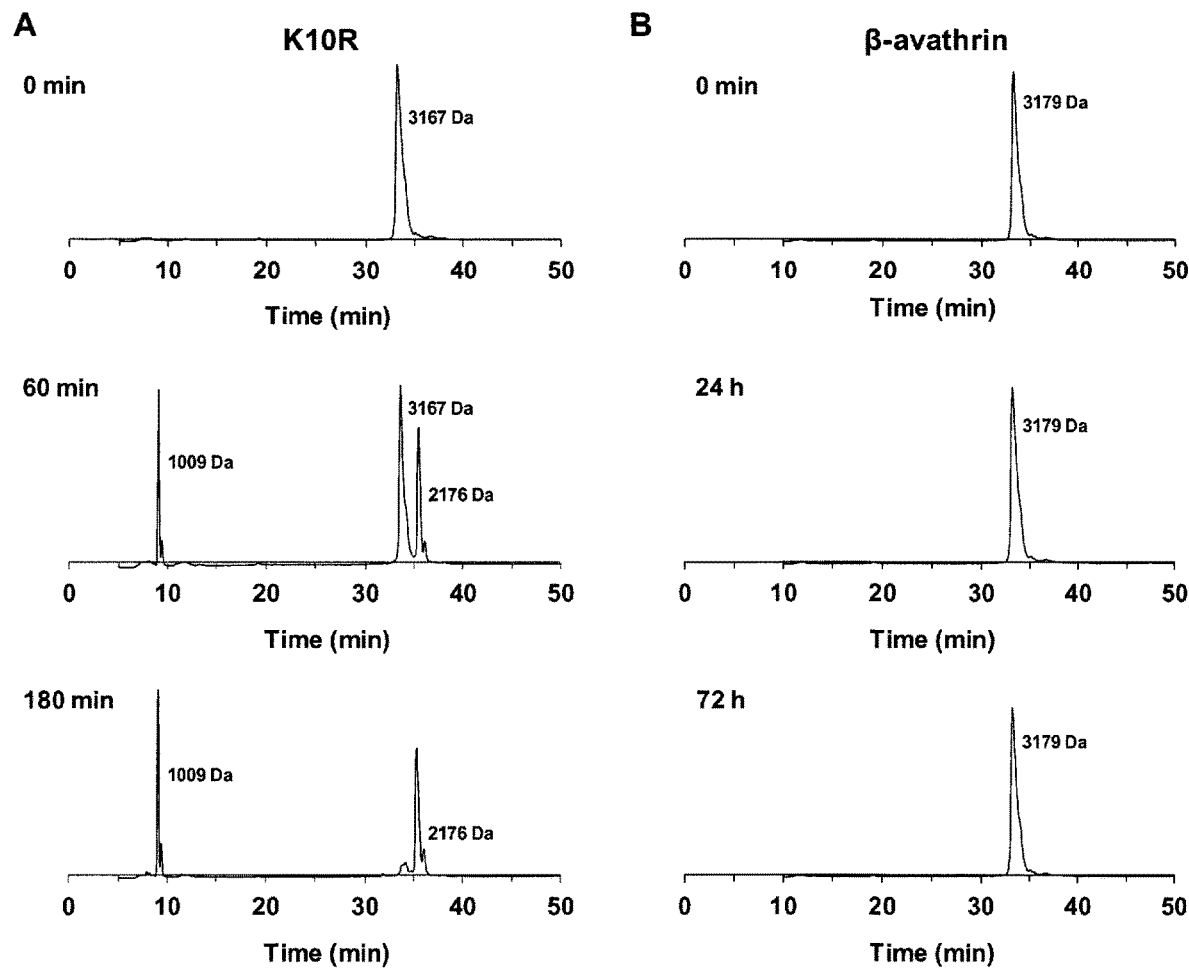
FIG. 9 shows HPLC chromatograms of cleavage of avathrin variants K10R (A) and β-avathrin (B) by thrombin. The peptides were incubated with thrombin for various times and the reaction mixtures were separated using RP-HPLC and the masses of cleavage products were analyzed using ESI-MS. While K10β-avathrin was cleaved completely after 3 h (at a rate much faster than avathrin), β-avathrin was uncleaved even after 72 h.

(iv) Thrombin is known to prefer an arginine residue at P1 [Berliner L J. *Journal of Chemical Information and Modeling.* (1992)] and the substitution of P1 Arg by Lys causes a drop of 10-fold in activity [Gallwitz M, et al., *PLoS One* 2012; 7]. Both variegin and avathrin possess a lysine at P1 and the mutation of the P1 Lys to Arg in variegin resulted in a small gain in activity (<3-fold) [Koh C Y, et al., *PLoS One* 2011; 6]. Therefore, we substituted the P1 Lys in avathrin by Arg (K10R), and observed a similar 3- to 4-fold gain in activity (IC$_{50}$, 1.15±0.45 nM) (FIG. 8C). However, cleavage of this peptide by thrombin also proceeds faster, resulting in complete cleavage within 3 h (FIG. 9A).

Figure 10:
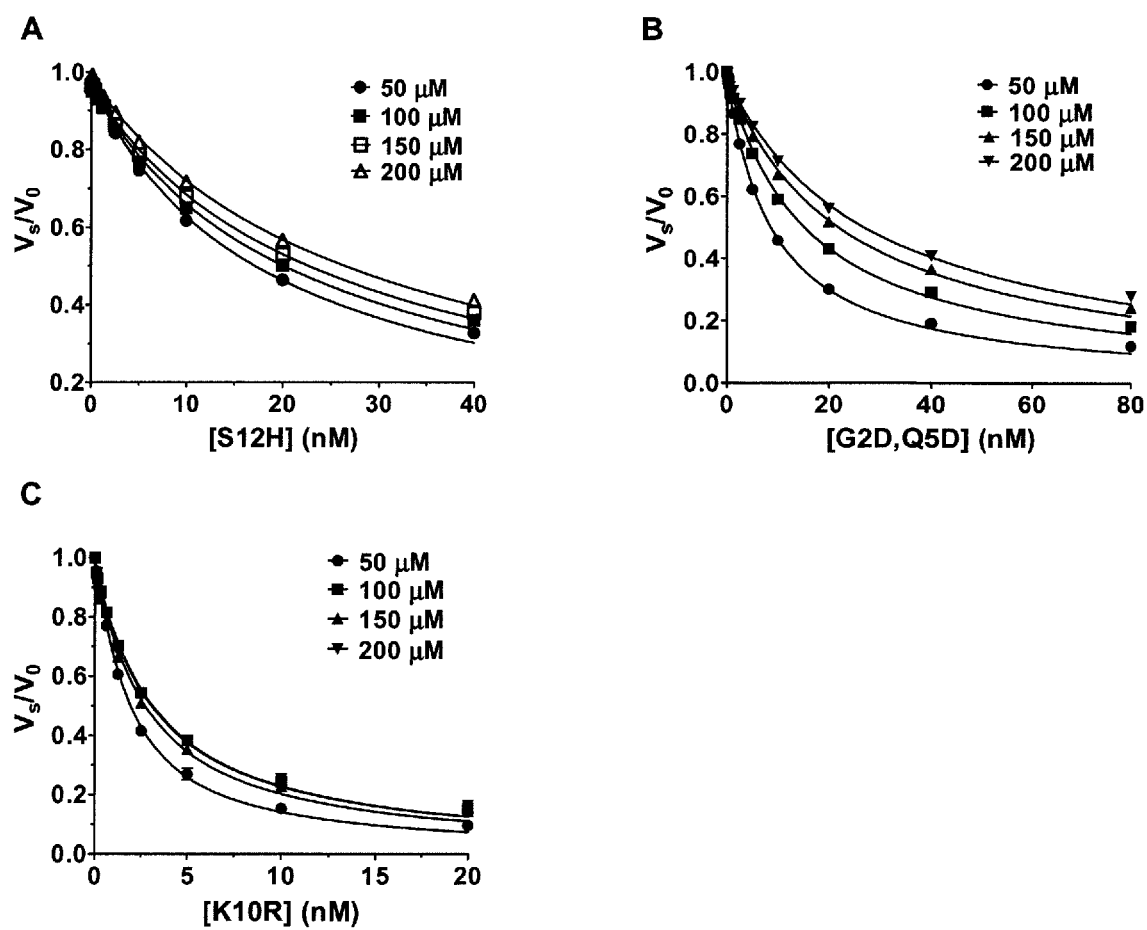
Figure 11:
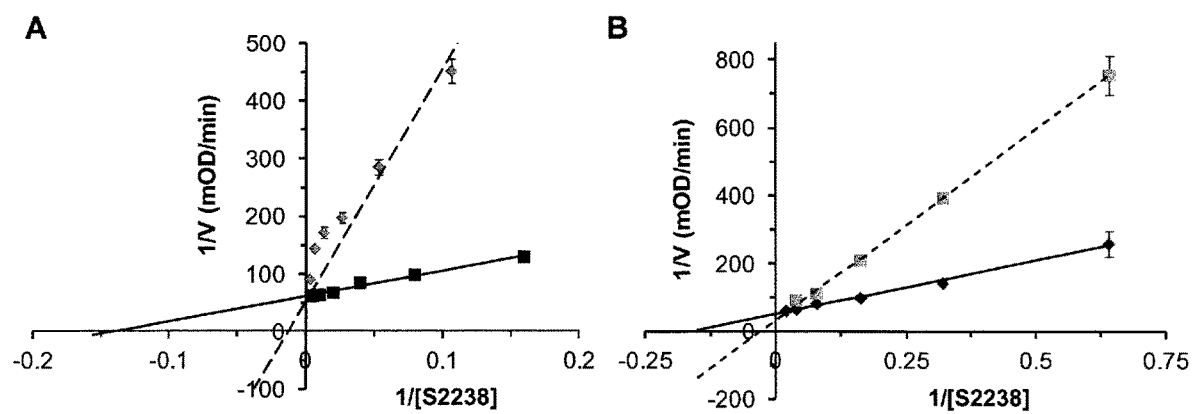

(v) Next, we synthesized a variant named β-avathrin in which the scissile peptide bond ($^V$Lys10-$^V$Ile11) was substituted by a proteolytically stable bond (β-homoArg10-Ile11). β-avathrin was >100-fold less potent than avathrin and inhibited thrombin with an IC$_{50}$ of 332±1.32 nM (FIG. 8D). Although it was not cleaved by thrombin for up to 72 h (FIG. 9B), the shift resulting from an additional carbon atom along the peptide backbone appears to be extremely detrimental to the activity. Similar drops in activity were also observed with hirulog variants in which scissile bond replacements were made to make the peptides cleavage resistant [Bourdon P. *Biochem Biophys Res Commun* 177: 1049-55 (1991)]. The K$_i$ values of these peptides are shown in FIGS. 10 and 11. The results of avathrin and avathrin variant peptides are summarized in Tables 1 and 2.

In Table 2, β is β-homoarginine.

Crystal Structure of Thrombin-Avathrin Complex

Figure 12:
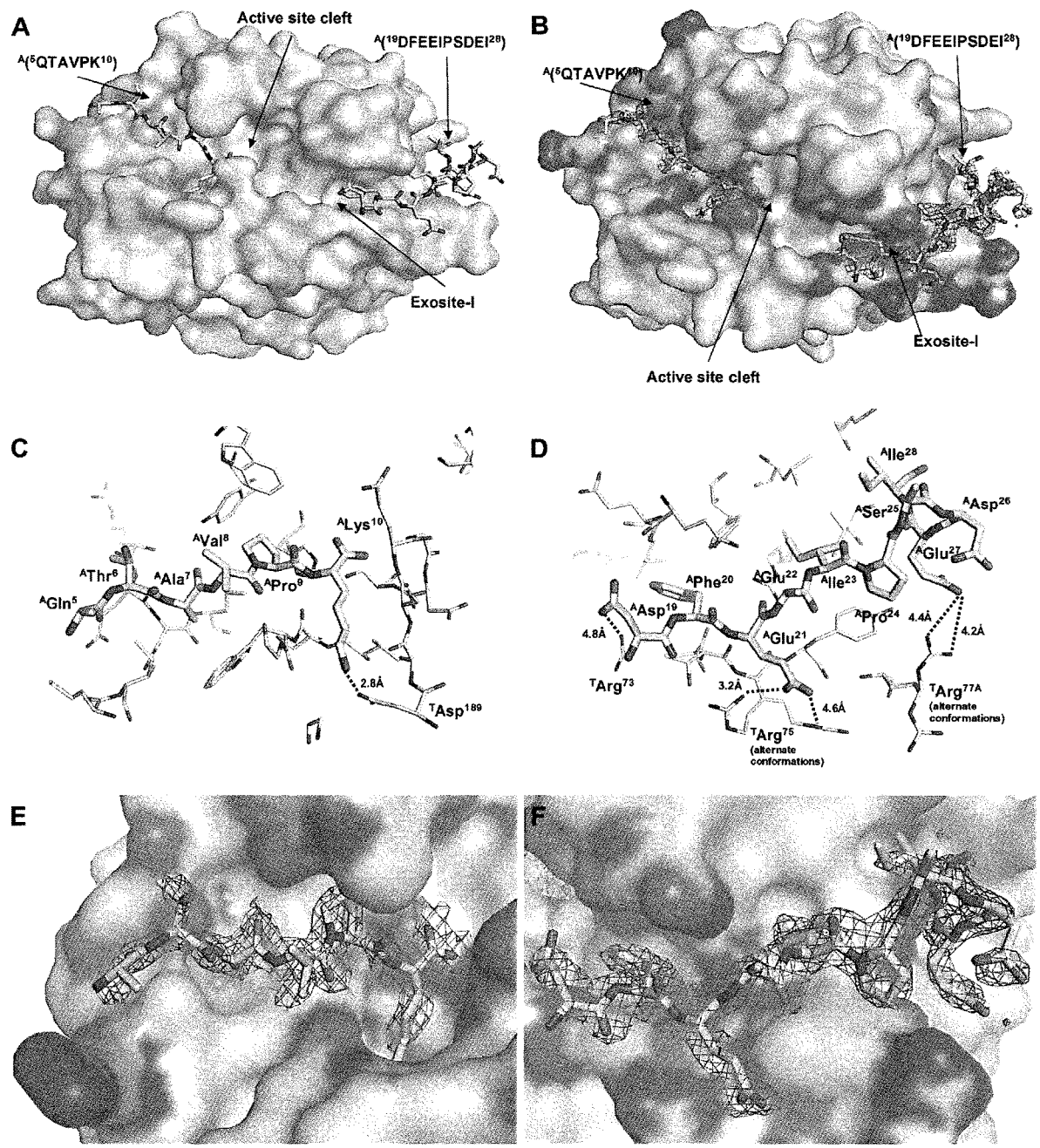

Thrombin-avathrin complex was crystallized in C2 space group and refined to a resolution of 2.09 Å (Table 3). The electron density for most thrombin residues is well-defined except for residues in the termini of the light chain; and in the autolysis loop and C-terminus of the heavy chain. Unfortunately, not all residues in the bound avathrin have density clear enough for unambiguous building of the model. No density for the first four ($^1$SGGH$^4$; SEQ ID NO: 38) and last two residues ($^{29}$IE$^{30}$) are observed. Electron density for avathrin is also discontinuous C-terminal to the scissile bond between $^A$Ile11 and $^A$Gly18. Thus, we built two segments of peptide, representing the active site binding segment N-terminus to the scissile bond ($^5$QTAVPK$^{10}$; SEQ ID NO: 39) and exosite-I binding segment ($^{19}$DFEEIPSDEI$^{28}$; SEQ ID NO: 40) (FIGS. 12A and B). We hypothesize that cleavage of avathrin has occurred during crystallization. After cleavage, residues between $^A$Ile11 and $^A$Gly18 did not have an ordered bound structure in complex with thrombin. Due to poor density, side chains of $^A$Gln5, $^A$Glu22 and $^A$Ser25 also could not be built.

TABLE 1

Expected and observed masses of avathrin and its variants

| Peptide | Expected mass (Da) | Observed mass (Da) | SEQ IQ NO: |
|---|---|---|---|
| Avathrin | 3139.42 | 3139.65 ± 0.83 | 1 |
| QT26 | 2801.10 | 2801.21 ± 0.37 | 3 |
| IS20 | 2176.36 | 2176.32 ± 0.12 | 4 |
| GL16 | 1719.82 | 1719.79 ± 0.34 | 34 |
| S12A | 3123.42 | 3123.63 ± 0.75 | 5 |
| S12H | 3189.49 | 3189.77 ± 0.28 | 6 |
| L16P, G17P | 3163.44 | 3163.48 ± 0.41 | 35 |
| G2D, Q5D | 3184.42 | 3184.40 ± 0.53 | 36 |
| K10R | 3167.44 | 3167.70 ± 0.42 | 7 |
| β-avathrin | 3179.44 | 3179.51 ± 0.78 | 8 |

TABLE 3

Crystallographic data collection and refinement statistics

| Data collection & processing | |
|---|---|
| Wavelength (Å) | 1.54 |
| Space group | C2 |
| Unit cell parameters [a, b, c (Å); β (°)] | 69.5, 71.6, 71.7; 99.9 |
| Resolution (Å) | 33.1-2.09 |
| Unique reflections | 19156 (1390) |
| Completeness (%) | 92.7 (82.9) |
| R$_{merge}$ | 0.052 (0.137) |
| R$_{pim}$ | 0.031 (0.083) |
| CC$_{1/2}$ | 1.00 (0.97) |
| Mean I/σ(I) | 16.5 (7.7) |
| Multiplicity | 3.8 (3.6) |
| Refinement | |
| Resolution (Å) | 33.1-2.09 |
| R$_{work}$ | 0.179 |
| R$_{free}$ | 0.216 |

TABLE 2

Kinetic parameters of inhibition of thrombin by avathrin and its variants

| Peptide | Sequence | IC$_{50}$ (nM) | Hill Slope | K$_i$ (nM) | SEQ ID |
|---|---|---|---|---|---|
| Avathrin | SGGHQTAVPKISKQGLGGDFEEIPSDEIIE | 6.95 ± 0.42 | 0.92 ± 0.02 | 0.545 ± 0.003 | 1 |
| QT26 | QTAVPKISKQGLGGDFEEIPSDEIIE | 8.94 ± 0.64 | 0.88 ± 0.03 | 0.760 ± 0.009 | 3 |
| IS20 | ISKQGLGGDFEEIPSDEIIE | 12.17 ± 0.32 | 0.86 ± 0.02 | 5.760 ± 0.230 | 4 |
| GL16 | GLGGDFEEIPSDEIIE | N. I.* | N. I. | N. I. | 34 |
| S12A | SGGHQTAVPKIAKQGLGGDFEEIPSDEIIE | 101.20 ± 1.32 | 0.62 ± 0.01 | 6.075 ± 0.180 | 5 |
| S12H | SGGHQTAVPKIHKQGLGGDFEEIPSDEIIE | 18.51 ± 0.32 | 0.88 ± 0.02 | 1.230 ± 0.046 | 6 |
| L16P, G17P | SGGHQTAVPKISKQGPPGDFEEIPSDEIIE | 181.32 ± 3.76 | 0.54 ± 0.02 | N. D.** | 35 |
| G2D, Q5D | SDGHDTAVPKISKQGLGGDFEEIPSDEIIE | 12.98 ± 1.23 | 0.71 ± 0.03 | 0.932 ± 0.015 | 36 |
| K10R | SGGHQTAVPRISKQGLGGDFEEIPSDEIIE | 1.15 ± 0.45 | 1.10 ± 0.01 | 0.172 ± 0.002 | 7 |
| β-avathrin | SGGHQTAVPpISKQGLGGDFEEIPSDEIIE | 332.16 ± 1.32 | 0.62 ± 0.01 | 32.04 ± 0.36 | 8 |

*N. I., No inhibition;
**N. D., Not determined

TABLE 3-continued

Crystallographic data collection and refinement statistics

| | |
|---|---|
| RMSD bonds (Å) | 0.008 |
| RMSD angles (°) | 1.32 |
| No. atoms (thrombin/avathrin/water) | 2322/119/185 |
| Residues in favoured regions (%)[#] | 97.6 |
| Residues in allowed regions (%) | 2.4 |
| Residues in disallowed regions (%) | 0 |
| Average B factors for atoms (thrombin/avathrin/water) (Å²) | 24.2/46.2/26.2 |

*Values in parenthesis are for the highest resolution shell
[#]Ramachandran Plot statistics are as reported by the Molprobity server Thrombin inhibition by avathrin appears to be through blocking of the active site as expected from amidolytic assays showing competitive inhibition with small peptidyl substrates. The model displayed the state of the active site after cleavage, in which thrombin charge relay system appears to be in place. Oγ of $^T$Ser195 is 2.7 Å away from Nε of $^T$His57, and the Nδ of $^T$His57 is in turn 2.7 Å away from Oδ of $^T$Asp102. The Cα of $^A$Lys10 (P1) appears to shift further away from the nucleophile (Oγ of $^T$Ser195) at 3.2 Å since the cleavage has occurred. The $^A$Lys10 carbonyl oxygen is still stabilized in the oxyanion hole, positioned at a distance of 3.1 Å from the backbone nitrogen of $^T$Gly193. P1 $^A$Lys10 binds in the S1 subsite as expected, with its side chain amine forming a hydrogen bond with $^T$Asp189 at the bottom of the specificity pocket. P2 $^A$Pro9 pyrrolidine ring appears to interact with aromatic side chains of $^T$His57 and $^T$Tyr60A perpendicularly, resembling typical edge-to-face pi interactions. P3 $^A$Val8 side chain is solvent exposed and without specific interactions. The methyl group of P4 $^A$Ala7 side chain in contrast is completely buried in a hydrophobic pocket formed by $^T$Asn98, $^T$Leu99, $^T$Ile174 and $^T$Trp216. P5 $^A$Thr6 and P6 $^A$Gln5 are both solvent exposed as the peptide approaches exosite-II but there is lack of electron density for avathrin beyond this point such that it is not possible to determine if the peptide extends towards exosite-II (FIG. 12C).

Residues located immediately C-terminal to the scissile bond did not show good electron density until around exosite-I. Overall, this part of avathrin binds in the exosite-I groove like hirugen, hirulog-1 and variegin [Koh C Y, et al., PLoS One 2011; 6; Skrzypczak-Jankun E, et al., J Mol Biol 221: 1379-93 (1991); Qiu X, et al., Biochemistry 31: 11689-97 (1992)]. Both electrostatic and hydrophobic interactions appear to be important for this binding. Three electrostatic interactions ($^A$Asp19-$^T$Arg73, $^A$Glu21-$^T$Arg75 and $^A$Glu27-$^T$Arg77A) between the avathrin C-terminus and exosite-I are observed (FIG. 12D). Three hydrophobic side chains ($^A$Phe20 $^A$Ile23 and $^A$Ile28) are buried in the avathrin-thrombin interface. $^A$Ile23 and $^A$Ile28 are buried inside a large hydrophobic pocket that is formed by the side chains of $^T$Phe34, $^T$Leu65, $^T$Arg67, $^T$Tyr76 and $^T$Ile82. Additionally, the partially exposed $^A$Pro24 appears to have some favourable contacts with the phenol ring of $^T$Tyr76. Residues $^A$Glu22 and $^A$Ser25 are solvent exposed and lack side chain density hence their interactions with thrombin are not interpretable. Also, there is very poor electron density observed after $^A$Ile28 which does not allow the placement of $^A$Ile29 and $^A$Glu30.

Clot-Bound Thrombin Inhibition

Figure 13:
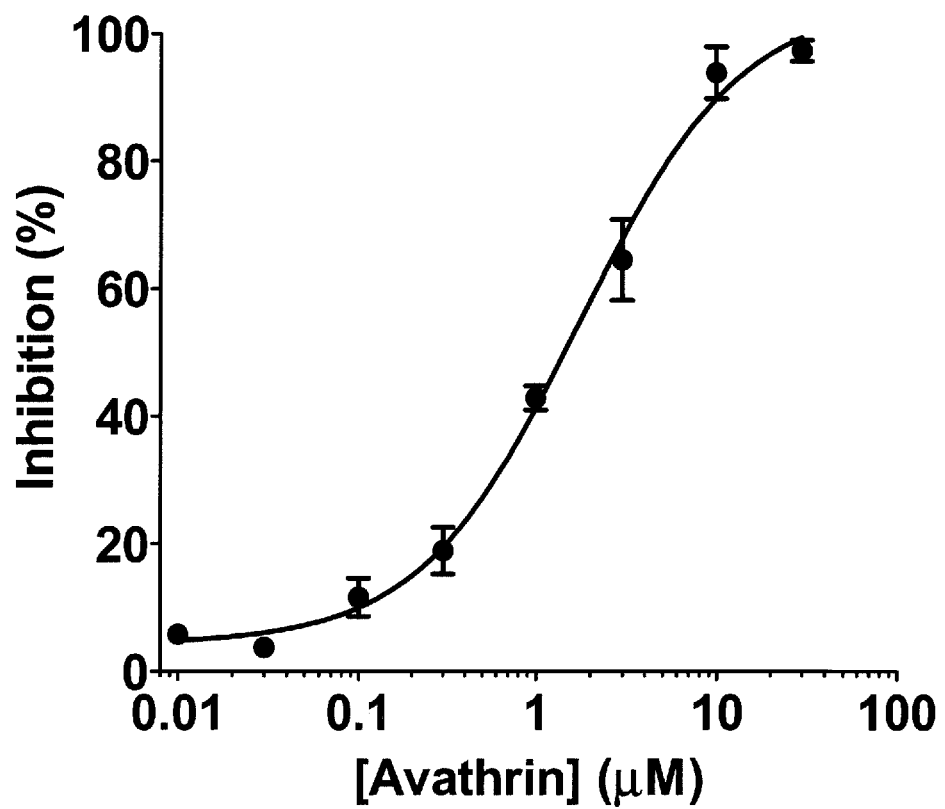

Haemostatic fibrin clots trap active thrombin, limiting its circulation [Francischetti I M B, et al., Biochemistry 38: 16678-85 (1999)]. This clot-bound thrombin is protected from inhibition by the heparin-antithrombin III complex and acts as a reservoir of active thrombin, which is thought to be instrumental in re-thrombosis [Francischetti I M B, et al., Biochemistry 38: 16678-85 (1999); Bridge K I, et al., Thromb Haemost 112: 1-8 (2014)]. Thus, the inhibition of clot-bound thrombin may prevent re-thrombosis. Therefore, we evaluated the ability of avathrin to inhibit clot-bound thrombin. Avathrin inhibited clot-bound thrombin in a dose-dependent manner with an $IC_{50}$ of 1.74±0.35 μM (FIG. 13), which is higher than thrombin in solution. Active site inhibitors, such as argatroban, rapidly and reversibly inhibit clot-bound thrombin in a concentration dependent manner with an $IC_{50}$ 2.7 μM [Berry C, et al., Thromb Haemost 72: 381-6 (1994)].

FeCl$_3$-Induced Carotid Artery Thrombosis Model

Figure 14:
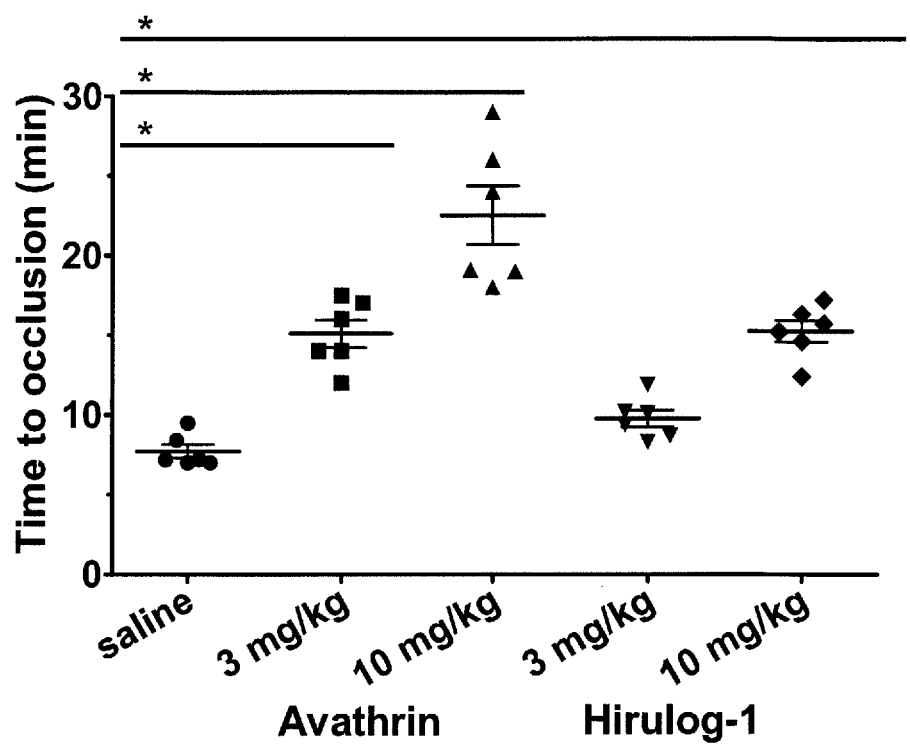

In order to evaluate the in-vivo antithrombotic efficacy of avathrin, we used the FeCl$_3$-induced carotid artery thrombosis model in mice [Wan C, et al., J Thromb Haemost 13: 248-61 (2015); Eckly a, et al., J Thromb Haemost 2011; 9: 779-89]. The average time to occlusion (TTO) increased in a dose-dependent manner in mice intravenously injected with avathrin. From 7.24±1.46 min in control animals the TTO increased to 15.03±3.23 and 22.51±4.19 min in animals injected with 3 and 10 mg/kg, respectively. The efficacy of avathrin was compared to hirulog-1 as a comparator drug. The TTO in mice injected with 3 and 10 mg/kg of hirulog-1 were 9.70±3.15 and 15.22±3.39 min, respectively. Thus, avathrin showed a better antithrombotic efficacy compared to hirulog-1 (FIG. 14).

Identification of Peptide Sequences from Ixodid Tick Transcriptomes

Peptide sequences which were similar to variegin and avathrin were identified by performing a standalone BLAST analysis of published transcriptomes of Amblyomma variegatum, Rhipicephalus pulchellus, Amblyomma americanum, Amblyomma cajenesse, Amblyomma maculatum and Hyalomma marginatum rufipes. These sequences were manually aligned with variegin and avathrin and one peptide from each tick was selected for further analysis.

Inhibition of Amidolytic Activity and Selectivity of Other Peptides

Figure 15:
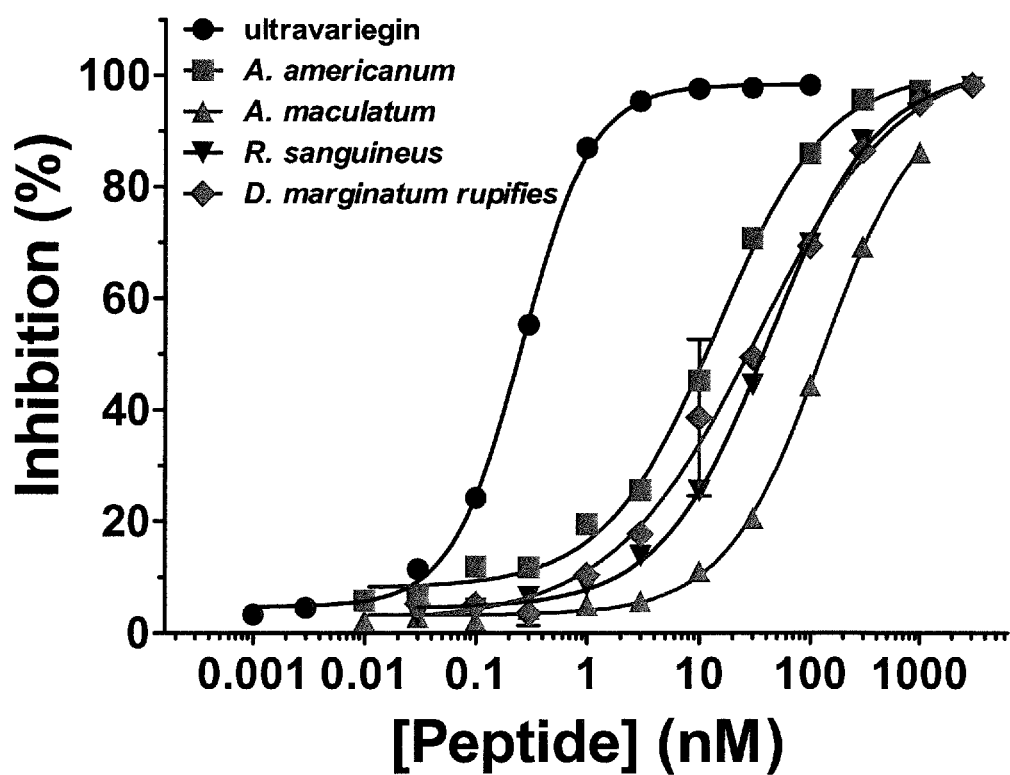

A few more protein sequences with similarity to the avathrin transcript from the A. variagatum and other hard ticks can be found in NCBI database. Some of these sequences were synthesized and tested for their thrombin inhibitory activity (FIG. 15 and Table 4). These sequences have accession numbers DAA34688.1, DAA34160.1 and DAA34258.1. Similar to avathrin transcripts they contain several repeats that may be processed through post-translational modifications to short, variegin-like mature peptides. A representative sequence was synthesized, tested for thrombin inhibition and named ultravariegin. Ultravariegin is 50% identical to variegin.

TABLE 4

Molecular weights, $IC_{50}$ and $K_i$ values of members of variegin family

| Peptide | Molecular weight (Da) | IC50 (nM) | Affinity (nM) |
|---|---|---|---|
| Avathrin | 3139.4 | 6.95 ± 0.42 | 0.545 ± 0.02 |
| Variegin | 3609.2 | 4.17 ± 0.93 | 0.283 ± 0.01 |
| Ultravariegin | 3293.5 | 0.26 ± 0.008 | 0.001 |
| Amblyomma americanum | 3830.4 | 14.29 ± 0.12 | 1.631 ± 0.61 |
| Amblyomma maculatum | 4940.6 | 130.20 ± 1.74 | — |
| Rhipicephalus sanguineus | 4773.1 | 42.38 ± 0.62 | 8.79 ± 0.61 |
| Hyalomma marginatum rufipes | 5660.7 | 32.48 ± 3.94 | 6.135 ± 0.39 |

Figure 16:
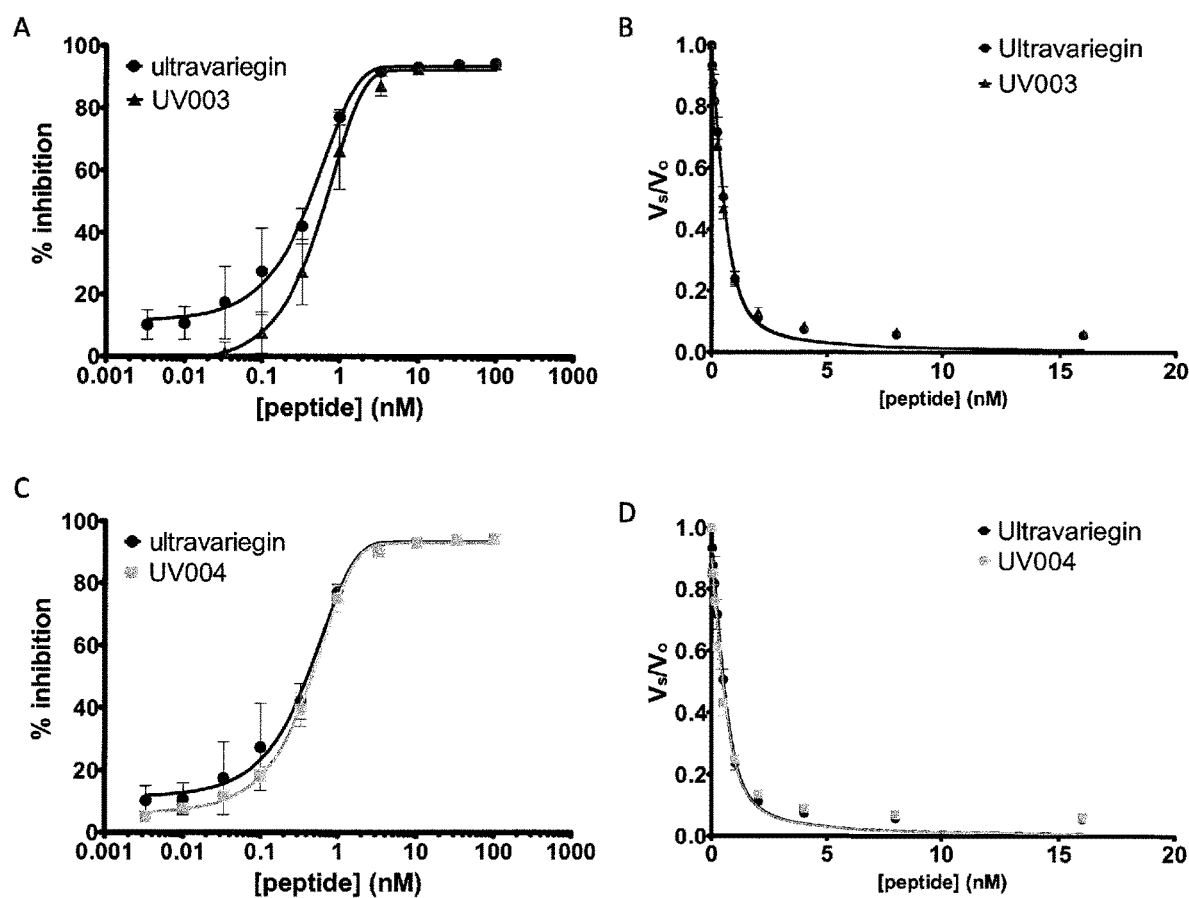

Ultravariegin is a 30-residue peptide represented by SEQ ID NO: 2 and is based on 30 residues stretch of a 212 amino acids protein sequence derived from a database transcript. However, we substituted one amino acid residue in ultravariegin from the 30 residues stretch sequence found in the 212 amino acids protein sequence (Thr22Glu to arrive at SEQ ID NO: 2). The peptide of SEQ ID NO: 2 was found to inhibit thrombin with a $K_i$ of 4.4 pM. Compared to variegin, which has a $K_i$ of 342 pM, ultravariegin is more than 70-fold more potent. To further understand structure-function relationships of ultravariegin in the inhibition of thrombin, a few more variants of ultravariegin were synthesized as follows. UV003, UV004 and UV005 are ultravariegin-variegin hybrid peptides. Based on ultravariegin sequence, the first 7 residues on the N-terminal were replaced by variegin sequence in UV003. The subsequent 7 residues were replaced in the same manner in UV004. In UV005, the last 6 residues in ultravariegin were replaced by last 8 residues of variegin (variegin has two extra residues). The $K_i$ of UV003 and UV004 were found to be similar to that of ultravariegin, showing that replacement of ultravariegin sequences with that of variegin in the first 14 residues on the N-terminal is largely inconsequential for its activity (FIG. 16). However, UV005 showed around 3.6-fold drop in affinity for thrombin. Therefore, the main difference in the inhibitory activity between variegin and ultravariegin came from their C-terminals. Sequences in the C-terminal of ultravariegin renders it a more potent inhibitor than variegin (FIGS. 17 A and C).

Figure 17:
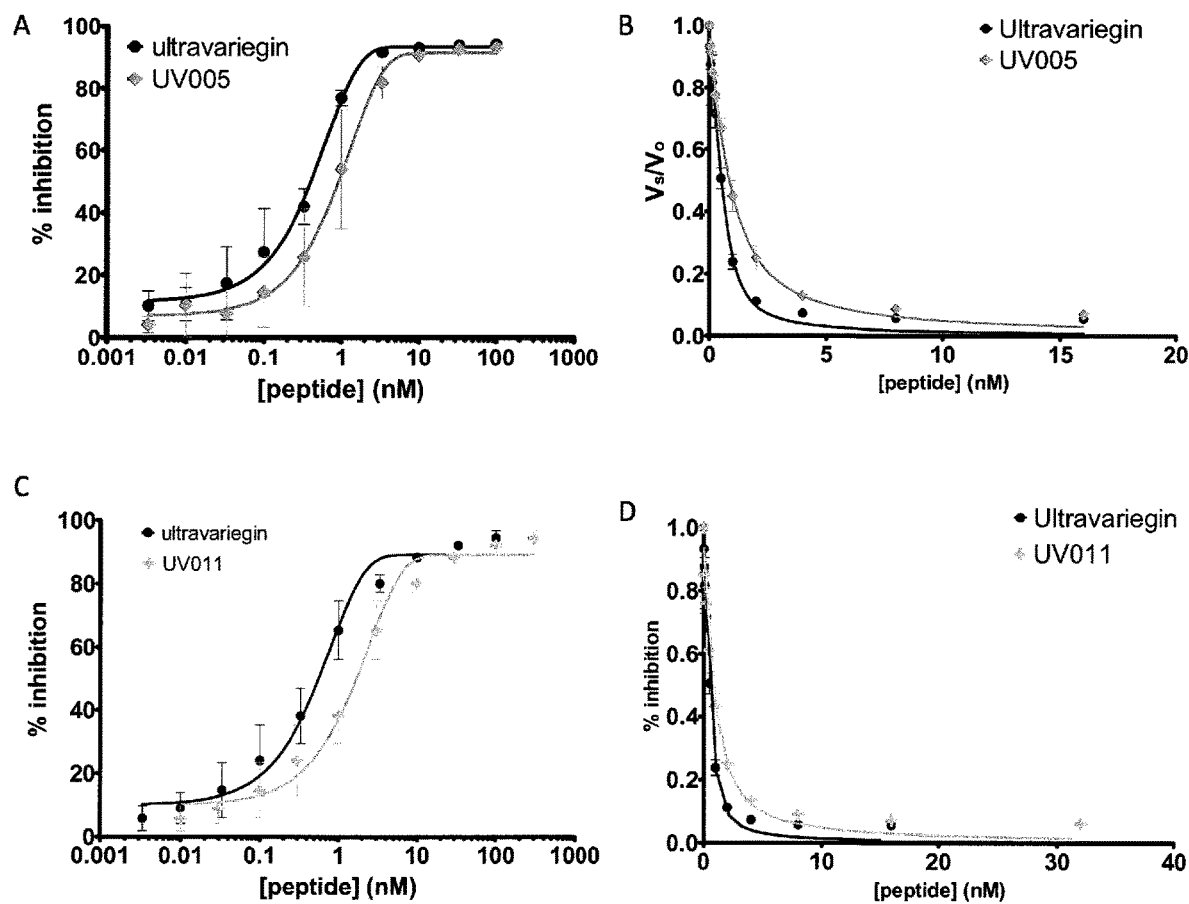

To ascertain the role of ultravariegin C-terminal, the C-terminal cleavage product of ultravariegin by thrombin was synthesized and tested as UV011 (FIGS. 17 B and D). This peptide had a $K_i$ of 1.39 nM, which is around 10-fold better than that of variegin C-terminal cleavage product (MH22, Ki=14.1 nM) and around 4-fold better than that of avathrin C-terminal cleavage product (IS20, $K_i$=5.76 nM). A mutation of Ala27 to Glu in UV012 also caused a 5-fold drop in affinity compared to ultravariegin. A mutation of Thr14 to Gln did not change the activity of ultravariegin activity (FIGS. 18 A and B). Mutations of the variegin sequence from $^V$His12-$^V$Lys13 to Tyr-Ser as ultravariegin has a $^U$Tyr12-$^U$Ser13 at this position did not significantly improve the activity of variegin (FIGS. 18 C and D). Results of all ultravariegin peptides are summarized in Table 5.

Four peptides with cysteine residue(s) either at the N- or C-terminal are synthesized and tested for activities. Peptide variants with cysteine residue(s) provide a mean to covalently immobilize the peptides on surfaces for coating. So far, addition of cysteines at the termini of peptides generally cause a slight but acceptable drop in the activity compared to analogous sequences without cysteine(s). $IC_{50}$ and $K_i$ values of the peptides are as listed in Table 5.

TABLE 5

Sequence, $IC_{50}$s and $K_i$ of ultravariegin and its variants.

| | Sequence | SEQ ID NO | $IC_{50}$ (nM) | $K_i$ (pM) |
|---|---|---|---|---|
| Ultravariegin | SDEAVRAIPKMYSTAPPGDFEEIPDDAIEE | 2 | 0.40 ± 0.09 | 4.40 ± 0.35 |
| UV003 | SDQGDVAIPKMYSTAPPGDFEEIPDDAIEE | 10 | 0.60 ± 0.20 | 4.21 ± 0.97 |
| UV004 | SDEAVRAEPKMHKTAPPGDFEEIPDDAIEE | 11 | 0.46 ± 0.08 | 4.55 ± 0.374 |
| UV005 | SDEAVRAIPKMYSTAPPGDFEEIPEEYLDDES | 12 | 0.91 ± 0.47 | 16.0 ± 3.05 |
| UV011 | MYSTAPPGDFEEIPDDAIEE | 13 | 1.66 ± 0.75 | 1387 ± 230 |
| UV012 | SDEAVRAIPKMYSTAPPGDFEEIPDDEIEE | 14 | 0.94 ± 0.68 | 23.0 ± 8.05 |
| UV013 | SDEAVRAIPKMYSQAPPGDFEEIPDDAIEE | 15 | 0.341 ± 0.07 | 4.49 ± 1.61 |
| Variegin YS | SDQGDVAEPKMYSTAPPFDFEAIPEEYLDDES | 16 | 3.16 ± 0.55 | 671 ± 076.8 |
| UV007 | CDEAVRAIPKMYSTAPPGDFEEIPDDAIEE | 18 | 0.601 ± 0.069 | 6.27 ± 1.64 |
| UV008 | SDEAVRAIPKMYSTAPPGDFEEIPDDAIEECA | 19 | 1.82 ± 0.769 | 78.6 ± 34.5 |
| UV014 | MYSTAPPGDFEEIPDDAIEEGCCC | 20 | 1.98 ± 0.665 | 2470 ± 450 |
| UV015 | SDEAVRAIPKMYSTAPPGDFEEIPDDAIEEGCCC | 21 | 1.00 ± 0.129 | 8.52 ± 1.37 |

Inhibition of thrombin amidolytic activity and selectivity of peptides from other ticks reported above was tested. All peptides were found to selectively inhibit thrombin. Kinetics and selectivity of these peptides are shown in detail in FIGS. 19 to 25.

Thrombin Inhibitors as Stabilizing Agent in Blood Collection Devices We tested variegin, ultravariegin and avathrin for anticoagulant effect in blood tubes, at room temperature, at three concentrations: 75 μM, 150 μM and 300 μM. Variegin, but not avathrin and ultravariegin, was previously included as an additive in blood tubes in a patent application (WO2012075407A2). Avathrin ($K_i$=545 pM) has similar affinity as variegin ($K_i$=318 pM) and it showed comparable anticoagulation effect as variegin (Table 6).

TABLE 6

Anticoagulation effect of variegin and related peptides in blood

| | Final concentration (micromolar) | | |
|---|---|---|---|
| | 300 | 150 | 75 |
| | Time to observe clot formation (h) | | |
| ultravariegin | 101-139 | 101-139 | 91-101 |
| avathrin | 52-66 | 52-66 | 42-52 |

TABLE 6-continued

Anticoagulation effect of variegin and related peptides in blood

| | Final concentration (micromolar) | | |
|---|---|---|---|
| | 300 | 150 | 75 |
| | Time to observe clot formation (h) | | |
| variegin | 52-66 | 52-66 | 46 |
| β-Variegin | 4 | 3-4 | 3-4 |

The time for clot formation to be observed is identical for both avathrin and variegin at the same concentration (eg. 52-66 h at 150 μM). As expected, ultravariegin outperformed avathrin and variegin (Table 3). This is consistent with the >200-fold stronger affinity of ultravariegin ($K_i$=1.5 pM) compared to the latter two peptides. Even at the lowest concentration tested, the anticoagulation effect of ultravariegin (91-101 h at 75 μM) lasted longer than the highest concentration of variegin/avathrin tested (52-66 h at 300 μM). In contrast, another variant (β-variegin) has $K_i$>30 nM (ie. >100-fold weaker than variegin) and is only able to prevent clot formation for 3-4 h. The data showed that affinity of peptides for thrombin correlated well with their anticoagulation effect in blood tubes.

Extended Stability of Blood for Platelet Function Test

We also tested the platelet aggregation responses of blood anticoagulated with ultravariegin, avathrin and variegin at 150 μM and 300 μM using Multiplate® analyzer. We used ADP (6.5 μM) as the agonist. We used citrate and hirudin as two controls. Results obtained are shown in Table 7 and FIG. 26.

TABLE 7

Tabulation of platelet aggregation responses (as area under the curve, U) of blood (ADP as agonist) in blood tubes containing various stabilizing agents.

| | Multiplate AUC at different time points (U) | | | | |
|---|---|---|---|---|---|
| | 1.5 h | 4 h | 24 h | 48 h | 72 h |
| 0.109M citrate | 37 | 32.2 | 12.9 | 1.4 | 0.7 |
| >15 μg/ml hirudin$ | 69.5 | 50.2 | 36.2 | 29.1 | 26.9 |

| | Final peptide concentration | | | | | | | | | |
|---|---|---|---|---|---|---|---|---|---|---|
| | 300 μM | 150 μM | 300 μM | 150 μM | 300 μM | 150 μM | 300 μM | 150 μM | 300 μM | 150 μM |
| ultravariegin | 66.3 | 55.7 | 46.1 | 52 | 39.5 | 43.1 | 25.4 | 7.4 | 15.4 | 9.6 |
| avathrin | 62.4 | 60.9 | 46.8 | 53.6 | 43.3 | 55.8 | 3.5 | * | * | * |
| variegin | 52.3 | 65.2 | 33.9 | 48.6 | 40.5 | 41.9 | 18.3 | * | * | * |

* No readings were obtained due to clot formation
$Concentration of hirudin is as defined in the hirudin Vacuette® tube product information considered as reliable reading, we decided on using a cut-off of 32 U (FIG. 26, dashed line). It is the response given by citrate-containing blood in our experiments at 4 h, which is the maximum analysis time recommended under the Standardization of Platelet Function Testing CLSI Guideline H58-P.

Blood tubes with ultravariegin, avathrin and variegin all showed as least 6-fold increase in stabilization window compared to the gold standard, citrate. In the first 24 h, blood in hirudin (FIG. 26, first bar from left in each set) performed similarly compared to ultravariegin (FIG. 26, second bar from left in each set), avathrin (FIG. 26, third bar from left in each set) and variegin (FIG. 26, fourth bar from left in each set), which may not be surprising given that hirudin is also a potent direct thrombin inhibitor [Warkentin T E. Best Pract Res Clin Haematol 17: 105-25 (2004)].

The relatively stronger affinities of ultravariegin and hirudin to thrombin resulted in higher aggregation responses at 48 h and 72 h, compared to the other two peptides. However, these readings are slightly below the 32 U cut-off that we set (FIG. 26).

Discussion

Despite the low overall sequence identity between avathrin and variegin (40%) and variations in key functional residues as detailed above, avathrin appears to function in a similar manner to variegin. Both inhibit thrombin as fast, tight-binding bivalent inhibitors targeting the active site and exosite-I with similar inhibitory constants ($K_i$ of variegin=342 pM, $K_i$ of avathrin=545 pM). Both variegin and avathrin bind to thrombin canonically, and are hence cleaved by thrombin upon binding. Cleavage of variegin (4 h to completion) by thrombin proceeds faster than avathrin (10 h to completion). The slower cleavage of avathrin could be due to the overall flexibility conferred by $^A$Gly15, $^A$Gly17 and $^A$Gly18. The cleavage products for both peptides inhibited thrombin non-competitively with respect to small peptidyl substrates, with the affinity of variegin cleavage product (MH22) 2-fold lower than that of avathrin's (IS20) [Koh C Y, et al., ChemBioChem 10: 2155-8 (2009)]. The slower cleavage rate of avathrin could likely be due to the higher affinity of IS20, reducing the availability of free thrombin for cleavage of the peptide at equilibrium. We have also shown that serine at position 12 appeared to confer slightly better affinity than histidine, while acidic residues at the N-terminus do not determine the fast binding kinetics. Comparison between sequences of variegin and avathrin allowed these focused structure-function studies and helped in understanding thrombin-inhibitor interactions.

The structure of the thrombin-avathrin complex is best compared to that of thrombin-hirulog-1 complex (RMSD of 0.41 Å for 279 residues) as both are peptidyl bivalent thrombin inhibitors crystallized as cleaved peptides [Skrzypczak-Jankun E, et al., J Mol Biol 221: 1379-93 (1991); Bourdon P, et al., FEBS Lett 294: 163-6 (1991)]. Hirulog-1 is a shorter peptide compared to avathrin but the two peptides show a significant degree of identity in their thrombin active site and exosite-I binding sequences. After cleavage, only the segment N-terminal to the scissile bond and the segment in exosite-I can be built in their respective structures. Both crystals have similar unit cell dimensions (C2; a/b/c≈70/72/72 Å; β≈100°). In contrast, the thrombin-variegin complex crystallized in a different crystal form (C2; a/b/c=125/51/62 Å; β=99°), and appears to have only the cleaved C-terminal peptide bound.

Both avathrin and hirulog-1 have their P1 residues binding to the same S1 pocket on thrombin. Although the P1 Lys of hirulog-1 binds to $^T$Asp189 at the bottom of the S1 pocket through a water molecule [Bode W. *Blood Cells, Mol Dis* 36: 122-30 (2006)], we observed direct interaction between $^A$Lys10 and $^T$Asp189. The same study with hirulog-1 showed a 10-fold decrease in affinity when Arg is replaced by Lys but we see a smaller change (~3-fold) with $^A$Lys10 to Arg mutation, in agreement with the direct interaction observed in the structure. Hirulog-1 and avathrin share the same P2 amino acid (Pro) and hence interact in a similar way to the S2 subsite. Hirulog-1 P3 is a $_D$-Phe, occupying the same hydrophobic pocket that avathrin P4 $^A$Ala7 occupies [Skrzypczak-Jankun E, et al., *J Mol Biol* 221: 1379-93 (1991)]. The chromogenic substrate S2238 used in all our enzymatic assays is almost identical to hirulog-1 at P3 to P1 ($_D$-Phe-Pipecolic acid-Arg). Considering that avathrin and hirulog-1 bind to the same sites on thrombin at these positions, the competitive mechanism of inhibition is in agreement with the structure.

The first six residues of exosite-I binding segments of avathrin ($^{19}$DFEEIPSDEIIE$^{30}$ of SEQ ID NO: 1), hirulog-1 (DFEEIPEEYL, SEQ ID NO: 37) and variegin ($^{19}$DFEAIPEEYLDDES$^{32}$ of SEQ ID NO: 28) are almost identical (underlined). These residues are also aligned well in the crystal structures (FIG. 27). Interactions in the three peptides with thrombin are mostly conserved across all structures. The single non-conserved residue within this segment ($^A$Glu22 vs. $^H$Glu57 vs. $^V$Ala22) is solvent exposed in all three structures without specific interactions. Variegin and hirulog-1 share the next 4 residues, $^{25}$EEYL$^{28}$ (SEQ ID NO: 41), which correspond to sequence $^{25}$SDEI$^{28}$ (SEQ ID NO: 42) in avathrin (SEQ ID NO: 1). These residues are observed in the avathrin and variegin-thrombin complexes but not in the hirulog-1-thrombin complex. Among the corresponding 4 residues of avathrin ($^{25}$SDEI$^{28}$; SEQ ID NO: 42), $^A$Ser25 and $^A$Asp26 are solvent exposed. $^A$Glu27 and $^V$Glu26 are structurally equivalent and have electrostatic interactions with $^T$Arg77A. Analysis of subsequent residues is hampered by the lack of clear density.

Despite the use of variegin sequence to design primers for amplification, we did not manage to amplify a variegin gene, suggesting a high degree of variability in the peptides produced by a multitude of genes in these ticks at different points of feeding. More surprisingly, both avathrin and variegin appear to be synthesized as larger precursor proteins containing multiple repeats, and processed into shorter active peptides which possess thrombin inhibitory activity. Despite the low overall sequence identity and variation in some key functional residues, both peptides have similar inhibitory mechanisms and effects on thrombin. A search of the database uncovered more similar sequences of such precursor proteins containing repeats of variegin-like peptides in *Amblyomma variegatum* (BM291228: 3 peptides, incomplete transcript; BM293052: five peptides; BM289492: five peptides), *Amblyomma americanum* (ACG76173: 5 peptides, incomplete transcript), and *Amblyomma cajennense* (ACAJ0085C_1: 4 peptides) [Nene V, et al., *Int J Parasitol* 32: 1447-56 (2002); Batista I F C, et al., *Toxicon* 51: 823-34 (2008)] (FIG. 28). There is also evidence for the presence of similar peptides in the salivary glands of other hard ticks like *Rhipicephalus sanguineus*, and *Hyalomma marginatum rufipes*. Most precursors can be processed into three to five peptides, forming a novel family of closely related peptidyl thrombin inhibitors. We name this family of thrombin inhibitors as Ixothrins (Ixodidae thrombin inhibitors). Ixothrins are small thrombin inhibitors without any disulphide bonds and are found in the Ixodidae (hard ticks) family. They bind to exosite 1 and the active site of thrombin. Multiple copies of ixothrins are produced in one precursor. Each precursor has the signal peptide and post-translational processing occurs either in the endoplasmic reticulum or saliva to mature ixothrins. It appears that such a multi-products approach in the production of peptidyl thrombin inhibitors is rather widespread among hard ticks. Multiplicity in salivary components to target a single host coagulation molecule is not uncommon [Francischetti I M B, et al., *J Proteomics* 71: 493-512 (2008); Fontaine A, et al., *Parasit Vectors* BioMed Central Ltd; 4: 187 (2011)], although we believe this is one of the first examples in which multiplicity is also built into a single precursor protein.

In conclusion, we have demonstrated that hard ticks disable thrombin, which is a crucial enzyme in coagulation by employing a multitude of diversified sequences while maintaining a largely similar overall scaffold and function. We have demonstrated that avathrin and several other peptides prevented thrombosis better than hirulog-1, despite similarity in sequences, in the FeCl$_3$-induced carotid artery thrombosis model. This family of molecules could produce anticoagulants useful for several clinical indications and cardiovascular procedures such as prevention of arterial thrombosis and reocclusion during invasive procedures, venous thrombosis prophylaxis after an orthopaedic surgery and management of myocardial infarction after detailed evaluation of safety and efficacy profiles [Bauer K A. *Hematology Am Soc Hematology Educ Program* 2013: 464-70 (2013)].

REFERENCES

Batista I F C, Chudzinski-Tavassi A M, Faria F, Simons S M, Barros-Batestti D M, Labruna M B, Leo L I, Ho P L, Junqueira-de-Azevedo I L M. Expressed sequence tags (ESTs) from the salivary glands of the tick *Amblyomma cajennense* (Acari: Ixodidae). *Toxicon* 2008; 51: 823-34.

Battye T G G, Kontogiannis L, Johnson O, Powell H R, Leslie A G W. iMOSFLM: A new graphical interface for diffraction-image processing with MOSFLM. *Acta Crystallogr Sect D Biol Crystallogr* 2011; 67: 271-81.

Bauer K. A. Pros and cons of new oral anticoagulants. *Haem.* 2013. 464-470.

Berliner L J. Thrombin Structure and Function. *Journal of Chemical Information and Modeling.* 1992.

Bourdon P. Hirulog peptides with sciccile bond replacements resistant to thrombin cleavage. Biochem Biophys Res Commun 1991; 177: 1049-55.

Bourdon P, Jablonski J a., Chao B H, Maraganore J M. Structure-function relationships of hirulog peptide interactions with thrombin. *FEBS Lett* 1991; 294: 163-6.

Bridge K I, Philippou H, Arisns R a S. Clot properties and cardiovascular disease. *Thromb Haemost* 2014; 112: 1-8.

Chaudhari K., Hamad B. and Syed B. A. Antithrombotic drugs market. *Nat. Rev. Drug. Discov.* 2014, 13, 571-572.

Copeland R a. Enzymes: A Practical Introduction to Structure, mechanism and Data analysis. *Enzymes: A practical Introduction to Structure, mechanism, and data analysis.* 2000.

Di Cera E. Thrombin. *Mol Aspects Med.* 2008, 29(4), 203-254.

Eckly a, Hechler B, Freund M, Zerr M, Cazenave J-P, Lanza F, Mangin P H, Gachet C. Mechanisms underlying FeCl3-induced arterial thrombosis. *J Thromb Haemost* 2011; 9: 779-89.

Emsley P, Cowtan K. Coot: Model-building tools for molecular graphics. *Acta Crystallogr Sect D Biol Crystallogr* International Union of Crystallography; 2004; 60: 2126-32.

Evans P R, Murshudov G N. How good are my data and what is the resolution? *Acta Crystallogr Sect D Biol Crystallogr* 2013; 69: 1204-14.

Francischetti I M B, Meng Z, Mans B J, Gudderra N, Hall M, Veenstra T D, Pham V M, Kotsyfakis M, Ribeiro J M C. An insight into the salivary transcriptome and proteome of the soft tick and vector of epizootic bovine abortion, Ornithodoros coriaceus. *J Proteomics* 2008, 71: 493-512.

Fontaine A, Diouf I, Bakkali N, Missé D, Pagès F, Fusai T, Rogier C, Almeras L. Implication of haematophagous arthropod salivary proteins in host-vector interactions. *Parasit Vectors* BioMed Central Ltd; 2011, 4: 187.

Gallwitz M, Enoksson M, Thorpe M, Hellman L. The extended cleavage specificity of human thrombin. *PLoS One* 2012; 7.

Huntington J. A. Natural inhibitors of thrombin. *Thromb Haemost.* 2014, 111, 583-589.

Koh C. Y., Kazimirova M., Trimnell A., Takac P., Labuda M., Nuttall P. A. and Kini R. M., Variegin, a Novel Fast and Tight Binding Thrombin Inhibitor from the Tropical Bont Tick, 2007, 282 (40), 29101-29113.

Koh C. Y. and Kini R. M. Pros and cons of new oral anticoagulants. *Expert Rev. Haematol.* 2008, 1(2), 135-139.

Koh C Y, Kazimirova M, Nuttall P a., Kini R M. Noncompetitive inhibitor of thrombin. *ChemBioChem* 2009; 10: 2155-8.

Koh C Y, Kumar S, Kazimirova M, Nuttall P a., Radhakrishnan U P, Kim S, Jagadeeswaran P, Imamura T, Mizuguchi J, Iwanaga S, Swaminathan K, Kini R M. Crystal structure of thrombin in complex with s-variegin: Insights of a novel mechanism of inhibition and design of tunable thrombin inhibitors. *PLoS One* 2011; 6.

Leslie A G W, Powell H R. Processing diffraction data with MOSFLM. *Evolving methods for macromolecular Crystallography.* 2007.

McCoy A J. Solving structures of protein complexes by molecular replacement with Phaser. *Acta Crystallogr Sect D Biol Crystallogr* International Union of Crystallography; 2006; 63: 32-41.

Michiel Coppens, John W. Eikelboom, David Gustafsson, Jeffrey I. Weitz, Jack Hirsh. Development of Direct Thrombin Inhibitors, Circ Res. 2012, 112, 920-931.

Monroe D. M., Hoffman M. and Roberts H. R. Platelets and Thrombin Generation. *Arterioscler Thromb Vasc Biol.,* 2002, 22, 1381-1389.

Nene V, Lee D, Quackenbush J, Skilton R, Mwaura S, Gardner M J, Bishop R. AvGI, an index of genes transcribed in the salivary glands of the ixodid tick Amblyomma variegatum. *Int J Parasitol* 2002; 32: 1447-56.

Qiu X, Padmanabhan K P, Carperos V E, Tulinsky a, Kline T, Maraganore J M, Fenton J W. Structure of the hirulog 3-thrombin complex and nature of the S' subsites of substrates and inhibitors. *Biochemistry* 1992; 31: 11689-97.

Raskob G. Thrombosis: A major contributor to global disease burden. *Thromb Haem.* 2014, 112(5), 843-943.

Skrzypczak-Jankun E, Carperos V E, Ravichandran K G, Tulinsky a, Westbrook M, Maraganore J M. Structure of the hirugen and hirulog 1 complexes of alpha-thrombin. *J Mol Biol* 1991; 221: 1379-93.

Stamenova P K, Marchetti T, Simeonov I. Efficacy and safety of topical hirudin (Hirudex): a double-blind, placebo-controlled study. *Eur Rev Med Pharmacol Sci.* 2001 March-April; 5(2):37-42.

Stubbs M. T. and Bode W. A player of many parts: the spotlight falls on thrombin's structure. *Throm Res.* 1993, 69, 1-58.

Versteeg H. H., Heemskerk J. W. M., Levi M., and. Reitsma P. H. New fundamentals in hemostasis. *Physiol Rev.* 2013, 93, 327-358.

Wan C, Carvalho L P D, Chan M Y, Kini R M, Kang T S. Fasxiator, a novel factor XIa inhibitor from snake venom, and its site-specific mutagenesis to improve potency and selectivity. *J Thromb Haemost* 2015; 13: 248-61.

Warkentin T E. Bivalent direct thrombin inhibitors: Hirudin and bivalirudin. *Best Pract Res Clin Haematol* 2004; 17: 105-25.

---

The invention claimed is:

1. An isolated thrombin inhibitor consisting of an amino acid sequence selected from the group consisting of:
    the amino acid sequence set forth in SEQ ID NO: 2,
    the amino acid sequence set forth in SEQ ID NO: 5,
    the amino acid sequence set forth in SEQ ID NO: 6,
    the amino acid sequence set forth in SEQ ID NO: 7,
    the amino acid sequence set forth in SEQ ID NO: 8,
    the amino acid sequence set forth in SEQ ID NO: 9,
    the amino acid sequence set forth in SEQ ID NO: 10,
    the amino acid sequence set forth in SEQ ID NO: 11,
    the amino acid sequence set forth in SEQ ID NO: 12,
    the amino acid sequence set forth in SEQ ID NO: 13,
    the amino acid sequence set forth in SEQ ID NO: 14,
    the amino acid sequence set forth in SEQ ID NO: 15,
    the amino acid sequence set forth in SEQ ID NO: 16,
    the amino acid sequence set forth in SEQ ID NO: 17,
    the amino acid sequence set forth in SEQ ID NO: 18,
    the amino acid sequence set forth in SEQ ID NO: 19,
    the amino acid sequence set forth in SEQ ID NO: 20, and
    the amino acid sequence set forth in SEQ ID NO: 21.

2. The isolated thrombin inhibitor of claim 1, wherein said inhibitor inhibits thrombin fibrinogenolytic activity and/or inhibits thrombin amidolytic activity.

3. The isolated thrombin inhibitor of claim 1, which is a synthetic polypeptide.

4. The isolated thrombin inhibitor of claim 1, which is a recombinant polypeptide.

5. The isolated thrombin inhibitor of claim 1, wherein said inhibitor consists of an amino acid sequence selected from the group consisting of:
    the amino acid sequence set forth in SEQ ID NO: 2,
    the amino acid sequence set forth in SEQ ID NO: 9,
    the amino acid sequence set forth in SEQ ID NO: 10,
    the amino acid sequence set forth in SEQ ID NO: 11,
    the amino acid sequence set forth in SEQ ID NO: 12,
    the amino acid sequence set forth in SEQ ID NO: 13,
    the amino acid sequence set forth in SEQ ID NO: 14,
    the amino acid sequence set forth in SEQ ID NO: 15,
    the amino acid sequence set forth in SEQ ID NO: 16,
    the amino acid sequence set forth in SEQ ID NO: 17,
    the amino acid sequence set forth in SEQ ID NO: 18,
    the amino acid sequence set forth in SEQ ID NO: 19,
    the amino acid sequence set forth in SEQ ID NO: 20, and
    the amino acid sequence set forth in SEQ ID NO: 21.

6. The isolated thrombin inhibitor of claim 5, wherein said inhibitor inhibits thrombin fibrinogenolytic activity and/or inhibits thrombin amidolytic activity.

7. The isolated thrombin inhibitor of claim 5, which is a synthetic polypeptide.

8. The isolated thrombin inhibitor of claim 5, which is a recombinant polypeptide.

9. A pharmaceutical composition comprising an effective amount of at least one thrombin inhibitor of claim 1.

10. A kit to modulate thrombin activity, comprising at least one thrombin inhibitor defined in claim 1.

11. A pharmaceutical composition comprising an effective amount of at least one thrombin inhibitor of claim 5.

12. A kit to modulate thrombin activity, comprising at least one thrombin inhibitor defined in claim 5.

13. A method of inhibiting thrombin activity, wherein the method comprises contacting thrombin with at least one thrombin inhibitor of claim 1.

14. The method of claim 13, wherein the at least one thrombin inhibitor is present as an anticlotting agent in blood collection tubes.

15. The method of claim 13, wherein the at least one thrombin inhibitor is present as a surface coating material on a medical device.

16. The method of claim 15, wherein the medical device is a stent, a catheter, or a medical tubing.

17. A method of inhibiting thrombin activity, wherein the method comprises contacting thrombin with at least one thrombin inhibitor of claim 5.

18. The method of claim 17, wherein the at least one thrombin inhibitor is present as an anticlotting agent in blood collection tubes.

19. The method of claim 17, wherein the at least one thrombin inhibitor is present as a surface coating material on a medical device.

20. The method of claim 19, wherein the medical device is a stent, a catheter, or a medical tubing.

\* \* \* \* \*

SEQUENCE LISTING

```
<160> NUMBER OF SEQ ID NOS: 42

<210> SEQ ID NO 1
<211> LENGTH: 30
<212> TYPE: PRT
<213> ORGANISM: Amblyomma variegatum

<400> SEQUENCE: 1

Ser Gly Gly His Gln Thr Ala Val Pro Lys Ile Ser Lys Gln Gly Leu
1               5                   10                  15

Gly Gly Asp Phe Glu Glu Ile Pro Ser Asp Glu Ile Ile Glu
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Amblyomma variegatum
<220> FEATURE:
```

```
<223> OTHER INFORMATION: Thr22Glu substitution of native Amblyomma
      variegatum sequence

<400> SEQUENCE: 2

Ser Asp Glu Ala Val Arg Ala Ile Pro Lys Met Tyr Ser Thr Ala Pro
1               5                   10                  15

Pro Gly Asp Phe Glu Glu Ile Pro Asp Asp Ala Ile Glu Glu
            20                  25                  30

<210> SEQ ID NO 3
<211> LENGTH: 26
<212> TYPE: PRT
<213> ORGANISM: Amblyomma variegatum

<400> SEQUENCE: 3

Gln Thr Ala Val Pro Lys Ile Ser Lys Gln Gly Leu Gly Gly Asp Phe
1               5                   10                  15

Glu Glu Ile Pro Ser Asp Glu Ile Ile Glu
            20                  25

<210> SEQ ID NO 4
<211> LENGTH: 20
<212> TYPE: PRT
<213> ORGANISM: Amblyomma variegatum

<400> SEQUENCE: 4

Ile Ser Lys Gln Gly Leu Gly Gly Asp Phe Glu Glu Ile Pro Ser Asp
1               5                   10                  15

Glu Ile Ile Glu
            20

<210> SEQ ID NO 5
<211> LENGTH: 30
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: Ser12Ala substitution of native Amblyomma
      variegatum sequence

<400> SEQUENCE: 5

Ser Gly Gly His Gln Thr Ala Val Pro Lys Ile Ala Lys Gln Gly Leu
1               5                   10                  15

Gly Gly Asp Phe Glu Glu Ile Pro Ser Asp Glu Ile Ile Glu
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: Ser12His substitution of native Amblyomma
      variegatum sequence

<400> SEQUENCE: 6

Ser Gly Gly His Gln Thr Ala Val Pro Lys Ile His Lys Gln Gly Leu
1               5                   10                  15

Gly Gly Asp Phe Glu Glu Ile Pro Ser Asp Glu Ile Ile Glu
            20                  25                  30

<210> SEQ ID NO 7
```

```
<211> LENGTH: 30
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: Lys10Arg substitution of native Amblyomma
      variegatum sequence

<400> SEQUENCE: 7

Ser Gly Gly His Gln Thr Ala Val Pro Arg Ile Ser Lys Gln Gly Leu
1               5                   10                  15

Gly Gly Asp Phe Glu Glu Ile Pro Ser Asp Glu Ile Ile Glu
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: Lys10beta homoarginine substitution of native
      Amblyomma variegatum sequence
<220> FEATURE:
<221> NAME/KEY: MOD_RES
<222> LOCATION: (10)..(10)
<223> OTHER INFORMATION: beta-homoarginine

<400> SEQUENCE: 8

Ser Gly Gly His Gln Thr Ala Val Pro Xaa Ile Ser Lys Gln Gly Leu
1               5                   10                  15

Gly Gly Asp Phe Glu Glu Ile Pro Ser Asp Glu Ile Ile Glu
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: Lys10beta homoarginine substitution of native
      Amblyomma variegatum sequence
<220> FEATURE:
<221> NAME/KEY: MOD_RES
<222> LOCATION: (10)..(10)
<223> OTHER INFORMATION: beta-homoarginine

<400> SEQUENCE: 9

Ser Asp Glu Ala Val Arg Ala Ile Pro Xaa Met Tyr Ser Thr Ala Pro
1               5                   10                  15

Pro Gly Asp Phe Glu Glu Ile Pro Asp Asp Ala Ile Glu Glu
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: ultravariegin-variegin hybrid

<400> SEQUENCE: 10

Ser Asp Gln Gly Asp Val Ala Ile Pro Lys Met Tyr Ser Thr Ala Pro
1               5                   10                  15

Pro Gly Asp Phe Glu Glu Ile Pro Asp Asp Ala Ile Glu Glu
```

-continued

<210> SEQ ID NO 11
<211> LENGTH: 30
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: ultravariegin-variegin hybrid

<400> SEQUENCE: 11

Ser Asp Glu Ala Val Arg Ala Glu Pro Lys Met His Lys Thr Ala Pro
1               5                   10                  15

Pro Gly Asp Phe Glu Glu Ile Pro Asp Asp Ala Ile Glu Glu
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: ultravariegin-variegin hybrid

<400> SEQUENCE: 12

Ser Asp Glu Ala Val Arg Ala Ile Pro Lys Met Tyr Ser Thr Ala Pro
1               5                   10                  15

Pro Gly Asp Phe Glu Glu Ile Pro Glu Glu Tyr Leu Asp Asp Glu Ser
            20                  25                  30

<210> SEQ ID NO 13
<211> LENGTH: 20
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: ultravariegin C-terminal thrombin cleavage
      product

<400> SEQUENCE: 13

Met Tyr Ser Thr Ala Pro Pro Gly Asp Phe Glu Glu Ile Pro Asp Asp
1               5                   10                  15

Ala Ile Glu Glu
            20

<210> SEQ ID NO 14
<211> LENGTH: 30
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: ultravariegin Ala27Glu substitution

<400> SEQUENCE: 14

Ser Asp Glu Ala Val Arg Ala Ile Pro Lys Met Tyr Ser Thr Ala Pro
1               5                   10                  15

Pro Gly Asp Phe Glu Glu Ile Pro Asp Asp Glu Ile Glu Glu
            20                  25                  30

<210> SEQ ID NO 15
<211> LENGTH: 30
<212> TYPE: PRT

```
<213> ORGANISM: Artificial Sequence
<220> FEATURE:
<223> OTHER INFORMATION: Amblyomma variegatum
<220> FEATURE:
<223> OTHER INFORMATION: ultravariegin Thr14Gln substitution

<400> SEQUENCE: 15

Ser Asp Glu Ala Val Arg Ala Ile Pro Lys Met Tyr Ser Gln Ala Pro
1               5                   10                  15

Pro Gly Asp Phe Glu Glu Ile Pro Asp Asp Ala Ile Glu Glu
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: variegin variant

<400> SEQUENCE: 16

Ser Asp Gln Gly Asp Val Ala Glu Pro Lys Met Tyr Ser Thr Ala Pro
1               5                   10                  15

Pro Phe Asp Phe Glu Ala Ile Pro Glu Glu Tyr Leu Asp Asp Glu Ser
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: beta homoarginine variegin variant
<220> FEATURE:
<221> NAME/KEY: MOD_RES
<222> LOCATION: (10)..(10)
<223> OTHER INFORMATION: beta homoarginine

<400> SEQUENCE: 17

Ser Asp Gln Gly Asp Val Ala Glu Pro Xaa Met His Ser Thr Ala Pro
1               5                   10                  15

Pro Phe Asp Phe Glu Ala Ile Pro Glu Glu Tyr Leu Asp Asp Glu Ser
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: ultravariegin N-terminal Cys

<400> SEQUENCE: 18

Cys Asp Glu Ala Val Arg Ala Ile Pro Lys Met Tyr Ser Thr Ala Pro
1               5                   10                  15

Pro Gly Asp Phe Glu Glu Ile Pro Asp Asp Ala Ile Glu Glu
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Amblyomma variegatum
```

<220> FEATURE:
<223> OTHER INFORMATION: ultravariegin C-terminal Cys

<400> SEQUENCE: 19

Ser Asp Glu Ala Val Arg Ala Ile Pro Lys Met Tyr Ser Thr Ala Pro
1 5 10 15

Pro Gly Asp Phe Glu Glu Ile Pro Asp Asp Ala Ile Glu Glu Cys Ala
20 25 30

<210> SEQ ID NO 20
<211> LENGTH: 24
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: ultravariegin fragment c-terminal CysCysCys

<400> SEQUENCE: 20

Met Tyr Ser Thr Ala Pro Pro Gly Asp Phe Glu Glu Ile Pro Asp Asp
1 5 10 15

Ala Ile Glu Glu Gly Cys Cys Cys
20

<210> SEQ ID NO 21
<211> LENGTH: 34
<212> TYPE: PRT
<213> ORGANISM: Artificial Sequence
<220> FEATURE:
<223> OTHER INFORMATION: Amblyomma variegatum
<220> FEATURE:
<223> OTHER INFORMATION: ultravariegin C-terminal CysCysCys

<400> SEQUENCE: 21

Ser Asp Glu Ala Val Arg Ala Ile Pro Lys Met Tyr Ser Thr Ala Pro
1 5 10 15

Pro Gly Asp Phe Glu Glu Ile Pro Asp Asp Ala Ile Glu Glu Gly Cys
20 25 30

Cys Cys

<210> SEQ ID NO 22
<211> LENGTH: 35
<212> TYPE: PRT
<213> ORGANISM: Amblyomma americanum

<400> SEQUENCE: 22

Ser Gly Glu Asp His Thr Ala Val Pro Lys Met Ser Arg Lys Gly Leu
1 5 10 15

Gly Gly Asp Phe Glu Asp Ile Pro Pro Glu Ala Tyr Glu Arg Ala Leu
20 25 30

Glu Ala Arg
35

<210> SEQ ID NO 23
<211> LENGTH: 46
<212> TYPE: PRT
<213> ORGANISM: Amblyomma maculatum

<400> SEQUENCE: 23

Glu Leu Glu Ser Gly Asp Glu Asp Ser Glu Gly Gly Asp Ser Gln Ser
1 5 10 15

Ser Pro Thr Glu Ser Ala Ala Pro Arg Leu His Gln Arg Glu Gly Gly
20 25 30

```
Gly Gly Asp Phe Glu Asn Val Glu Tyr Asp Gln Asp Gln Lys
        35                  40                  45

<210> SEQ ID NO 24
<211> LENGTH: 46
<212> TYPE: PRT
<213> ORGANISM: Rhipicephalus sanguineus

<400> SEQUENCE: 24

Ser Asp Val Ala Pro Ala Asp Tyr Glu Ser Asp Glu Gly Asp Asn Asp
1               5                   10                  15

Gly Gly His Asp Gly Ser Glu Val Ala Lys Pro Lys Met Pro Arg Gly
            20                  25                  30

Asn Gly Gly Gly Gly Asp Phe Glu Glu Ile Pro Glu Val Glu
        35                  40                  45

<210> SEQ ID NO 25
<211> LENGTH: 51
<212> TYPE: PRT
<213> ORGANISM: Hyalomma marginatum

<400> SEQUENCE: 25

Thr Gly Ser Asp Asp Asp Asp Glu Tyr Asp Met Tyr Glu Ser Asp Gly
1               5                   10                  15

Asp Ser Asn Glu Gly Asn Asp Asn Asp Glu Phe Glu Thr Ala Val Pro
            20                  25                  30

Arg Leu Pro Asn Pro Asn Ser Gly Arg Asp Ser Glu His Ile Pro Met
        35                  40                  45

Pro Val Asn
    50

<210> SEQ ID NO 26
<211> LENGTH: 90
<212> TYPE: DNA
<213> ORGANISM: Artificial Sequence
<220> FEATURE:
<223> OTHER INFORMATION: Amblyomma variegatum
<220> FEATURE:
<223> OTHER INFORMATION: Avathrin

<400> SEQUENCE: 26
tcgggtggcc atcagactgc tgttccgaag atatctaagc aaggcttggg tggagacttt      60
gaagaaattc caagtgatga ataatcgag                                       90

<210> SEQ ID NO 27
<211> LENGTH: 90
<212> TYPE: DNA
<213> ORGANISM: Artificial Sequence
<220> FEATURE:
<223> OTHER INFORMATION: Amblyomma variegatum
<220> FEATURE:
<223> OTHER INFORMATION: ultravariegin native

<400> SEQUENCE: 27
tcagacgaag ctgtcagggc gattcccaag atgtactcga ctgccccacc gggagatttc      60
gaaacaatcc ctgacgacgc tattgaggag                                      90

<210> SEQ ID NO 28
<211> LENGTH: 32
<212> TYPE: PRT
<213> ORGANISM: Artificial Sequence
<220> FEATURE:
```

```
<223> OTHER INFORMATION: Variegin

<400> SEQUENCE: 28

Ser Asp Gln Gly Asp Val Ala Glu Pro Lys Met His Lys Thr Ala Pro
1               5                   10                  15

Pro Phe Asp Phe Glu Ala Ile Pro Glu Glu Tyr Leu Asp Asp Glu Ser
                20                  25                  30

<210> SEQ ID NO 29
<211> LENGTH: 30
<212> TYPE: PRT
<213> ORGANISM: Amblyomma variegatum

<400> SEQUENCE: 29

Ser Asn Asp Gly Ser Val Ala Gln Pro Lys Leu His Arg Gln Ser Pro
1               5                   10                  15

Gly Gly Asp Phe Glu Glu Phe Pro Glu Gln Ala Ile Glu Gln
                20                  25                  30

<210> SEQ ID NO 30
<211> LENGTH: 29
<212> TYPE: PRT
<213> ORGANISM: Amblyomma variegatum

<400> SEQUENCE: 30

Ser Asp Glu Ala Val Arg Ala Ile Pro Lys Met Tyr Ser Thr Ala Pro
1               5                   10                  15

Pro Gly Asp Phe Glu Ile Pro Asp Asp Ala Ile Glu Glu
                20                  25

<210> SEQ ID NO 31
<211> LENGTH: 30
<212> TYPE: PRT
<213> ORGANISM: Amblyomma variegatum

<400> SEQUENCE: 31

Ser Glu Gln Ala Gly Arg Ala Val Pro Lys Met His Gln Thr Pro Pro
1               5                   10                  15

Pro Asn Asp Phe Glu Arg Ile Pro Val Glu Asp Tyr Glu Glu
                20                  25                  30

<210> SEQ ID NO 32
<211> LENGTH: 29
<212> TYPE: PRT
<213> ORGANISM: Amblyomma americanum

<400> SEQUENCE: 32

Ser Gly Glu His His Thr Ala Val Pro Lys Met Ser Arg Lys Gly Leu
1               5                   10                  15

Gly Gly Asp Phe Glu Asp Ile Pro Pro Glu Ala Tyr Glu
                20                  25

<210> SEQ ID NO 33
<211> LENGTH: 27
<212> TYPE: PRT
<213> ORGANISM: Amblyomma cajennense

<400> SEQUENCE: 33

Ser Asp Val Ala His Thr Ala Val Pro Lys Met Lys Gly Gly His Gly
1               5                   10                  15

Gly Phe Glu Pro Ile Pro Ile Asp Tyr Asp Glu
                20                  25
```

<210> SEQ ID NO 34
<211> LENGTH: 16
<212> TYPE: PRT
<213> ORGANISM: Artificial Sequence
<220> FEATURE:
<223> OTHER INFORMATION: GL16

<400> SEQUENCE: 34

Gly Leu Gly Gly Asp Phe Glu Glu Ile Pro Ser Asp Glu Ile Ile Glu
1               5                   10                  15

<210> SEQ ID NO 35
<211> LENGTH: 30
<212> TYPE: PRT
<213> ORGANISM: Artificial Sequence
<220> FEATURE:
<223> OTHER INFORMATION: Double mutant peptide L16P, G17P

<400> SEQUENCE: 35

Ser Gly Gly His Gln Thr Ala Val Pro Lys Ile Ser Lys Gln Gly Pro
1               5                   10                  15

Pro Gly Asp Phe Glu Glu Ile Pro Ser Asp Glu Ile Ile Glu
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Double mutant peptide G2D, Q5D

<400> SEQUENCE: 36

Ser Asp Gly His Asp Thr Ala Val Pro Lys Ile Ser Lys Gln Gly Leu
1               5                   10                  15

Gly Gly Asp Phe Glu Glu Ile Pro Ser Asp Glu Ile Ile Glu
            20                  25                  30

<210> SEQ ID NO 37
<211> LENGTH: 10
<212> TYPE: PRT
<213> ORGANISM: Artificial Sequence
<220> FEATURE:
<223> OTHER INFORMATION: Hirulog-1

<400> SEQUENCE: 37

Asp Phe Glu Glu Ile Pro Glu Glu Tyr Leu
1               5                   10

<210> SEQ ID NO 38
<211> LENGTH: 4
<212> TYPE: PRT
<213> ORGANISM: Artificial Sequence
<220> FEATURE:
<223> OTHER INFORMATION: First 4 residues of avathrin

<400> SEQUENCE: 38

Ser Gly Gly His
1

<210> SEQ ID NO 39
<211> LENGTH: 6
<212> TYPE: PRT
<213> ORGANISM: Artificial Sequence
<220> FEATURE:
<223> OTHER INFORMATION: Active site binding segment N-terminus to the

```
        scissile bond

<400> SEQUENCE: 39

Gln Thr Ala Val Pro Lys
1               5

<210> SEQ ID NO 40
<211> LENGTH: 10
<212> TYPE: PRT
<213> ORGANISM: Artificial Sequence
<220> FEATURE:
<223> OTHER INFORMATION: Exosite-I binding segment

<400> SEQUENCE: 40

Asp Phe Glu Glu Ile Pro Ser Asp Glu Ile
1               5                   10

<210> SEQ ID NO 41
<211> LENGTH: 4
<212> TYPE: PRT
<213> ORGANISM: Artificial Sequence
<220> FEATURE:
<223> OTHER INFORMATION: Residues 7-10 of variegin and hirulog-1

<400> SEQUENCE: 41

Glu Glu Tyr Leu
1

<210> SEQ ID NO 42
<211> LENGTH: 4
<212> TYPE: PRT
<213> ORGANISM: Artificial Sequence
<220> FEATURE:
<223> OTHER INFORMATION: Residues 7-10 of avathrin

<400> SEQUENCE: 42

Ser Asp Glu Ile
1
```